(12) United States Patent
Patzel et al.

(10) Patent No.: US 11,725,216 B2
(45) Date of Patent: Aug. 15, 2023

(54) VECTORS

(71) Applicant: NATIONAL UNIVERSITY OF SINGAPORE, Singapore (SG)

(72) Inventors: Volker Patzel, Singapore (SG); Jiang Xiaoou, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 15/579,570

(22) PCT Filed: Jun. 2, 2016

(86) PCT No.: PCT/SG2016/050258
§ 371 (c)(1),
(2) Date: Dec. 4, 2017

(87) PCT Pub. No.: WO2016/195598
PCT Pub. Date: Dec. 8, 2016

(65) Prior Publication Data
US 2018/0171354 A1 Jun. 21, 2018

(30) Foreign Application Priority Data
Jun. 3, 2015 (GB) .................................... 1509578

(51) Int. Cl.
| | | |
|---|---|---|
| C12N 15/85 | (2006.01) | |
| C12N 15/67 | (2006.01) | |
| C12N 15/63 | (2006.01) | |
| C12N 9/22 | (2006.01) | |
| C12N 15/11 | (2006.01) | |
| C12N 15/113 | (2010.01) | |
| C12P 19/34 | (2006.01) | |
| A61K 48/00 | (2006.01) | |
| C12N 9/96 | (2006.01) | |

(52) U.S. Cl.
CPC .............. *C12N 15/85* (2013.01); *C12N 9/22* (2013.01); *C12N 9/96* (2013.01); *C12N 15/11* (2013.01); *C12N 15/113* (2013.01); *C12N 15/63* (2013.01); *C12N 15/67* (2013.01); *C12P 19/34* (2013.01); *A61K 48/00* (2013.01); *C12N 2310/11* (2013.01); *C12N 2310/20* (2017.05); *C12N 2310/531* (2013.01); *C12N 2330/51* (2013.01); *C12N 2800/24* (2013.01); *C12N 2800/80* (2013.01); *C12N 2810/10* (2013.01); *C12N 2830/42* (2013.01); *C12N 2840/445* (2013.01)

(58) Field of Classification Search
CPC ...... A61K 48/00; C12N 15/11; C12N 15/113; C12N 15/63; C12N 15/67; C12N 2800/24; C12N 2800/80; C12N 2810/10; C12P 19/34
See application file for complete search history.

(56) References Cited

U.S. PATENT DOCUMENTS

| | | |
|---|---|---|
| 2003/0054392 A1 | 3/2003 | Wittig et al. |
| 2004/0259081 A1 | 12/2004 | Watzele et al. |
| 2008/0153763 A1 | 6/2008 | Takagi et al. |
| 2013/0273084 A1 | 10/2013 | Walther et al. |
| 2014/0179770 A1* | 6/2014 | Zhang ....................... A61P 3/06 514/44 R |
| 2014/0329282 A1 | 11/2014 | Nelson et al. |

FOREIGN PATENT DOCUMENTS

WO 2012032114 3/2012

OTHER PUBLICATIONS

Lim, Nicholas. Genetic reversal of the G6PD-Mahidol mutation using RNA-guided genome editing. Apr. 7, 2015. Ministry of Education, Singapore. Abstract only. (Year: 2015).*
Xiaoou, Jiang. Design of Minimal Dumbbell-Shaped DNA Vectors for Coding and Non-Coding RNA Expression. Jan. 2015. Department of Microbiology, Yong Loo Lin School of Medicine, National University of Singapore. 207 pages. (Year: 2015).*
Nafissi and Slavcev. Construction and Characterization of an in-vivo Linear Covalently Closed DNA Vector Production System. Microbial Cell Factories 2012, 11:154 (Year: 2012).*
Nafissi, N. and Slavcev, R., "Construction and characterisation of an in vivo linear covalently closed DNA vector production system", Microbial Cell Factories, 2012, vol. 11.
Schakowski, F. et al., "Minimal size MIDGE vectors improve transgene expression in vivo", In Vivo, 2007, vol. 21, pp. 17-24.
Yu, H. et al., "Efficient production of superior dumbbell-shaped DNA minimal vectors for small hairpin RNA expression", Nucleic Acids Research, 2015, vol. 43, No. 18, Jun. 11, 2015.
Cost, G.J., "Enzymatic ligation assisted by nucleases: simultaneous ligation and digestion promote the ordered assembly of DNA," Nature Protocols, vol. 2, No. 9, pp. 2198-2202 (Sep. 6, 2007).
Hwang, H.C., et al., "Gene Therapy Using Adenovirus Carrying the Herpes Simplex-Thymicline Kinase Gene to Treat In Vivo Models of Human Malignant Mesothelioma and Lung Cancer," American Journal of Respiratory Dell and Molecular Biology, vol. 13, Issue1, pp. 7-16 (Jul. 1995).
Lin, C., et al., "Rolling-Circle Amplification of a DNA Nanojunction," Angewandte Chemical International Edition, vol. 45, pp. 7537-7539 (2006).
Mansfiel, S.G., et al., "RNA repair using spliceosomemediated RNA trans-splicing," Trends in Molecular Medicine, vol. 10, No. 6, pp. 263-268 (Jun. 2004).

(Continued)

*Primary Examiner* — Samuel C Woolwine
*Assistant Examiner* — Tiffany Nicole Grooms
(74) *Attorney, Agent, or Firm* — Maschoff Brennan

(57) ABSTRACT

We disclose dumbbell-shaped vectors adapted for efficient expression in mammalian cells. We also disclose a novel method allowing the efficient synthesis of dumbbell-shaped vectors at low cost for delivery of recombinant DNA and RNA into host cells; and the use of dumbbell-shaped vectors for transient expression in, for example, primary human cells.

18 Claims, 39 Drawing Sheets
Specification includes a Sequence Listing.

(56) References Cited

OTHER PUBLICATIONS

Miller, A.M, and Dean, D.A., "Tissue-specific and transcription factor-mediated nuclear entry of DNA," Advanced Drug Delivery Reviews, vol. 61, pp. 603-613 (2009).
Patzel, V., and Sczakiel, G., "Theoretical design of antisense RNA structures substantially improve annealing kinetics and efficacy in human cells," Nature Biotechnology, vol. 16, p. 64-68 (Jan. 1998).
Patzel, V., et al., "In silico selection of functional RNA molecules," In silico selection of functional RNA molecules, vol. 7, No. 3, pp. 360-369 (2004).
Schirmbeck, R., et al., "Priming of immune responses to hepatitis B surface antigen with minimal DNA expression constructs modified with a nuclear localization signal peptide," Journal of Molecular Medicine, vol. 79, pp. 343-350 (2001).
Taki, M., et al., "Small-lnterfering-RNA Expression in Cells Based on an Efficiently Constructed Dumbbell Shaped DNA," Angewandte Chemie International Edition, vol. 43, pp. 3160-3163 (2004).
Wagner, R.W., et al., "Potent and selective inhibition of gene expression by an antisense heptanucleotide," Nature Biotechnology, vol. 14, pp. 840-844 (Jul. 1996).
Patzel V, Sczakiel G (2000). In vitro selection supports the view of a kinetic control of antisense RNA-mediated inhibition of gene expression in mammalian cells Nucleic Acids Res. 28,13, 2462-6.
Patzel V, Sczakiel G (1999). Length dependence of RNA-RNA annealing. J. Mol. Biol. 294, 1127-34.
Lehmann MJ, Patzel V, Sczakiel G (2000). Theoretical design of antisense genes with statistically increased efficacy. Nucleic Acids Res 28, 13, 2597-604.
Schirmbeck R, Konig-Merediz SA, Riedl P, Kwissa M, Sack F, Schroff M, Junghans C, Reimann J, Wittig B (2001). Priming of immune responses to hepatitis B surface antigen with minimal DNA expression constructs modified with a nuclear localization signal peptide. J Mol Med (Berl) 79, 5-6, 343-50.
Brinster RL, Allen JM, Behringer RR, Gelinas RE, Palmiter RD (1988). Introns increase transcriptional efficiency in transgenic mice. Proc Natl Acad Sci U S A 85, 3, 836-40.
Mansfield SG, Chao H, Walsh CE (2004). RNA repair using spliceosome-mediated RNA trans-splicing. Trends Mol Med 10, 6, 263-8.
Kim JH, Lee SR, Li LH, Park HJ, Park JH, Lee KY, Kim MK, Shin BA, Choi SY (2011). High cleavage efficiency of a 2A peptide derived from porcine teschovirus-1 in human cell lines, zebrafish and mice. PLoS One 6, 4, e18556.
Beltinger C, Fulda S, Kammertoens T, Meyer E, Uckert W, Debatin KM (1999). Herpes simplex virus thymidine kinase/ganciclovir-induced apoptosis involves ligand-independent death receptor aggregation and activation of caspases. Proc Natl Acad Sci U S A 96, 15, 8699-704.
Jiang YX, Lu Y, Liu TJ, Yang J, Chen Y, Fang YW (2011). Using HSV-TK/GCV suicide gene therapy to inhibit lens epithelial cell proliferation for treatment of posterior capsular opacification. Mol Vis 17, 291-9.
Hwang HC, Smythe WR, Elshami AA, Kucharczuk JC, Amin KM, Williams JP, Litzky LA, Kaiser LR, Albelda SM (1995). Gene therapy using adenovirus carrying the herpes simplex-thymidine kinase gene to treat in vivo models of Tuman malignant mesothelioma and lung cancer. Am J Respir Cell Mol Biol 13, 1, 7-16.
Rumney S, Kool ET (1995). Structural Optimization of Non-Nucleotide Loop Replacements for Duplex and Triplex DNAs J. Am. Chem. Soc 117, 5635-46.
Takeshita M, Chang CN, Johnson F, Will S, Grollman AP (1987). Oligodeoxynucleotides containing synthetic abasic sites. Model substrates for DNA polymerases and apurinic/apyrimidinic endonucleases. J. Biol. Chem. 262, 10171-9.
Lin C, Xie M, Chen JJ, Liu Y, Yan H (2006). Rolling-circle amplification of a DNA nanojunction. Angew Chem Int Ed Engl 45, 45, 7537-9.
Chu BC, Orgel LE (1992). The stability of different forms of double-stranded decoy DNA in serum and nuclear extracts. Nucleic Acids Res 20, 21, 5857-8.
Sambrook J, Russell DW (2001). Molecular cloning: a laboratory manual. Cold Spring Harbor, N.Y., Cold Spring Harbor Laboratory Press.
Li M, Wilson DM, 3rd (2014). Human apurinic/apyrimidinic endonuclease 1. Antioxid Redox Signal 20, 4, 678-707.
Mohr D, Frey S, Fischer T, Guttler T, Gorlich D (2009). Characterisation of the passive permeability barrier of nuclear pore complexes. EMBO J 28, 17,2541-53.
Rybenkov W, Cozzarelli NR, Vologodskii AV (1993). Probability of DNA knotting and the effective diameter of the DNA double helix. Proc Natl Acad Sci U S A 90, 11, 5307-11.
Wiedenheft B, Sternberg SH, Doudna JA (2012). RNA-guided genetic silencing systems in bacteria and archaea. Nature 482, 7385, 331-8.
Horvath P, Barrangou R (2010). CRISPR/Cas, the immune system of bacteria and archaea. Science 327, 5962, 167-70.
Barrangou R, Fremaux C, Deveau H, Richards M, Boyaval P, Moineau S, Romero DA, Horvath P (2007). CRISPR provides acquired resistance against viruses in prokaryotes. Science 315, 5819, 1709-12.
Marraffini LA, Sontheimer EJ (2008). CRISPR interference limits horizontal gene transfer in staphylococci by targeting DNA. Science 322, 5909, 1843-5.
Jinek M, Chylinski K, Fonfara 1, Hauer M, Doudna JA, Charpentier E (2012). A programmable dual-RNA-guided DNA endonuclease in adaptive bacterial immunity Science 337, 6096, 816-21.
Ran FA, Hsu PD, Wright J, Agarwala V, Scott DA, Zhang F (2013). Genome engineering using the CRISPR-Cas9 system. Nat Protoc 8, 11, 2281-308.
Mali P, Yang L, Esvelt KM, Aach J, Guell M, DiCarlo JE, Norville JE, Church GM (2013). RNA-guided human genome engineering via Cas9. Science 339, 6121, 823-6.
Niang M, Bei AK, Madnani KG, Pelly S, Dankwa S, Kanjee U, Gunalan K, Amaladoss A, Yeo KP, Bob NS, Malleret B, Duraisingh MT, Preiser PR (2014). STEVOR is a Plasmodium falciparum erythrocyte binding protein that mediates merozoite invasion and rosetting. Cell Host Microbe 16, 1, 81-93.
Paul WE (2008). Fundamental Immunology. Philadelphia, Wolters Kluwer/Lippincott Williams & Wilkins.
Murphy K, Travers P, Walport M, Janeway C (2012). Janeway's immunobiology. New York, Garland Science.
Wagner RW, Matteucci MD, Grant D, Huang T, Froehler BC (1996). Potent and selective inhibition of gene expression by an antisense heptanucleotide Nat Biotechnol 14, 7, 840-4.
Jung U, Jiang X, Kaufmann SHE, Patzel V (2013). A universal stem-loop primer-based TaqMan RT-PCR protocol for cost efficient detection of small non-coding RNA. RNA 19, 1864-73.
Myslinski E, AméJ-C, Krol A, Carbon P (2001). An unusually compact external promoter for RNA polymerase III transcription of the human H1RNA gene. Nucleic Acids Res 29, 2502-9.
Taki M, Kato Y, Miyagishi M, Takagi Y, Sano M, Taira K (2003). A direct and efficient synthesis method fordumbell-shaped linear DNA using PCR in vitro. Nucleic Acids Res Suppl 3, 191-2.
Taki M, Kato Y, Miyagishi M, Takagi Y, Taira K (2004). Small-interfering-RNA expression in cells based on an efficiently constructed dumbbell-shaped DNA. Angew Chem Int Ed Engl 43, 24, 3160-3.
Cost GJ (2007). Enzymatic ligation assisted by nucleases: simultaneous ligation and digestion promote the ordered assembly of DNA. Nat Protoc 2, 9, 2198-202.
Cong L, Ran FA, Cox D, Lin S, Barretto R, Habib N, Hsu PD, Wu X, Jiang W, Marraffini LA, Zhang F (2013). Multiplex genome engineering using CRISPR/Cas systems. Science 339, 6121, 819-23.
Zuker M (2003). Mfold web server for nucleic acid folding and hybridization prediction. Nucleic Acids Res 31, 13, 3406-15.
Zeng Y, Wagner EJ, Cullen BR (2002). Both natural and designed micro RNAs can inhibit the expression of cognate mRNAs when expressed in human cells Mol Cell 9, 6, 1327-33.

(56) References Cited

OTHER PUBLICATIONS

Schakowski F, Gorschluter M, Junghans C, Schroff M, Buttgereit P, Ziske C, Schottker B, Konig-Merediz SA, Sauerbruch T, Wittig B, Schmidt-Wolf IG (2001). A novel minimal-size vector (MIDGE) improves transgene expression in colon carcinoma cells and avoids transfection of undesired DNA. Mol Ther 3, 5 Pt 1, 793-800.

Patzel V (2004). In silico design of functional RNA molecules. Curr Opin Drug Discov Dev 7, 3, 360-9.

Grimm D, Streetz KL, Jopling CL, Storm TA, Pandey K, Davis CR, Marion P, Salazar F, Kay MA. (2006). Fatality in mice due to oversaturation of cellular microRNA/short hairpin RNA pathways. Nature 441, 7092, 537-41.

Liang L, Wong CM, Ying Q, Fan DN, Huang S, Ding J, Yao J, Yan M, Li J, Yao M, Ng IO, He X (2010). MicroRNA-125b suppressesed human liver cancer cell proliferation and metastasis by directly targeting oncogene LIN28B2. Hepatology 52, 5, 1731-40.

Jia HY, Wang YX, Yan WT, Li HY, Tian YZ, Wang SM, Zhao HL (2012). MicroRNA-125b Functions as a Tumor Suppressor in Hepatocellular Carcinoma Cells Int J Mol Sci 13, 7, 8762-74.

Dean DA (1997). Import of Plasmid DNA into the Nucleus Is Sequence Specific. Experimental Cell Research 230, 293-302.

Dean D, Dean B, Muller S, Smith L (1999). Sequence Requirements for Plasmid Nuclear Import. Experimental Cell Research 253, 713-22.

Vacik J, Dean BS, Zimmer WE, Dean DA (1999). Cell-specific nuclear import of plasmid DNA. Gene Therapy 6, 1006-14.

Wilier AM, Dean DA (2008). Cell-specific nuclear import of plasmid DNA in smooth muscle requires tissue-specific transcription factors and DNA sequences. Gene Ther 15, 15, 1107-15.

Längle-Rouault F, Patzel V, Benavente A, Taillez M, Silvestre N, Bompard A, Sczakiel G, Jacobs E, Rittner K (1998). Up to 100-Fold Increase of Apparent Gene Expression in the Presence of Epstein-Barr Virus oriP Sequences and EBNA1: Implications of the Nuclear Import of Plasmids. Journal of Virology 72, 6181-5.

Miller A, Dean D (2009). Tissue-specific and transcription factor-mediated nuclear entry of DNA. Advanced Drug Delivery Reviews 61, 603-13.

Krützfeldt J, Rajewsky N, Braich R, Rajeev KG, Tuschl T, Manoharan M, Stoffel M (2005). Silencing of microRNAs in vivo with 'antagomirs'. Nature 438, 7068, 685-9.

Chabot S, Orio J, Castanier R, Bellard E, Nielsen SJ, Golzio M, Teissie J (2012). LNA-based oligonucleotide alectrotransfer for miRNA inhibition. Mol Ther 20, 8, 1590-8.

Meng F, Henson R, Wehbe-Janek H, Ghoshal K, Jacob ST, Patel T (2007). MicroRNA-21 regulates expression of the PTEN tumor suppressor gene in human hepatocellular cancer. Gastroenterology 133, 647-58.

Patzel V, Sczakiel G (1998). Theoretical design of antisense RNA structures substantially improves annealing kinetics and efficacy in human cells. Nature Biotechnology 16, 1, 64-8.

Paix et al., "Precision genome editing using CRISPR-Cas9 and linear repair templates in C. elegans" HHS Public Access, Oct. 11, 2019.

Paquet et al., "Efficient introduction of specific homozygous and heterozygous mutations using CRISPR/Cas9" NATIRE, vol. 533, May 5, 2016.

Ran et al., "Genome engineering using the CRISPR-Cas9 system" Nature Protocol, vol. 8No. 11, Oct. 24, 2013.

Rodriquez, Ernesto G., "Nonviral DNA vectors for immunization and therapy: design and methods for their obtention" J Mol Med, Jan. 7, 2004.

Taki et al., "Small-lnterfering-RNA Expression in Cells Based on an Efficiently Constructed Dumbbell-Shaped DNA**" Communications, Jun. 9, 2004.

Taki et al., "A Direct and efficient synthesis method for dumbell-shaped linear DNA using PCR in vitro" Nucleic Acids Research Supplement No. 3, Sep. 1, 2003.

* cited by examiner

A

B

C

A   Abasic site   Forward primers   Reverse primers

B   Abasic site   Forward primers   Reverse primers

C   Abasic site   Forward primers   Reverse primers

A

VECTORS

FIELD OF THE INVENTION

The disclosure relates to novel dumbbell-shaped vectors for use in gene therapy and including a novel method allowing the efficient synthesis of dumbbell-shaped vectors at low cost for delivery of recombinant DNA and RNA into host cells.

SEQUENCE LISTING

The sequence listing disclosed herein is included in a text file having the name "sequence.txt," created on Jun. 2, 2016, having a size of 27000 bytes. The foregoing text file is incorporated herein by reference.

BACKGROUND TO THE INVENTION

The efficiency of methods such as gene therapy of inherited and acquired genetic diseases, genetic vaccination, stem cell programming, somatic cell reprogramming, immunotherapy and manipulation of protein expression in vivo is dependent on the delivery of recombinant DNA into primary cells ex vivo or in vivo in order to trigger the expression of non-coding RNAs or proteins.

In primary cells, the expression of recombinant foreign episomal DNA (such as plasmids) is silenced within 24 hours post-delivery independent of the route of delivery. The mechanisms underlying this effect are poorly understood. Only integrating viral delivery vectors, such as retroviral, lentiviral, and AAV vectors have been successfully used to trigger medium and long-term expression in primary cells. These vectors, however, are costly considering current good Manufacturing Practise (cGMP) production standards. It is considered to be several orders of magnitude more expensive to produce viral vectors under cGMP standards than generating an equivalent quantity of 'naked' genetic material. In addition, viral vectors harbour safety risks and concerns which are associated (i) with negative interference of the integrated foreign DNA at the loci of integration (e.g. disruption of gene function and regulation), and (ii) with the involvement of components originating from pathogenic viruses. Alternatively, the direct delivery of functional RNA into primary cells results in rapid degradation and providing only short-term effects. Hence, there is a strong desire for the development of novel genetic vectors that escape transgene silencing. The present disclosure allows for sustained and safe transgene expression in primary cells solving the problem of transgene silencing.

Novel vectors such as DNA minicircles or dumbbell-shaped vectors consisting solely of a transcription unit comprising promoter, coding genes and RNA-stabilising sequences, have several advantages such as improved cellular delivery or nuclear diffusion due to the small size. Moreover, these small vectors are resistant to exonucleases due to the covalently closed structure, whereas plasmids often harbour single-strand breaks, so-called nicks, triggered by shearing forces. The lack of unnecessary bacterial sequences or resistance proteins eliminates unwanted side effects in the host, and the controlled in vitro synthesis and the option to chemically link fluorophores, cell-penetrating peptides or immune stimulatory peptides to the loop structures, allows easy manipulation of these vectors.

As described above transgenic silencing in plasmids is frequent. DNA minicircles lacking extragenic spacers between the 5' and 3' ends of the transgene expression cassette were shown to allow sustained transgene expression in mice. When compared with minicircles, dumbbell-shaped vectors can be an order of magnitude smaller in molecular weight, in particular those for the expression of small non-coding RNA. WO2012/032114 discloses a DNA expression construct comprising a dumbbell-shaped circular vector which maintains expression for seven days post injection into melanomas. The synthesis of dumbbell shaped vectors when compared to the production of traditional vectors is often complex and costly. State-of-the-art techniques are typically enzyme dependent and additionally requiring chemical synthesis. Although improvements in the methodology have been made, such as disclosed in US2008/0153763 utilising a PCR-based techniques for the synthesis of dumbbell vectors, the methods are still largely dependent on restriction enzymes making the production of dumbbell shaped vectors costly.

This disclosure relates to novel dumbbell shaped vectors adapted for efficient prolonged expression of coding or non-coding RNA, proteins and peptides in mammalian host cells including primary cells. In addition we disclose a method utilising a Gap-primer-based PCR (GP-PCR) method significantly reducing the number and amount of enzymes and oligonucleotides needed for the production of dumbbell-shaped DNA vectors. This method does not require any restriction endonucleases and creates dumbbell DNA vectors more rapidly, with higher conversion yields and higher purity, and at lower costs when compared to state-of-the-art methods. In addition, small hairpin RNA expressing dumbbells produced using the new method triggered superior target gene knockdown compared with dumbbells produced using state-of-the-art methods or compared with plasmids.

The disclosed method allows large-scale dumbbell production as required for preclinical and clinical applications. The vectors according to the invention advantageously have extended expression in primary cells and are not subject to silencing.

SUMMARY OF INVENTION

According to an aspect of the invention there is provided a dumbbell-shaped expression vector wherein said vector comprises:
  i) one or more linear or hairpin-shaped transcription cassettes each comprising a nucleotide sequence encoding a nucleic acid molecule to be expressed;
  ii) operably linked to said transcription cassette a minimal transcription promoter nucleotide sequence;
  iii) a nucleotide sequence comprising a DNA nuclear targeting sequence;
  iv) a nucleotide sequence comprising an enhancer nucleotide sequence and optionally at least one intron associated with said enhancer nucleotide sequence to enhance expression of said expressed nucleic acid molecule;
  v) a nucleotide sequence comprising a post-transcriptional regulatory element or a constitutive nuclear transport element; and
  vi) a nucleotide sequence comprising a sequence with homology to a part of a mammalian genome that can serve as repair template which is either single or double stranded for RNA-guided genome editing.

In a preferred embodiment of the invention said minimal transcription promoter sequence further comprises a transcription termination nucleotide sequence wherein transcription initiation and termination nucleotide sequences are operatively coupled.

In a further preferred embodiment of the invention said vector comprises at least one internal loop domain. Preferably, said loop domain comprises an abasic site or nucleotide mismatch.

In a preferred embodiment of the invention said abasic site comprises one or more apurinic/apyrimidinic abasic sites.

In a preferred embodiment of the invention said nucleotide mismatch comprises a tetrahydrofuran-based mimic of an abasic site.

In a preferred embodiment of the invention said post-transcriptional regulatory element is the WPRE [SEQ ID NO 11].

In a preferred embodiment of the invention said vector nucleic acid molecule as set forth in i)-vi) above is single stranded or double stranded nucleic acid.

In a preferred embodiment of the invention said mammalian genome is human.

In a preferred embodiment of the invention said nucleic acid molecule to be expressed encodes a therapeutic protein or peptide.

In a preferred embodiment of the invention said therapeutic protein is Cas9, Cas9n, hSpCas9 or hSpCas9n.

In a preferred embodiment of the invention said therapeutic protein or peptide triggers a death signal.

Examples of proteins or peptides that trigger a cellular death signal are known in the art. For example Bacterial toxins such as the cholera toxin or the diphtheria toxin, alpha toxin, anthrax toxin, exotoxin, pertussis toxin, shiga toxin, shiga-like toxin etc are known to induce cell death. Furthermore, apoptotic signals/proteins such as Fas, TNF, caspases (initiator caspases, caspase 2,8,9,10,11,12, and effector caspases, caspase 3,6,7) etc. In addition enzymes that are able to convert a non-toxic drug into a toxic component: e.g. the herpes simplex virus thymidine kinase (HSVtk) converts the rather non-toxic drug ganciclovir (GCV) into the toxic triphosphate (HSVtk/GCV system). A further example is the *Escherichia coli* purine nucleoside phosphorylase (PNP)/fludarabine suicide gene system.

In a further preferred embodiment of the invention said therapeutic protein or peptide is the HSVtk.

In an alternative preferred embodiment of the invention said expressed nucleic acid molecule is a therapeutic nucleic acid molecule.

In a preferred embodiment of the invention said therapeutic nucleic acid is a siRNA or shRNA.

In an alternative preferred embodiment of the invention said therapeutic nucleic acid molecule is an antisense RNA oligonucleotide or antisense miRNA.

In a further preferred embodiment of the invention said therapeutic nucleic acid molecule is a miRNA.

In a further preferred embodiment of the invention said therapeutic nucleic acid molecule is a trans-splicing RNA.

In a further preferred embodiment of the invention said therapeutic nucleic acid molecule is a guide RNA, single-guide RNA, crRNA, or tracrRNA.

In a preferred embodiment of the invention said therapeutic nucleic acid molecule is a trans-splicing RNA.

In an alternative preferred embodiment of the invention said therapeutic nucleic acid molecule is a pre-mRNA or mRNA.

In a further preferred embodiment of the invention said minimal transcription promoter is derived from an RNA polymerase III promoter.

In a preferred embodiment of the invention said RNA polymerase III promoter is a U6 promoter and comprises a nucleotide sequences as set forth in SEQ ID NO: 1.

In an alternative preferred embodiment of the invention said RNA polymerase III promoter is a H1 promoter comprising a nucleotide sequence as set forth in SEQ ID NO: 2.

In an alternative preferred embodiment of the invention said RNA polymerase III promoter is a minimal H1 (mH1) promoter comprising a nucleotide sequence as set forth in SEQ ID NO: 3.

In a further alternative preferred embodiment of the invention said RNA polymerase III promoter is a modified mH1 promoter that includes a restriction endonuclease cleavage site and/or an inverted polymerase III transcriptional terminator comprising a nucleotide sequence as set forth in SEQ ID NO: 4.

In a further preferred embodiment of the invention said minimal transcription promoter is derived from an RNA polymerase II promoter.

In a preferred embodiment of the invention said RNA polymerase II promoter is a CMV promoter and comprises a nucleotide sequences as set forth in SEQ ID NO: 5.

In a preferred embodiment of the invention said transcription terminator nucleotide sequence is a RNA polymerase II or RNA polymerase III termination sequence.

In a preferred embodiment of the invention said RNA polymerase III termination sequence comprises one or more motifs comprising the nucleotide sequence TTTTT.

In a preferred embodiment of the invention said DNA nuclear targeting sequence comprises the nucleotide sequence set forth in SEQ ID NO: 6 (DTSα) and/or SEQ ID NO: 7 (DTSβ).

In a preferred embodiment of the invention said enhancer nucleotide sequence comprises the nucleotide sequence set forth in SEQ ID NO: 8 (minimal enhancer: mSV40enh).

In a further preferred embodiment of the invention said enhancer nucleotide sequence comprises the nucleotide sequence set forth in SEQ ID NO: 9 (full length enhancer: fSV40enh).

In a further preferred embodiment of the invention said intron comprises the nucleotide sequence set forth in SEQ ID NO: 10.

In a further preferred embodiment of the invention said vector further encodes a detectable marker.

In a preferred embodiment of the invention said detectable marker is a fluorescence marker.

In a preferred embodiment of the invention said fluorescence marker is a fluorescent reporter protein.

The analysis of promoter activity in a tissue can be conveniently monitored by fusing a promoter to a nucleic acid that encodes a "reporter" protein or polypeptide. Examples are well known in the art and include enzymes such as β glucuronidase. Reporters that are proteinaceous fluorophores are also known in the art. Green fluorescent protein, GFP, is a spontaneously fluorescent protein isolated from coelenterates, such as the Pacific jellyfish, *Aequoria victoria*. Its role is to transduce, by energy transfer, the blue chemiluminescence of another protein, aequorin, into green fluorescent light. GFP can function as a protein tag, as it tolerates N- and C-terminal fusions to a broad variety of proteins many of which have been shown to retain native function. Most often it is used in the form of enhanced GFP in which codon usage is adapted to the human code. Other proteinaceous fluorophores include yellow, red and blue fluorescent proteins. These are commercially available from, for example, Clontech. A yet further example is firefly luciferase.

In a preferred embodiment of the invention wherein said nucleotide sequence with homology to a part of a mammalian genome is implemented into the double-stranded DNA part of the dumbbell vector.

In an alternative preferred embodiment of the invention said nucleotide sequence with homology to a part of a mammalian genome comprises a single-stranded loop of the dumbbell vector.

According to a further aspect of the invention there is provided a pharmaceutical composition comprising a dumbbell-shaped vector according to the invention.

The dumbbell-shaped vector compositions of the present invention are administered in pharmaceutically acceptable preparations. Such preparations may routinely contain pharmaceutically acceptable concentrations of salt, buffering agents, preservatives, compatible carriers and supplementary therapeutic agents. The dumbbell shaped vector compositions of the invention can be administered by any conventional route, including injection or by gradual infusion over time. The administration may, for example, intravenous, intraperitoneal, intramuscular, intracavity, subcutaneous, transdermal, oral, topical, intratracheal, nasal, intravaginal or trans-epithelial. Alternatively, the dumbbell-shaped vector or vector composition of this invention is delivered by physical methods including but not limited to liquid jet-injection, microinjection, microneedles, powder particle injection, gold particle injection, gene gun, electroporation or hydrodynamic injection.

The dumbbell-shaped vector compositions of the invention are administered in effective amounts. An "effective amount" is that amount of the dumbbell-shaped vector that alone, or together with further doses, produces the desired response. In the case of treating a disease, the desired response is inhibiting the progression of the disease. This may involve only slowing the progression of the disease temporarily, although more preferably, it involves halting the progression of the disease permanently. This can be monitored by routine methods. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The dumbbell-shaped vector compositions used in the foregoing methods preferably are sterile and contain an effective amount of dumbbell-shaped vector according to the invention for producing the desired response in a unit of weight or volume suitable for administration to a patient. The doses of vector administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. Other protocols for the administration of vector compositions will be known to one of ordinary skill in the art, in which the dose amount, schedule of injections, sites of injections, mode of administration and the like vary from the foregoing. The administration of compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the dumbbell-shaped vector compositions of the invention are applied in pharmaceutically-acceptable amounts and in pharmaceutically-acceptable compositions. The term "pharmaceutically acceptable" means a non-toxic material that does not interfere with the effectiveness of the biological activity of the active agent. Such preparations may routinely contain salts, buffering agents, preservatives, compatible carriers, and optionally other therapeutic agents' (e.g. those typically used in the treatment of the specific disease indication). When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceutical compositions containing dumbbell-shaped vectors according to the invention may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

The dumbbell-shaped vector compositions may conveniently be presented in unit dosage form and may be prepared by any of the methods well-known in the art of pharmacy. All methods include the step of bringing the active agent into association with a vector which constitutes one or more accessory ingredients. Compositions containing vectors according to the invention may be administered as aerosols and inhaled. Compositions suitable for parenteral administration conveniently comprise a sterile aqueous or non-aqueous preparation of the vectors, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1, 3-butanediol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

In an alternative embodiment of the invention said pharmaceutical composition is a DNA vaccine composition comprising an adjuvant and/or carrier.

According to an aspect of the invention there is provided a method to generate a dumbbell-shaped vector substantially free of bacterial nucleotide sequences comprising:
  i) providing a preparation comprising a first single stranded nucleic acid template comprising a target nucleic acid molecule comprising a nucleotide sequence of interest;
  ii) contacting said first single stranded nucleic acid template with an first oligonucleotide primer comprising a 5'-phosphate and a 3'-hydroxyl group that is complementary to at least part of the 3' terminal nucleotide sequence of said single stranded nucleic acid template and further comprising a 5' nucleotide sequence not complementary to the target nucleic acid molecule wherein said oligonucleotide primer comprises a modified nucleotide sequence that prevents extension of the 5' nucleotide sequence not complementary to the target nucleic acid molecule;
  iii) providing polymerase chain reaction components and primer extending the 3' annealed oligonucleotide primer to form a second template;
  iv) contacting said second template with a second oligonucleotide primer comprising a 5'-phosphate and a 3'-hydroxyl group that is complementary to at least part of the 3' terminal nucleotide sequence of said second template and further comprising a 5' nucleotide sequence not complementary to the second template wherein said oligonucleotide primer comprises a modified nucleotide sequence that prevents extension of the 5' nucleotide sequence not complementary to the second template;
  v) providing polymerase chain reaction components and primer extending the 3' annealed oligonucleotide primer to form a double stranded nucleic acid;
  vi) polymerase chain amplify the double stranded nucleic acid to synthesize a pool of template DNA and annealing said templates to create double stranded nucleic acid comprising a 5' nucleotide sequence not complementary to the target nucleic acid molecule; and
  vii) contacting the annealed template nucleic acid with a DNA ligase to link the terminal 5'-phosphate of the non-complementary 5' nucleotide sequence to the 3'-OH of said amplified template nucleic acid to create a terminal loop structure.

In a preferred method of the invention said oligonucleotide primer comprises a non-complementary nucleotide sequence of 3-200 nucleotides.

In a further preferred method of the invention said oligonucleotide primer comprises a non-complementary nucleotide sequence of 10-30 nucleotides. In a preferred method of the invention said oligonucleotide primer comprises a nucleotide sequence that is non-complementary with said target nucleic acid molecule but includes a region of internal complementarity over part of its length that forms a stem loop structure.

In a preferred method of the invention said oligonucleotide primer includes a palindromic nucleotide sequence over part of its length.

In a preferred method of the invention said oligonucleotide primer modification is the inclusion of a site that is not recognised as template for base-pairing during primer extension by the DNA polymerase in said primer.

In a preferred method of the invention said oligonucleotide primer modification is the inclusion of an abasic site in said primer.

Abasic sites are occurring naturally typically caused by DNA damage or through spontaneous mutation and define a location in DNA or RNA that has neither a purine nor a pyrimidine base. The sites are referred to as apurinic or apyrimidinic.

In a further preferred method said abasic site is an apurinic/apyrimidinic site.

In a further preferred method said apurinic/apyrimidinic sites comprise a tetrahydrofuran.

In a further preferred method said abasic site comprises at least one or at least three apurinic/apyrimidinic sites.

In a further preferred method said abasic site contains one apurinic/apyrimidinic site.

In a further preferred method of the invention said abasic site separates the region complementary to the 3' terminal nucleotide sequence of said single stranded nucleic acid template and the 5' nucleotide sequence not complementary to the target nucleic acid molecule.

In a preferred method of the invention said DNA ligase is a phage DNA ligase, for example a T4 DNA ligase or *E. coli* DNA ligase.

In an alternative preferred method of the invention said DNA ligase is a circligase.

According to a further aspect of the invention there is provided a method to generate a minimal dumbbell-shaped vector that includes a hairpin-structured expression cassette comprising:
  i) providing a preparation comprising a single stranded nucleic acid template comprising a target nucleic acid molecule comprising a minimal transcription promoter sequence;
  ii) contacting said single stranded nucleic acid template with a first oligonucleotide primer comprising a 5'-phosphate and a 3'-hydroxyl group that is complementary to at least part of the 3' terminal nucleotide sequence of said single stranded nucleic acid template and further comprising a 5' nucleotide sequence not complementary to the target nucleic acid molecule wherein said oligonucleotide primer comprises a nicking enzyme cleavage site;
  iii) providing polymerase chain reaction components to primer extend the 3' annealed oligonucleotide primer;
  iv) contacting said extended oligonucleotide primer with a second oligonucleotide primer comprising a 3'-hydroxyl group that is complementary to at least part of the 3' terminal nucleotide sequence of said extended oligonucleotide primer and further comprising a 5' nucleotide sequence not complementary to the target nucleic acid molecule wherein said oligonucleotide primer comprises a restriction endonuclease cleavage site;
  v) polymerase chain amplify the template to synthesize a pool of template DNA and annealing said templates to create double stranded nucleic acid comprising a nicking site at the 3' nucleotide sequence of the minus strand and double-strand cleavage site at the 3' nucleotide sequence of the plus strand;
  vi) digesting said pool of template DNA with a nicking enzyme and a double-strand restriction endonuclease to create a template nucleic acid comprising non-complementary 5'-phosphorylated 5' nucleotide sequences;
  vii) contacting the annealed template nucleic acid with a DNA ligase to link the terminal 5'-phosphate of the non-complementary 5' nucleotide sequence of the plus strand to the 3'-OH of said amplified template nucleic acid minus strand to create a terminal loop structure; and viii) contacting the annealed template nucleic acid with a DNA ligase to link the terminal 5'-phosphorylated 5' overhang of the minus strand to the 5'-phosphorylated 5' overhang of a preformed oligomeric stem-loop structure comprising a template DNA for the transcription of hairpin-structured RNA to create a terminal loop structure.

In a preferred method of the invention said nicking enzyme is Nb.Bpu10I.

In a preferred method of the invention said restriction endonuclease BamHI.

In a further preferred method said minimal transcription promoter is a polymerase III promoter. According to an aspect of the invention there is provided a dumbbell-shaped vector synthesized by the method according to the invention.

According to a further aspect of the invention there is provided a method for the transfection of primary cells isolated from a human subject comprising:
  i) providing an isolated sample comprising cells to be transfected;
  ii) forming a preparation comprising said isolated cell sample and contacting said sample with a dumbbell-shaped vector according to the invention;
  iii) providing transformation conditions that enable introduction of said dumbbell-shaped vector into said primary cell sample and sustained expression of a nucleic acid molecule included in said vector.

According to a further aspect of the invention there is provided an ex vivo method to treat a patient suffering from a disease that would benefit from gene therapy comprising the steps:
  i) obtaining a sample from said subject comprising cells to be transfected;
  ii) forming a cell culture preparation comprising a dumbbell-shaped vector according to the invention and providing conditions to transfect said vector into said cells; and
  iii) administering the transfected cells to said subject.

In a preferred method of the invention said isolated sample comprises stem cells.

In a preferred embodiment of the invention said stem cells are selected from the group consisting of: pluripotent stem cells, for example embryonic stem cells or induced pluripotent stem cells, multipotent stem cells, lineage restricted stem cells.

The term "stem cell" represents a generic group of undifferentiated cells that possess the capacity for self-renewal while retaining varying potentials to form differentiated cells and tissues. Stem cells can be pluripotent or multipotent. A pluripotent stem cell is a cell that has the ability to form all tissues found in an intact organism although the pluripotent stem cell cannot form an intact organism. A multipotent cell has a restricted ability to form differentiated cells and tissues. Typically adult stem cells are multipotent stem cells and are the precursor stem cells or lineage restricted stem cells that have the ability to form some cells or tissues and replenish senescing or damaged cells/tissues. Examples of multipotent stem cells include mesenchymal stem cells. Mesenchymal stem cells or MSCs differentiate into a variety of cell types that include osteoblasts, chondrocytes, myocytes, adipocytes and neurones. Typically, MSCs are obtained from bone marrow but can originate from other sources such as adipose tissue.

In a preferred method of the invention said cells are peripheral blood mononuclear cells.

In a preferred method of the invention said peripheral blood mononuclear cells includes: T-lymphocytes, [either or both $CD8^+$ T lymphocytes or $CD4^+$ T lymphocytes] B lymphocytes, Dendritic Cells, T Regulatory Cells, innate lymphoid cells or Natural Killer Cells [NK cells].

It will be apparent that "peripheral blood mononuclear cells" can be isolated from sources other than blood, for example lymph nodes and spleen, and reference to peripheral blood mononuclear cells does not limit the invention to those cells isolated from blood.

According to a further aspect of the invention there is provided a kit comprising: an oligonucleotide primer designed to be complementary to at least part of the 3' terminal nucleotide sequence of a single stranded target nucleic acid template and further comprising a 5' nucleotide sequence not complementary to the target nucleic acid molecule wherein said oligonucleotide primer comprises a modified nucleotide sequence that prevents extension of the 5' nucleotide sequence not complementary to the target nucleic acid molecule when annealed to the target.

In a preferred embodiment of the invention said kit also comprises polymerase chain reaction components.

In a preferred embodiment of the invention said kit comprises: a thermostable DNA polymerase, deoxynucleotide triphosphates and co-factors required for polymerase chain amplification.

In a preferred embodiment of the invention said kit includes a DNA ligase.

In a preferred embodiment of the invention said kit further comprises cell transfection components for the transfection of cells, preferably mammalian cells such human cells.

BRIEF DESCRIPTION OF DRAWINGS

Exemplary embodiments of the present invention will be described below in more detail, with reference to the accompanying drawings, of which.

DETAILED DESCRIPTION

Therapeutic Proteins & Peptides

Figure 1:
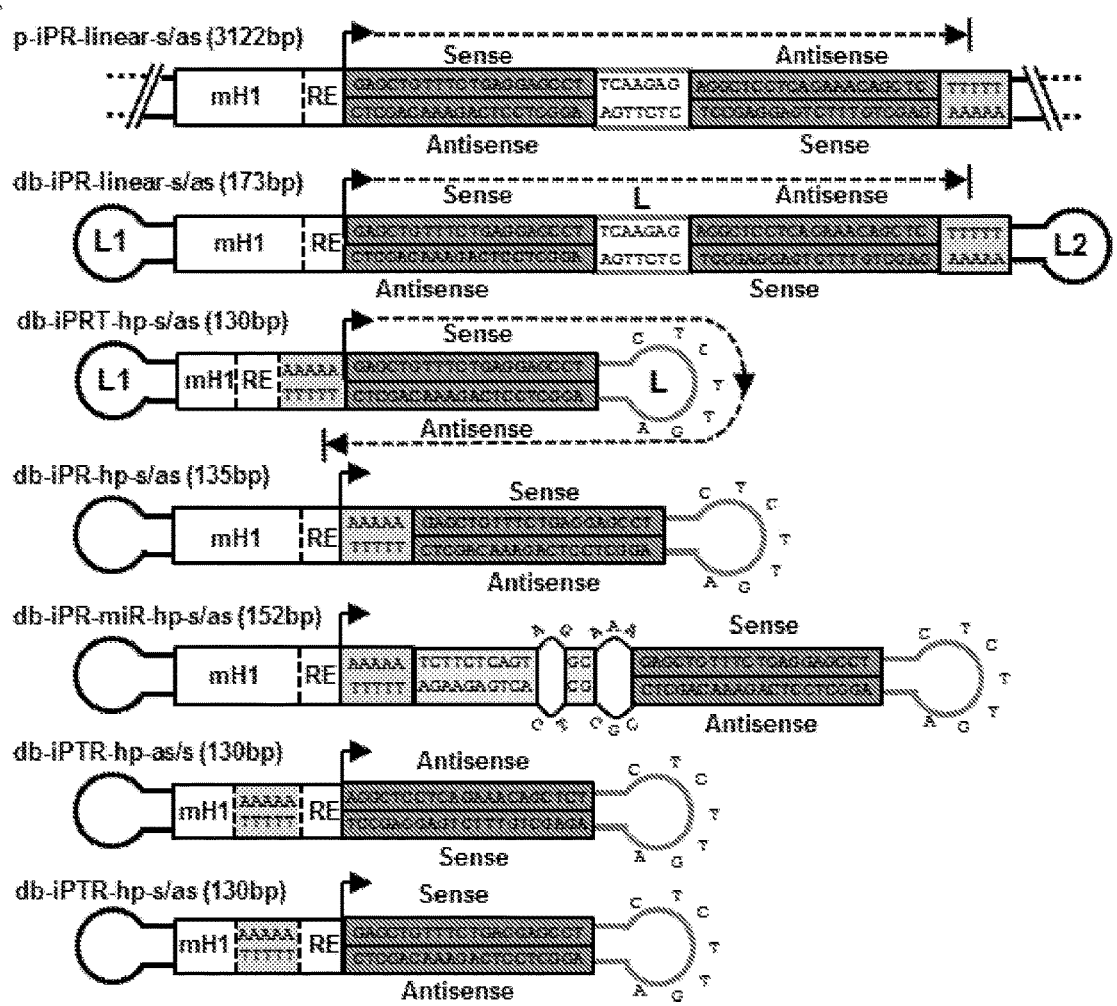
FIG. 1: Generation of novel minimised shRNA or miRNA expressing dumbbell vectors. A, Schematic drawing of novel minimised (lower part: SEQ ID NO 74, SEQ ID NO 76) and conventional (upper part: SEQ ID NO 73, SEQ ID NO 75) small RNA expressing dumbbell vectors. Structures of hairpin (hp) template-transcribing dumbbells (db) containing the minimal H1 promoter (mH1), an inverted transcriptional terminator ($A_5$) which for some constructs is integrated into the mH1 promoter forming an integrated promoter-terminator element (iPT), and a hairpin-structured shRNA transcription template in sense-loop-antisense (s/as) (SEQ ID NO 77, SEQ ID NO 78 and SEQ ID NO 80) or antisense-loop-sense (as/s) (SEQ ID NO 81) orientation. The hairpin template of construct db-miR-hp-s/as (SEQ ID NO 79) harbours a hsa-miR-30 stem (miR) extension. Conventional dumbbells harbour a linear expression cassette and separated mH1 promoter and terminator elements. B, Implementation of the inverted transcriptional terminator into the mH1 promoter for the different constructs. (SEQ ID NO 114, SEQ ID NO 115, SEQ ID NO 116 and SEQ ID NO 117) C, Novel protocol for the generation of minimised small RNA expressing dumbbells. The promoter is PCR-amplified using a 5'-phosphorylated forward primer introducing a Nb.Bpu10I cleavage site and a reverse primer introducing a sticky end producing endonucleolitic cleavage site. After enzymatic cleavage, the upstream loop forms by intramolecular ligation of the overhang. Ligation of a chemically synthesised hairpin structure-forming oligonucleotide completes the downstream portion of the dumbbell. D, Agarose gel electrophoresis analyses of the ligated dumbbells before (−) and after (+) exonuclease treatment. Different variations of the protocol trigger different indicated conversion yields. Variant (1): no purification step; variant (2): binding of an antisense oligonucleotide to the released single-stranded Nb.Bpu10I cleavage product suppresses religation; variant (3): small enzymatic cleavage products are removed by gel permeation chromatography; variant (4): combination of variants (2) and (3). HEK293T cells (E) or HepG2 cells (F) were co-transfected in 24-wells with 400 ng pGL3 and 100 ng dumbbell DNA and luciferase knock-down was monitored 48 h post transfection. Error bars indicate mean deviations from average of three to five independent experiments. Significance was tested using one-way ANOVA with Newman-Keuls post hoc test.
Figure 1:
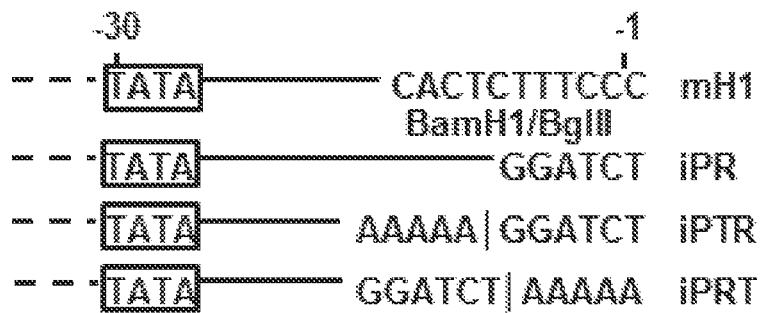
Figure 1:
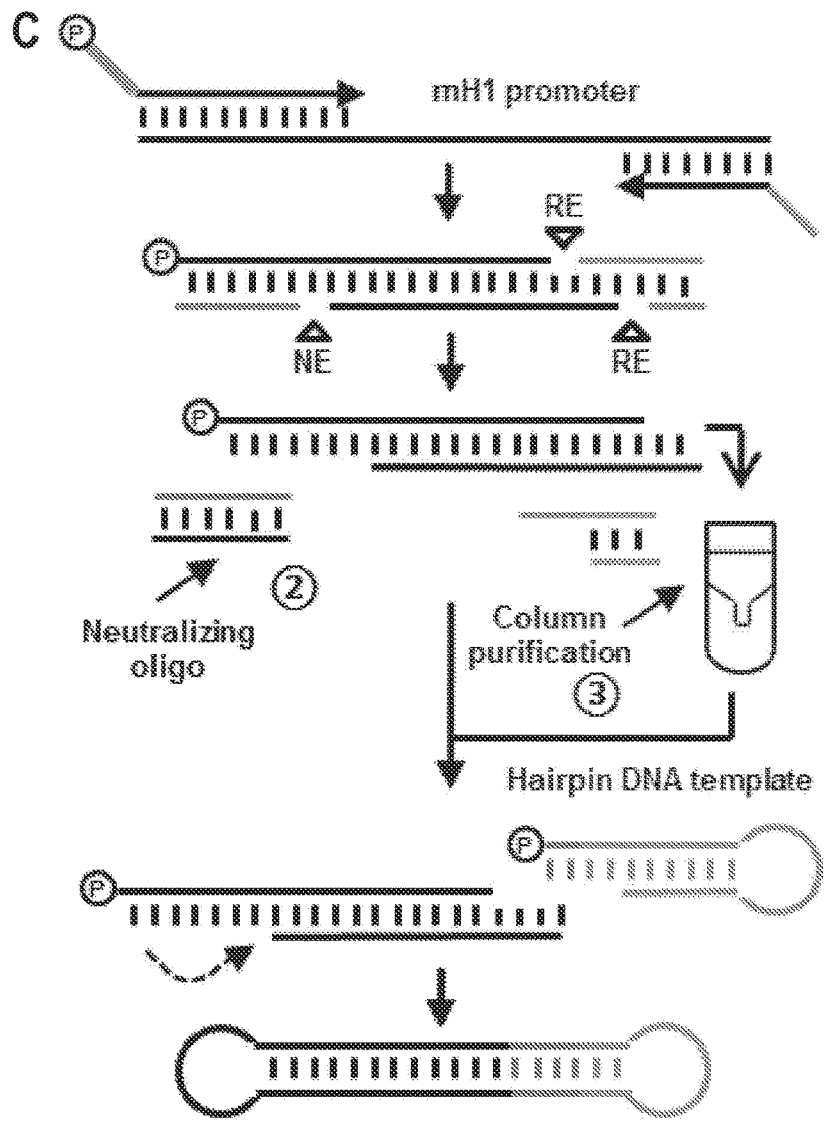
Figure 1:
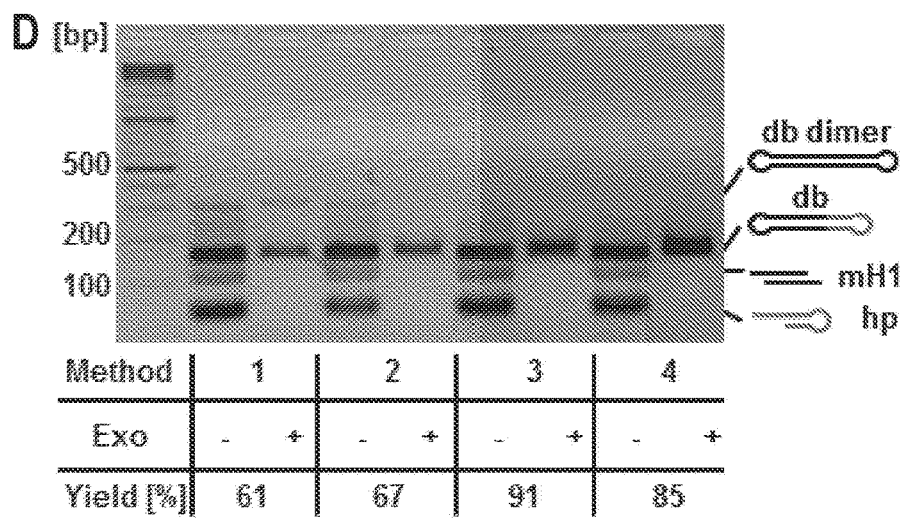
Figure 1:
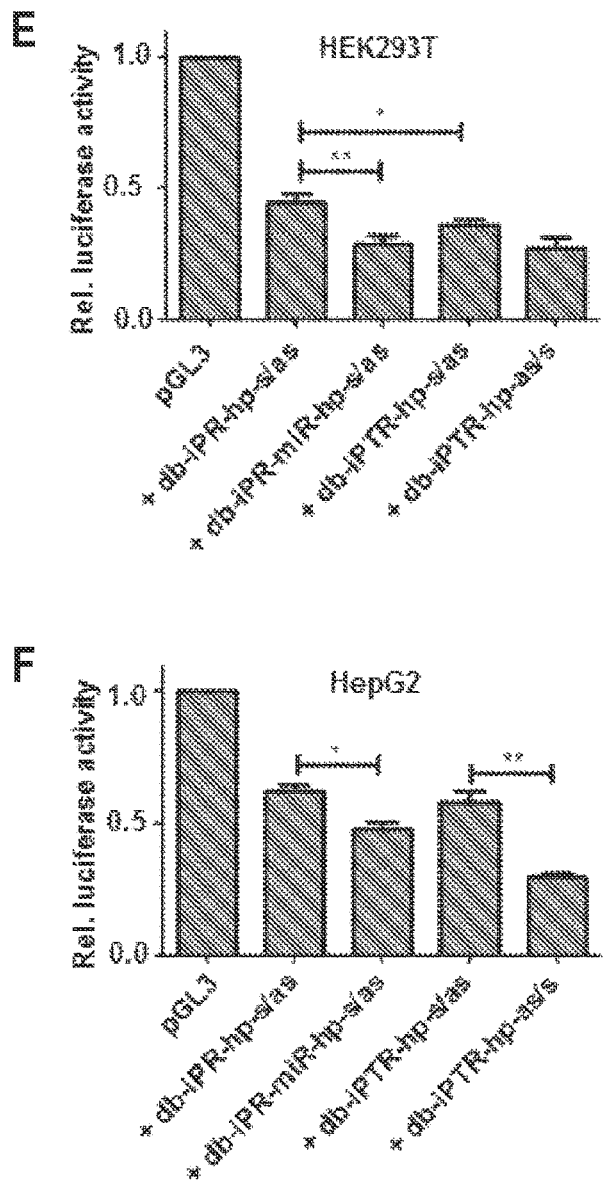

The invention encompasses dumbbell-shape vectors comprising nucleic acids encoding pharmaceutical proteins such as "cytokines". Cytokines are involved in a number of diverse cellular functions. These include modulation of the immune system, regulation of energy metabolism and control of growth and development. Cytokines mediate their effects via receptors expressed at the cell surface on target cells. Examples of cytokines include the interleukins such as: IL1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and 33. Other examples include growth hormone, leptin, erythropoietin, prolactin, tumour necrosis factor [TNF], granulocyte colony stimulating factor (GCSF), granulocyte macrophage colony stimulating factor (GMCSF), ciliary neurotrophic factor (CNTF), cardiotrophin-1 (CT-1), leukemia inhibitory factor (LIF) and oncostatin M (OSM), interferon α, interferon β, interferon ε, interferon κ and ω interferon.

Examples of pharmaceutically active peptides include GLP-1, anti-diuretic hormone, oxytocin, gonadotropin releasing hormone, corticotrophin releasing hormone; calcitonin, glucagon, amylin, A-type natriuretic hormone, B-type natriuretic hormone, ghrelin, neuropeptide Y, neuropeptide $YY_{3-36}$, growth hormone releasing hormone, somatostatin, or homologues or analogues thereof.

The term "chemokine" refers to a group of structurally related low-molecular weight factors secreted by cells having mitogenic, chemotactic or inflammatory activities. They are primarily cationic proteins of 70 to 100 amino acid residues that share four conserved cysteine residues. These proteins can be sorted into two groups based on the spacing of the two amino-terminal cysteines. In the first group, the two cysteines are separated by a single residue (C-x-C), while in the second group they are adjacent (C-C). Examples of member of the 'C-x-C' chemokines include but are not limited to platelet factor 4 (PF4), platelet basic protein (PBP), interleukin-8 (IL-8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and II (AMCF-I and -II), pre-B cell growth stimulating factor (PBSF), and IP10. Examples of members of the 'C-C' group include but are not limited to monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1 α (MIP-1-α), macrophage inflammatory protein 1β (MIP-1-β), macrophage inflammatory protein 1-γ (MIP-1-γ), macrophage inflammatory protein 3 α (MIP-3-α, macrophage inflammatory protein 3 β (MIP-3-β), chemokine (ELC), macrophage inflammatory protein-4 (MIP-4), macrophage inflammatory protein 5 (MIP-5), LD78 β, RANTES, SIS-epsilon (p500), thymus and activation-regulated chemokine (TARC), eotaxin, I-309, human protein HCC-1/NCC-2, human protein HCC-3.

A number of growth factors have been identified which promote/activate endothelial cells to undergo angiogenesis. These include vascular endothelial growth factor (VEGF A); VEGF B, VEGF C, and VEGF D; transforming growth factor (TGFb); acidic and basic fibroblast growth factor (aFGF and bFGF); and platelet derived growth factor (PDGF). VEGF is an endothelial cell-specific growth factor which has a very specific site of action, namely the promotion of endothelial cell proliferation, migration and differentiation. VEGF is a complex comprising two identical 23 kD polypeptides. VEGF can exist as four distinct polypeptides of different molecular weight, each being derived from an alternatively spliced mRNA. bFGF is a growth factor that functions to stimulate the proliferation of fibroblasts and endothelial cells. bFGF is a single polypeptide chain with a molecular weight of 16.5Kd. Several molecular forms of bFGF have been discovered which differ in the length at their amino terminal region. However the biological function of the various molecular forms appears to be the same.

Pro-drug activating polypeptides are also within the scope of the invention. The term pro-drug activating genes refers to nucleotide sequences, the expression of which, results in the production of proteins capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine (5FC) to 5 fluorouracil (5FU), a potent antitumour agent. The lysis of the tumour cell provides a localized burst of cytosine deaminase capable of converting 5FC to 5FU at the localized point of the tumour resulting in the killing of many surrounding tumour cells. Additionally, the thymidine kinase (TK) gene (see U.S. Pat. Nos. 5,631,236 and 5,601,818) in which the cells expressing the TK gene product become susceptible to selective killing by the administration of ganciclovir may be employed. Other examples of pro-drug activating enzymes are nitroreductase and cytochrome p450's (e.g. CYP1A2, CYP2E1 or CYP3A4).

Therapeutic Antibodies

Dumbbell-shaped vectors according to the invention may comprise transcription cassettes including therapeutic antibodies or antibody fragments.

Chimeric antibodies are recombinant antibodies in which all of the V-regions of a mouse or rat antibody are combined with human antibody C-regions. Humanised antibodies are recombinant hybrid antibodies which fuse the complementarity determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen. Antibodies from non-human animals provoke an immune response to the foreign antibody and its removal from the circulation. Both chimeric and humanised antibodies have reduced antigenicity when administered to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

Various fragments of antibodies are known in the art. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. A $Fab_2$ fragment comprises two joined Fab fragments. When these two fragments are joined by the immunoglobulin hinge region, a $F(ab')_2$ fragment results. An Fv fragment is multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain variable region, or a fragment thereof containing the three CDRs of the heavy chain variable region, without an associated light chain moiety; and multi specific antibodies formed from antibody fragments, this has for example been described in U.S. Pat. No. 6,248,516. Fv fragments or single region (domain) fragments are typically generated by expression in host cell lines of the relevant identified regions. These and other immunoglobulin or antibody fragments are within the scope of the invention and are described in standard immunology textbooks such as Paul, *Fundamental Immunology* (1) or Janeway et al. *Immunobiology* (2). Molecular biology now allows direct synthesis (via expression in cells or chemically) of these fragments, as well as synthesis of combinations thereof. A fragment of an antibody or immunoglobulin can also have bispecific function as described above.

RNA-Guided Genome Editing

RNA-guided genome editing is based on RNA-mediated adaptive defense systems evolved from bacteria and archaea termed clustered regulatory interspaced short palindromic repeats (CRISPR)/CRISPR-associated (Cas) systems which originally use short RNAs to direct degradation of foreign invading DNA originating from viruses or plasmids. The most common system is the *Streptococcus pyogenes* (SP) type II CRISPR system. For editing of genomic DNA in human cells several system adaptations were made: 1. The originally distinct two short RNA molecules, called CRISPR RNA (crRNA) and trans-activating crRNA (tracrRNA), necessary to guide the enzyme to the DNA target in order to trigger cleavage were fused to form a single guide RNA (gRNA). The scaffolding tracrRNA domain, hereinafter referred to as Cas-interacting domain, can be fused to any crRNA domain, hereinafter referred to as DNA binding domain (BD). 2. Codon optimization converted the SPCas9 into the hSPCas9. 3. To reduce off-target editing, an aspartate-to-alanine substitution (D10A) was introduced to convert the DNA double-strand break (DSB) triggering hSPCas9 into the DNA nickase hSPCas9n. The DNA binding domain (20 to 17 nt in length) of the gRNA can now guide the gRNA-Cas9 complex to complementary/homologous DNA sites termed protospacer, hereinafter referred to as DNA target site, which has to be followed 3' by a second short identifier called PAM (protospacer adjacent motif) which is 5'-NGG for the system described here. The BD of the gRNA can overlap with the site to be edited, or should alternatively be in proximity to this site. hSPCas9 complexes will then trigger DSBs, hSPCas9n complexes trigger nicks. Two hSPCas9n complexes with different gRNAs and shifted target sites will be required to trigger a double nick. DSBs including double nicks induced by Cas9 or Cas9n will then activate one of two endogenous repair mechanisms: 1. In the error-prone non-homologous end-joining (NHEJ) pathway, the ends will be processed and rejoined which can result in random insertion/deletion (indel) mutations. 2. Alternatively, a repair template in form of a plasmid, PCR product or single-stranded oligodeoxyribonucleotides (termed oligonucleotides in the following) can be supplied to leverage the homology-directed repair (HDR) pathway triggering high fidelity, precise editing. Single nicks trigger HDR using the intact strand as template.

Therapeutic Nucleic Acid

The invention encompasses dumbbell-shaped vectors expressing small inhibitory or interfering RNA (siRNA) complementary to a target mRNA sequence in a cell to ablate gene expression.

The siRNA molecule comprises two complementary strands of RNA (a sense strand and an antisense strand) annealed to each other to form a double stranded RNA molecule. The siRNA molecule is typically derived from exons of the gene which is to be ablated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

As used herein, the term "antisense oligonucleotide" or "antisense" describes an oligonucleotide that is an oligoribonucleotide or oligodeoxyribonucleotide which hybridizes under physiological conditions to DNA comprising a particular gene or to an mRNA transcript of that gene and thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e. to hybridize substantially more to the target sequence than to any other sequence in the target cell under physiological conditions. In order to be sufficiently selective and potent for inhibition, such antisense oligonucleotides should comprise at least 7 (3) and more preferably, at least 15 consecutive bases which are complementary to the target. Most preferably, the antisense oligonucleotides comprise a complementary sequence of 20-30 bases.

DNA Vaccines/Adjuvants

The invention encompasses dumbbell-shaped vectors encoding antigenic polypeptides in the immunisation against diseases and pathogenic organisms. Typically DNA vaccines comprising dumbbell-shaped vectors include adjuvants and/or carriers to augment immune response to encoded antigens.

Adjuvants (immune potentiators or immunomodulators) have been used for decades to improve the immune response to vaccine antigens. The incorporation of adjuvants into vaccine formulations is aimed at enhancing, accelerating and prolonging the specific immune response to vaccine antigens. Advantages of adjuvants include the enhancement of the immunogenicity of weaker antigens, the reduction of the antigen amount needed for a successful immunisation, the reduction of the frequency of booster immunisations needed and an improved immune response in elderly and immunocompromised vaccinees. Selectively, adjuvants can also be employed to optimise a desired immune response, e.g. with respect to immunoglobulin classes and induction of cytotoxic or helper T lymphocyte responses. In addition, certain adjuvants can be used to promote antibody responses at mucosal surfaces. Aluminium hydroxide and aluminium or calcium phosphate has been used routinely in human vaccines. More recently, antigens incorporated into IRIV's (immunostimulating reconstituted influenza virosomes) and vaccines containing the emulsion-based adjuvant MF59 have been licensed in countries. Adjuvants can be classified according to their source, mechanism of action and physical or chemical properties. The most commonly described adjuvant classes are gel-type, microbial, oil-emulsion and emulsifier-based, particulate, synthetic and cytokines. More than one adjuvant may be present in the final vaccine product. They may be combined together with a single antigen or all antigens present in the vaccine, or each adjuvant may be combined with one particular antigen. The origin and nature of the adjuvants currently being used or developed is highly diverse. For example, aluminium based adjuvants consist of simple inorganic compounds, PLG is a polymeric carbohydrate, virosomes can be derived from disparate viral particles, MDP is derived from bacterial cell walls; saponins are of plant origin, squalene is derived from shark liver and recombinant endogenous immunomodulators are derived from recombinant bacterial, yeast or mammalian cells. There are several adjuvants licensed for veterinary vaccines, such as mineral oil emulsions that are too reactive for human use. Similarly, complete Freund's adjuvant, although being one of the most powerful adjuvants known, is not suitable for human use.

The term carrier is construed in the following manner. A carrier is an immunogenic molecule which, when bound to a second molecule augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes.

The protein moiety of such a conjugate (the "carrier" protein) provides T-cell epitopes which stimulate helper T-cells that in turn stimulate antigen-specific B-cells to differentiate into plasma cells and produce antibody against the antigen.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example.

Sequence Listing

SEQ ID NO 1:
5'-AGGTCGGGCAGGAAGAGGGCCTATTTCCCATGATTCCTTCATATTTG
CATATACGATACAAGGCTGTTAGAGAGATAATTAGAATTAATTTGACTGT
AAACACAAAGATATTAGTACAAAATACGTGACGTAGAAAGTAATAATTTC
TTGGGTAGTTTGCAGTTTTAAAATTATGTTTTAAAATGGACTATCATATG
CTTACCGTAACTTGAAAGTATTTCGATTTCTTGGCTTTATATATCTTGTG
GAAAGGACGAAACACC-3'

SEQ ID NO 2:
5'-AATTCGAACGCTGACGTCATCAACCCGCTCCAAGGAATCGCGGGCCC
AGTGTCACTAGGCGGGAACACCCAGCGCGCGTGCGCCCTGGCAGGAAGAT
GGCTGTGAGGGACAGGGGAGTGGCGCCCTGCAATATTTGCATGTCGCTAT
GTGTTCTGGGAAATCACCATAAACGTGAAATGTCTTTGGATTTGGGAATC
TTATAAGTTCTGTATGAGACCACAGATCTAA-3'

SEQ ID NO 3:
5'-ATATTTGCATGTCGCTATGTGTTCTGGGAAATCACCATAAACGTGAA
ATGTCTTTGGATTTGGGAATCTTATAAGTTCTGTATGAGACCACAGATCT
AA-3'

SEQ ID NO 4:
5'-ATATTTGCATGTCGCTATGTGTTCTGGGAAATCACCATAAACGTGAA
ATGTCTTTGGATTTGGGAATCTTATAAGTTCTGTATGAGACGGATCTAAA
AA-3'

TABLE 1

Calculation of costs, excluding those for column purification, for the production of 1 μg dumbbell DNA based on local prices in Singapore converted into USD.

| | ELAN db | Nicking enzyme Db | AP1-hp Db | AP1-hp (exo-) db | AP3-hp db | AP1-loop db |
|---|---|---|---|---|---|---|
| Oligodeoxyribonucleotides (pmol) | FwP: 330 RvP: 110 Loop1: 70 Loop2: 70 | 1st round PCR FwP: 5.6 RvP: 5.6 2nd round PCR FwP: 70 RvP: 70 | 5'P-FwP: 65 5'P-RvP: 22 | 5'P-FwP: 65 5'P-RvP: 22 | 5'P-FwP: 94 5'P-RvP: 31 | 5'P-FwP: 94 5'P-RvP: 31 |
| DNA polymerase (units) | Pfu: 11 Taq: 22 | 1st round PCR Pfu: 2.2 Taq: 0.7 2nd round PCR Taq: 8.8 | Pfu: 2.2 Taq: 4.4 | Pfu: 2.2 Taq: 4.4 | Pfu: 3.1 Taq: 6.3 | Pfu: 3.1 Taq: 6.3 |
| Restriction endonuclease (units) | XhoI: 9.7 EcoRI: 9.7 SalI: 4.2 MfeI: 4.2 | NB. Bpu 10I: 8.8 | | | | |
| DNA ligase (units) | T4 DNA ligase: 28 | T4 DNA ligase: 17.5 | T4 DNA ligase: 10.9 | T4 DNA ligase: 10.9 | T4 DNA ligase: 31.3 | CircLigase: 555 |
| T7 DNA polymerase (units) | 28 | 17.5 | 10.9 | | 15.6 | 13.3 |
| Total expenses[a] (USD) | 72.5 | 21.1 | 13.2 | 7.0 | 23.8 | 211.1 |

-continued

SEQ ID NO 5:
5'-GAATTCAAGGTACCAGATCTTAGTTATTAATAGTAATCAATTACGGG

GTCATTAGTTCATAGCCCATATATGGAGTTCCGCGTTACATAACTTACGG

TAAATGGCCCGCCTGGCTGACCGCCCAACGACCCCCGCCCATTGACGTCA

ATAATGACGTATGTTCCCATAGTAACGCCAATAGGGACTTTCCATTGACG

TCAATGGGTGGAGTATTTACGGTAAACTGCCCACTTGGCAGTACATCAAG

TGTATCATATGCCAAGTACGCCCCCTATTGACGTCAATGACGGTAAATGG

CCCGCCTGGCATTATGCCCAGTACATGACCTTATGGGACTTTCCTACTTG

GCAGTACATCTACGTATTAGTCATCGCTATTACCATGGTGATGCGGTTTT

GGCAGTACATCAATGGGCGTGGATAGCGGTTTGACTCACGGGGATTTCCA

AGTCTCCACCCCATTGACGTCAATGGGAGTTTGTTTTGGCACCAAAATCA

ACGGGACTTTCCAAAATGTCGTAACAACTCCGCCCCATTGACGCAAATGG

GCGGTAGGCGTGTACGGTGGGAGGTCTATATAAGCAGAGCTGGTTTAGTG

AACCGTG-3'

SEQ ID NO 6:
5'-TGGTTGCTGACTAATTGAGATGCATGCTTTGCATACTT-3'

SEQ ID NO 7:
5'-AGCCTGGGGACTTTCCACACC-3'

SEQ ID NO 8:
5'-TGGTTGCTGACTAATTGAGATGCATGCTTTGCATACTTCTGCCTGCT

GGGGAGCCTGGGGACTTTCCACACC-3'

SEQ ID NO 9:
5'-CGATGGAGCGGAGAATGGGCGGAACTGGGCGGAGTTAGGGGCGGGAT

GGGCGGAGTTAGGGGCGGGACTATGGTTGCTGACTAATTGAGATGCATGC

TTTGCATACTTCTGCCTGCTGGGGAGCCTGGGGACTTTCCACACCTGGTT

GCTGACTAATTGAGATGCATGCTTTGCATACTTCTGCCTGCTGGGGAGCC

TGGGGACTTTCCACACCCTAACTGACACACATTCCACAGC-3'

SEQ ID NO 10:
5'-CAGGTAAGTATCAAGGTTACAAGACAGGTTTAAGGAGACCAATAGAA

ACTGGGCTTGTCGAGACAGAGACGACTCTTGCGTTTCTGATAGGCACCTA

TTGGTCTTACTGACATCCACTTTGCCTTTCTCTCCACAGG-3'

SEQ ID NO 11
ATAATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCATC

Primers and Enzymes
Primers for Cloning of Plasmids.
Oligodeoxyribonucleotides

SEQ ID NO 12 shR-luc-plus:
5'-GATCCGAGCTGTTTCTGAGGAGCCTTCAAGAGAGGCTCCTCAGAAA
CAGCTCTTTTTC-3', SEQ ID NO 13 shR-luc-minus:
5'-TCGAGAAAAAGAGCTGTTTCTGAGGAGCCTCTCTTGAAGGCTCCTC
AGAAACAGCT, SEQ ID NO 14 shR-gfp-plus:
5'-GATCCGCTGACCCTGAAGTTCATCTTCAAGAGAGATGAACTTCAGG
GTCAGCTTTTTC-3', SEQ ID NO 15 shR-gfp-minus:
5'-TCGAGAAAAAGCTGACCCTGAAGTTCATCTCTCTTGAAGATGAACT
TCAGGGTCAGCG-3',

SEQ ID NO 16 FW-SV40:
5'-ATGCGAGCTCCGATGGAGCGGAGAATGG-3',

SEQ ID NO 17 Rv-SV40:
5'-ATGCGAATTCGCTGTGGAATGTGTGTCAGTTAGG-3',

SEQ ID NO 18 Fw-pre-miR-125b:
5'-ATCGTCAGATCTTGCGCTCCTCTCAGTCCC-3',

SEQ ID NO 19 Rv-pre-miR-125b
5'-ATCGATAAGCTTTAAAAAAGCACGACTCGCAGCTCC-3',

SEQ ID NO 20 BD-miR-125b-plus:
5'-pTCACAAGTTAGGGTCTCAGGGAATCACAAGTTAGGGTCTCAGGGA
ATCACAAGTTAGGGTCTCAGGGA-3, SEQ ID NO 21 BD-miR-125b-minus:
5'-pAGCTTCCCTGAGACCCTAACTTGTGATTCCCTGAGACCCTAACTT
GTGATTCCCTGAGACCCTAACTTGTGAAGCT-3', SEQ ID NO 22 BD-miR-21-plus:
5'-pTCAACATCAGTCTGATAAGCTAATCAACATCAGTCTGATAAGCTA
ATCAACATCAGTCTGATAAGCTA-3',
and SEQ ID NO 23 BD-miR-21-minus:
5'-pAGCTTAGCTTATCAGACTGATGTTGATTAGCTTATCAGACTGATG
TTGATTAGCTTATCAGACTGATGTTGAAGCT-3' were synthesized by AITbiotech (Singapore).
Primers for db Production.
gpPCR method. Unmodified oligodeoxyribonucleotides Fw-luc 5'-TAGAATTCATATTTGCATGTCGCTATGT-3' (SEQ ID NO 24), and Rv-luc 5'-AACTCGAGAAAAAGAGCTGTTTCTGAG-3' (SEQ ID NO 25) were synthesized by AITbiotech (Singapore). dSpacer1 (AP1) oligodeoxyribonucleotides Fw-AP1-sh 5'-pATCCAGTTTTCTGGA-AP1-TAGAATTCATATTTG-CATGTCGCTATGT-3' (SEQ ID NO 26), Rv-AP1-sh 5'-pAAGGTCTTTTGACCT-AP1-AACTCGAGAAAAAGAGCTGTTTCTGAG-3' (SEQ ID NO 27), Fw-AP1-loop 5'-pATCCAGTTTTCAGCA-AP1-TAGAATTCATATTTGCATGTCGCTATGT-3' (SEQ ID NO 28), Rv-AP1-loop 5'-pAAGGTCTTTTCAGCA-AP1-AACTCGAGAAAAAGAGCTGTTTCTGAG-3' (SEQ ID NO 29) and dSpacer3 (AP3) oligodeoxyribonucleotides Fw-AP3-sh 5'-pATCTCCAGTTTTCTGGA-AP3-TAGAATTCATATTTGCATGTCGCTATGT-3' (SEQ ID NO 30), Rv-AP3-sh 5'-pATCAGGTCTTTTGACCT-AP3-AACTCGAGAAAAAGAGCTGTTTCTGAG-3' (SEQ ID NO 31), Fw-AP3-loop 5'-pATCTCCAGTTTTCAGCA-AP3-TAGAATTCATATTTGCATGTCGCTATGT-3' (SEQ ID NO 32), Rv-AP3-loop 5'-pATCTCCAGTTTTCAGCA-AP3-AACTCGAGAAAAAGAGCTGTTTCTGAG-3' (SEQ ID NO 33) and PEG-150 (S9) oligodeoxyribonucleotides Fw-S9-sh 5'-pATCGTCCAGTTTTCTGGA-S9-TAGAATTCATATTTGCATGTCGCTATGT-3' (SEQ ID NO 34), Rv-S9-sh 5'-pATCGAGGTCTTTTGACCT-S9-AACTCGAGAAAAAGAGCTGTTTCTGAG-3' (SEQ ID NO 35), Fw-S9-loop 5'-pATCGTCCAGTTTTCAGCA-S9-TAGAATTCATATTTGCATGTCGCTATGT-3' (SEQ ID NO 36), Rv-S9-loop 5'-pATCGAGGTCTTTTCAGCA-S9-AACTCGAGAAAAAGAGCTGTTTCTGAG-3' (SEQ ID NO 37) oligodeoxyribonucleotides were synthesized by Integrated DNA Technologies (Coralville, USA).

Generation of hairpin template-transcribing dumbbells. Fw-Bpu-mH1 5'-pTTAGGAGTTTTCTCCTAAGCATAT-TTGCATGTCGCTATGTGTTCTG-3'(SEQ ID NO 38), Rv-BamHI-mH1-pA 5'-TGCAGGATCCCTTTTTTCT-CATACAGAACTTATAAGATTCCC-3' (SEQ ID NO 39), neutralizing oligonucleotide 5'-TTAG-GAGTTTTCTCCTAA-3' (SEQ ID NO 40), hp-s/as, 5'-pGATCTAAAAAGAGCTGTTTCTGAG-GAGCCTCTCTT-GAAGGCTCCTCAGAAACAGCTCTTTTTA-3' (SEQ ID NO 41), hp-miR-s/as, 5'-pGATC-CAAAAATCTTCTCAGTAGGCAAAGAGCTGTTTCT-GAGGAGCCTCTCTTGAAGGCTCCTCA GAAACAGCTCCGCGCTCACTGAGAAGATTTTTG-3' (SEQ ID NO 42), hp-iPT-s/as, 5'-pGATCTGAGCTGTTTCTGAG-GAGCCTCTCTTGAAGGCTCCTCAGAAACAGCTCA-3' (SEQ ID NO 43), hp-iPT-as/s, 5'-pTCGACAGGCTCCTCAGAAACAGCTCTCTCTT-GAAGAGCTGTTTCTGAGGAGCCTG-3' (SEQ ID NO 44), hp-125b 5'-pGATCTAAAAAAGCACGACTCGCAGCTCC-CAAGAGCCTAACCCGTGGATTTAAACGGTA AACAT-CACAAGTTAGGGTCTCAGGGACTGAGAGGAGCG-CATTTTTA-3' (SEQ ID NO 45) were synthesized by AITbiotech (Singapore).

nicking enzyme and ELAN method. Fw-shGFP 5'-TTAG-GAGTTTTCTCCTAAGCGAATTCATATTTG-CATGTCGCTATGT-3' (SEQ ID NO 46), Rv-shGFP 5'-TTAGGTCTTTTGACCTAAGCCTCGAGAAAAAG CTGACCCTGAA-3' (SEQ ID NO 47), Fw-linear 5'-TTAG-GAGTTTTCTCCTAAGCCTAGAACTAGTG-GATCCCCGGG-3' (SEQ ID NO 48), Rv-linear 5'-TTAGGTCTTTTGACCTAAGCCTCGAGGTCGA CGGTATCGA-3' (SEQ ID NO 49), Fw-$2^{nd}$ 5'-pTTAG-GAGTTTTCTCCTAAGC-3' (SEQ ID NO 50) and Rv-$2^{nd}$ 5'-pTTAGGTCTTTTGACCTAAGC-3' (SEQ ID NO 51), Rv-21-A1 5'-pTTAGGTCTTTTGACCTAAGCAAAAAA-GACTGATGTTGACTGTTGAATCTCATGGCAGG GAAAGAGTGGTCTCATACAGAACT-3' (SEQ ID NO 52), Rv-21-A2 5'-pT-TAGGTCTTTTGACCTAAGCAAAAA-GATGTTGACTGTTGAATCTCATGGCAACACCGG GAAAGAGTGGTCTCATACAGAACT-3' (SEQ ID NO 53), Rv-21-A3 5'-pT-TAGGTCTTTTGACCTAAGCAAAAACGGGTAGCT-TATCAGACTGATGTTGACTGTTGAA TGGGAA-3' (SEQ ID NO 54), Rv-21-A4 5'-pT-TAGGTCTTTTGACCTAAGCAAAAACT-GATGTTGACTGTTGAATCTCATGGCAACACCAGGG- GAAAGAGTGGTCTCATACAGAACT-3' (SEQ ID NO 55) and loop-primers for the ELAN method L1 5'-AAT-TGTCCAGTTTTCTGGAC-3' (SEQ ID NO 56) and L2 5'-TCGACAGGTCTTTTGACCTG-3' (SEQ ID NO 57) were synthesized by AITbiotech.

Primers and probes for qPCR detection were synthesised by AITbiotech. Stem-loop primer for reverse transcription of the luciferase-targeting shRNA was 5'-GTCGTATCCAGTGCAGGGTCCGAGGTAT-TCGCACTGGATACGACAAGAGC-3' (SEQ ID NO 58), universal Taqman probe was FAM-5'-TCGCACTGGA-TACG-3'-MGB (SEQ ID NO 59), qPCR forward primer for shlucRNA was 5'-GAGCTGTTTCTGAGGAGCCTTC-3' (SEQ ID NO 60), qPCR universal reverse primer for shlu-cRNA was 5'-GTGCAGGGTCCGAGGT-3' (SEQ ID NO 61). Taqman probe for mH1 promoter was FAM-5'-TCTGG-GAAATCACCATAAA-3'-BHQ-1 (SEQ ID NO 62), qPCR forward and reverse primers for mH1 promoter were 5'-TT-CATATTTGCATGTCGCTATGTG-3' (SEQ ID NO 63) and 5'-TCCCAAATCCAAAGACATTTCA-3' (SEQ ID NO 64), respectively. qPCR forward and reverse primers for β-actin were 5'-CTGGCACCCAGCACAATG-3' (SEQ ID NO 65) and 5'-GCCGATCCACACGGAGTACT-3' (SEQ ID NO 66), respectively. Trans-splicing hybrid RNA was detected by AFP primers 5'-AAGGCATCCCTTCCTGTATGC-3' (SEQ ID NO 67), 5'-TTGCTGTGTCCCCGTGATC-3' SEQ ID NO 68 and probe FAM-5'-CCTACAAT-TCTTCTTTGGGCTGCTCGCT-3'-BHQ-1 (SEQ ID NO 69) and HSVtk primers)5'-CATCTTGCTGCAAAGCT-GAAAA-3' (SEQ ID NO 70, 5'-TTGCTGTGTCCCCGT-GATC-3' (SEQ ID NO 71) and probe FAM-5'-CCCCTGC-CATCAACACGCGTC-3'-BHQ-1 (SEQ ID NO 72).

Materials & Methods

Cell Cultivation and Transfection

Human HEK293T, HepG2, or CL48 cells were cultured in Dulbecco's Modified Eagle's Medium (DMEM) (Invitrogen) supplemented with 10% v/v heat-inactivated Fetal Bovine Serum (Hyclone) and 1% penicillin-streptomycin solution (Invitrogen). Cells were kept in humidified incubator with 5% $CO_2$, and were passaged at 80-90% confluence. All transfection assays were performed using Lipofectamine 2000 (Invitrogen) following the manufacturer's recommendations.

Cloning of Plasmids

The 227 bp human H1 promoter of the pSuper™ (Oligoengine) cloning vector was replaced by the 99 bp minimal H1 (mH1) promoter (5). Therefore, both DNA strands resembling the mH1 sequence were chemically synthesized, annealed, purified, and inserted into the pSuper plasmid using EcoRI and BglII restriction sites to generate plasmid pSuper-mH1. The expression cassette for a firefly luciferase-targeting small hairpin RNA was cloned into the pSuper-mH1 vector. Therefore, oligodeoxyribonucleotides shR-luc-plus and shR-luc-minus were annealed and inserted into pSuper-mH1 using the BglII and XhoI restriction sites to generate plasmid pSuper-mH1-shR-luc. Similarly, oligodeoxyribonucleotides shR-gfp-plus and shR-gfp-minus were annealed and inserted into pSuper-mH1 using the BglII and XhoI restriction sites to generate plasmid pSuper-mH1-shR-gfp.

To generate the hsa-miR-125b expression plasmid pSuper-mH1-miR-125b, the miR-125b precursor gene was PCR amplified from chemically synthesized oligonucleotide template using primers Fw-pre-miR-125b and Rv-pre-miR-125b and inserted into pSuper-mH1 using the BglII and HindIII sites. The 72 bp minimal SV40 enhancer sequence was synthesized by gene synthesis (GeneArt/Applied Biosystems, Regensburg) and the 237 bp full-length SV40 enhancer was amplified by PCR form plasmid pGL3-Control (Promega, Madison, Wis.) using primers Fw-SV40 and Rv-SV40. Both enhancers were cloned into pSuper-mH1-miR-125b using the SacI and EcoRI sites to generate plasmids pSuper-mH1-miR-125b-mEnh and pSuper-mH1-miR-125b-fEnh. To generate hsa-miR-125b and hsa-miR-21 luciferase reporter sensor plasmids, DNA sequences resembling three tandem repeats of the respective fully complementary miRNA binding sites BD-miR-125b-plus, BD-miR-125b-minus, BD-miR-21-plus and BD-miR-21-minus were chemically synthesized and inserted into pMIR-Report (Promega, Madison, Wis.) using the SacI and HindIII sites.

Firefly luciferase expression vectors were generated from plasmid pGL3-Control (Promega, Madison, Wis.) which also harbours the full length SV40 enhancer. The 132 bp chimeric human β-globin mini-intron was synthesized by gene synthesis (GeneArt/Applied Biosystems, Regensburg) and inserted into pGL3-Control using the HindIII and NcoI sites to generate plasmid p-int-luc-enh. SV40 enhancer-negative plasmids p-luc or p-int-luc were generated from plasmids pGL3-Control or p-int-luc-enh by deleting the SV40 enhancer. Therefore these plasmids were cleaved with XbaI and BamHI and the vector backbones were ligated.

Taq DNA polymerase, pfu DNA polymerase, restriction enzymes, T4 DNA ligase, and T7 DNA polymerase, if not specified otherwise, were purchased from Life technologies (Singapore).

Dumbbell Vector Generation gpPCR method. To generate the template for gap-primer PCR, pSuper-mH1-shR-luc was cleaved with restriction endonucleases KpnI and BamHI. Gap-primer PCR (gpPCR) was performed in a volume of 400 µl using 400 ng pSuper-mH1-shR-luc/KpnI/BamHI template, 0.2 mM of each dNTP, 0.3 µM of forward primer, 0.1 µM reverse primer, and mixture containing 8 U Taq DNA polymerase and 4 U Pfu DNA polymerase. PCR cycling was done as follows: initial denaturing at 95° C. (3 min), then 30 cycles of denaturing at 95° C. (30 s), primer annealing at 53° C. (hp-primers) or 66° C. (loop-primers) (30 s), and extension at 72° C. (30 s), and final extension at 72° C. (5 min). gpPCR products were converted into dumbbells by ligation. All the PCR products were purified by QIAquick PCR Purification Kit (Qiagen). Each 1 µg of gpPCR product was ligated as follows: AP1-hp products using 10 U T4 DNA ligase (Fermentas), AP3-hp with 20 U T4 DNA ligase, and AP1-loop products with 417 U CircLigase (Epicentre). Ligation with T4 DNA ligase was performed for 15 h at 22° C., ligation with CircLigase for 4 h at 60° C. For exonuclease treatment, 10 U T7 DNA polymerase was added per µg PCR product and the reaction was incubated for 30 min at 37° C.

Generation of hairpin template-transcribing dumbbells. To produce hairpin template-transcribing db-vectors, the minimal human H1 promoter (mH1) was PCR amplified using pSuper-mH1-shR-luc template, 5'-phosphorylated primer Fw-Bpu-mH1 introducing a Nb.Bpu10I site and primer Rv-BamHI-mH1-pA introducing a BamHI site at 5' and 3' end, respectively. The PCR product was then cleaved using Nb.Bpu10I and BamHI and incubated at 37° C. for 4 hrs to release the oligonucleotide resulting from Nb.Bpu10I cleavage in the presence of neutralizing oligonucleotide to avoid reannealing before oligonucleotides were removed using a PCR purification kit (QIAgen). T4 DNA ligase was used to ligate the phosphorylated Nb.Bpu10I 5'-overhang to the recessive 3'-hydroxyl group to form one loop of the dumbbell and to ligate a 5' phosphorylated DNA hairpin structure comprising a BglII overhang to the compatible BamHI sticky end to covalently close the dumbbell from the other side. DNA hairpin hp-s/as, hp-miR-s/as, hp-iPT-s/as, hp-iPT-as/s, hp-125b were used to generate db-iPR-hp-s/as, db-iPR-miR-hp-s/as, db-iPTR-hp-s/as, db-iPTR-hp-as/s, and db-hairpin-miR-125b, respectively. Ligation was performed in the presence of BamHI and BglII to suppress the formation of alternative dumbbells. Resulting dumbbells were subjected to T7 DNA polymerase (Fermentas, Thermo Scientific) treatment to destroy unligated and misligated by-products.

Nicking enzyme method. For nicking-enzyme-based production we followed the protocol described by Taki et al. performing two rounds of PCR (6,7). Linear shRNA- (egfp- and luciferase-targeting), miRNA-, and miRNA-21 antagonist-expressing dumbbells were produced using this method. To produce the egfp-targeting dumbbell db-Nick, luciferase-targeting shRNA expressing dumbbell db-iPR-linear-s/as, or the miR-125b-1-expressing dumbbell db-linear-miR-125b, double-digested pSuper-mH1-shR-GFP, pSuper-mH1-shR-luc, or pSuper-mH1-miR-125b plasmid was used as the PCR template, respectively, the sequences of forward and reverse primers for the first PCR reaction were Fw-shGFP and Rv-shGFP for db-Nick, Fw-linear and Rv-linear for db-iPR-linear-s/as and db-linear-miR-125b. The sense and antisense primer sequences for the second PCR reaction were Fw-$2^{nd}$ and Rv-$2^{nd}$, respectively.

To produce the miR-21-targeting miR-21 antagonist-expressing dumbbells db-anti-miR-21-A1/2/3/4, mH1 promoter was amplified using primers Fw-Bpu-mH1 and Rv-21-A1/Rv-21-A2/Rv-21-A3/Rv-21-A4. The miR-21 antagonist sequences were introduced by the reverse primers used. Exonuclease treatment was done as described above.

ELAN method. For ELAN-based production of dumbbell db-ELAN we followed the protocol by Cost et al. (8). 2000 ng PCR product was digested with each 2 U FD XhoI and FD EcoRI and each 25 pmol of the loop-sequences L1 and L2 were ligated using 10 U of T4 DNA ligase in the presence of 0.5 U of FD XhoI, FD EcoRI, FD SalI, and FD MfeI. Exonuclease treatment was done as described above.

Knockdown Assay

To monitor firefly luciferase target gene knockdown, HEK293T cells were co-transfected with luciferase reporter vector pGL3 (Promega) or the respective miRNA-sensor vectors and the respective small RNA expressing dumbbell or plasmid. To investigate gpPCR-generated dumbbells, 90 ng luciferase reporter vector pGL3 (Promega) and either 90 ng dumbbell or plasmid DNA (equimass) or 0.5 pmol of dumbbell or plasmid DNA (equimolar; pVAX1 plasmid was used as top-up DNA for dumbbell transfection) using Lipofectamine 2000 (Life Technologies) and luciferase knockdown was monitored 48 h post transfection. To investigate luciferase-targeting shRNA-expressing dumbbells, miR-125b-1-expressing dumbbells, and miR-21 antagonist-expressing dumbbells, HEK293T or HepG2 cells seeded in 24-wells were co-transfected with 250 ng reporter or sensor plasmid and specified amounts of dumbbell or plasmid.

RNA Extraction, Reverse Transcription, and qPCR Detection

To investigate the kinetics of transcription of the luciferase-targeting shRNA, $5 \times 10^5$ cells were transfected with 1 pmol of either a db-vector (linear or hairpin designs) or plasmid pSuper-mH1-shR-Luc. 10 min, 1 h, 6 h, and 24 h post transfection total RNA was isolated using Trizol. (Life Technologies) following the manufacturers protocol and shRNA transcripts were quantified using the universal TaqMan-based RT-PCR protocol (4), and the fold change was determined by ΔΔCt quantification using β-actin RNA as an internal standard.

To compare the efficiency of trans-splicing between plasmid and dumbbell vectors, $2 \times 10^5$ HepG2 cells were transfected in equimass and equimolar amounts with the 3'ER trans-splicing RNA dumbbell vector overexpressed with AFP mini gene plasmid using Lipofectamine 2000 reagent (Life Technologies). The 3'ER trans-splicing RNA plasmid overexpressed with AFP mini gene transfected equimass was used as a comparing control. The total amount of DNA transfected was 1000 ng and empty pVAX1 vector was used to top up to the final concentration (in case of equimolar). RNA was extracted 24 hours post-transfection using RNeasy plus mini kit (Qiagen) following manufacturer's protocol. 500 ng of total RNA was converted into cDNA with random primers using SuperScript III Reverse Transcriptase (Life Technologies). For real time RT-PCR, 25 ng of cDNA was amplified using the AFP and HSV-tk primer/probes. The fold change was determined by ΔΔCt quantification using β-actin RNA as an internal standard.

To investigate the transcriptional activity of gpPCR-generated dumbbells, $10^5$ HepG2 cells were transfected with 0.25 pmol of dumbbell or plasmid DNA using Lipofectamine 2000. pVAX1 plasmid was used as control as well as a top-up DNA for dumbbell transfection. 24 h post transfection, cells were harvested and total RNA was isolated using Trizol. (Life Technologies) following the manufacturers protocol. Luciferase-targeting shRNA (shluc) was detected using the universal TaqMan-based RT-PCR protocol (4), and the fold change was determined by ΔΔCt quantification using β-actin RNA as an internal standard. All real-time PCR reactions were performed using 1×TaqMan Universal PCR Master Mix (Applied Biosystems) following the manufacturer's instructions using the 7900HT Fast real-time PCR system (Applied Biosystems).

Nuclear Import Assay

To investigate the nuclear import of different vectors, $5 \times 10^5$ HepG2 cells were seeded in 6-well plates and transfected with 1 pmol of dumbbell or plasmid DNA using Lipofectamine 2000. pVAX1 plasmid was used as control as well as a top-up DNA for dumbbell transfection. 24 h post transfection, cells were harvested, washed twice with cold PBS, incubated in hypotonic buffer (20 mM Tris-Cl, pH 7.4, 10 mM NaCl, 3 mM $MgCl_2$) for 15 min on ice, and lysed by 20 times dounce homogenization in hypotonic buffer. After centrifugation at 3,000 rpm for 10 min at 4° C., the supernatant (cytoplasmic fraction) was subsequently removed and the pellet (nuclear fraction) was further lysed by four freeze-thaw cycles using liquid nitrogen and a water bath. Lysed nuclei were centrifuged for 30 min at the maximum speed at 4° C. Total nuclear nucleic acids were extracted from the supernatant using Trizol and the absolute abundance of transfected vector DNA was determined by TaqMan qPCR quantification of the copy number of the minimal H1 promoter sequence using the 7900HT Fast realtime PCR system (Applied Biosystems). For qPCR quantification, respective rtPCR standard curves were used to measure db-AP1-hp, db-ELAN, and the supercoiled plasmid DNA.

Capillary Gel Electrophoresis

High-resolution capillary electrophoresis was performed using a QIAxcel® DNA high-resolution gel cartridge (Qiagen) on a QIAxcel system (Qiagen) according to the manufacturer's instructions. QX DNA Size Marker pUC18/HaeIII (Qiagen) was used to determine dumbbell vector size using 5 ng/μl QX Alignment Marker 15 bp/1 kb (Qiagen) as internal standard. The OL800 method was used for analysis.

Multiple Cloning Site Insertion into CRISPR Plasmids

This study used the pX330-U6-Chimeric_BB-CBh-hSp-Cas9 ('pX330'; Addgene plasmid #42330) and the pX335-U6-Chimeric_BB-CBh-hSpCas9n(D10A) ('pX335'; Addgene plasmid #42335) plasmids (9) as expression platforms for the type II CRISPR gene editing system. pX330 encodes the type II CRISPR system with wild-type Cas9, while pX335 encodes the type II CRISPR system with the ΔHNH Cas9 nickase (Cas9n), which carries the D10A amino acid change.

Figure 5:
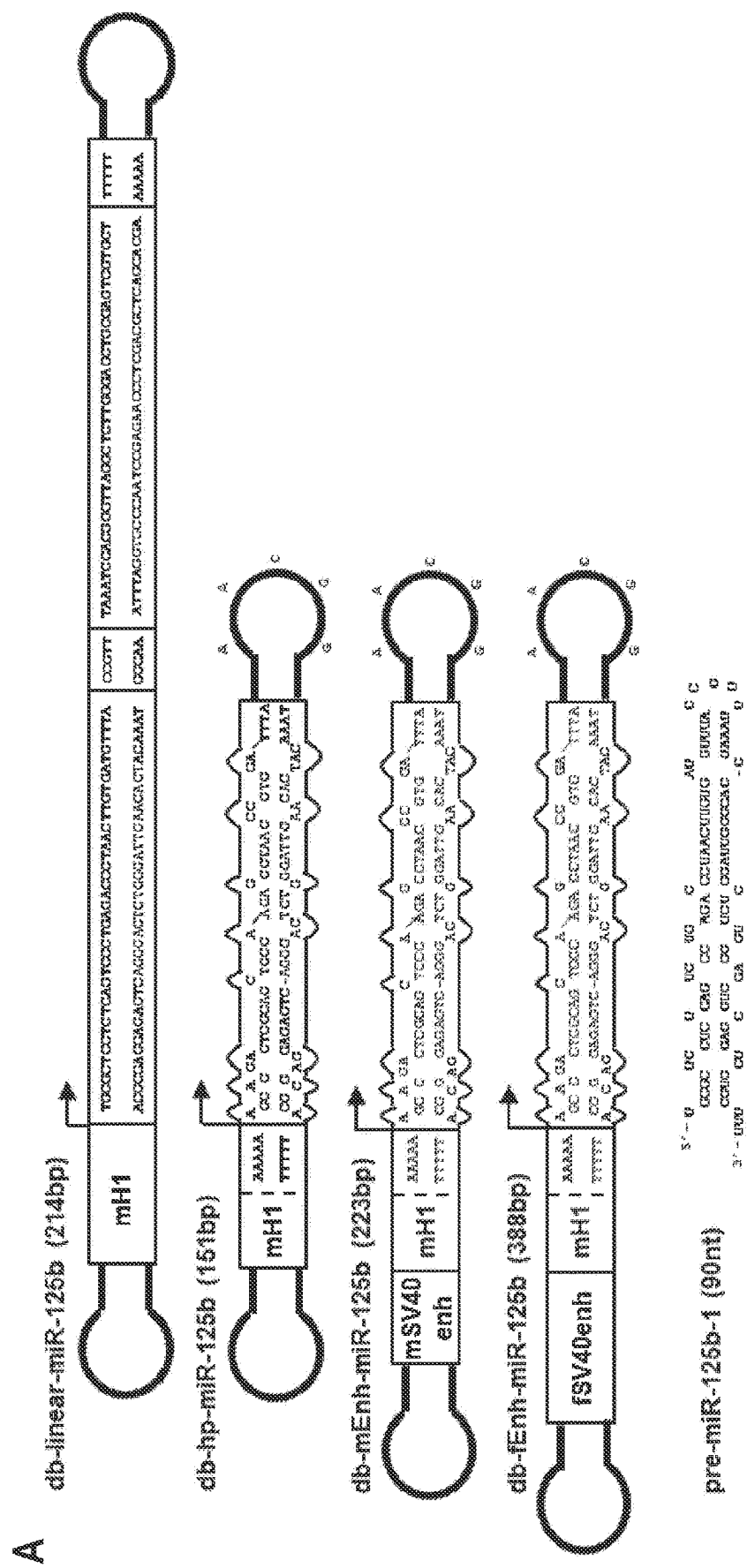
FIG. 5: Knock-down of firefly luciferase-miR-125b sensor reporter gene expression triggered by hsa-miR-125b-expressing dumbbells. A, Design of dumbbell db-linear-miR-125b (SEQ ID NO 82 and SEQ ID NO 83) harbouring a linear miR-125b expression cassette and the minimised dumbbell db-hairpin-miR-125b (SEQ ID NO 84) equipped with a hairpin miR-125b transcription template. db-mEnh-miR-125b: dumbbell (SEQ ID NO 85) harbouring the 72 bp minimal SV40 enhancer; db-fEnh-miR-125b: dumbbell (SEQ ID NO 86) including the 237 bp full length SV40 enhancer. Sequences coding for mature miR-125b (red) and miR-125b* (blue) are highlighted and the resulting pre-miR125b-1 RNA sequence (SEQ ID NO 87) and secondary structure is indicated. B, Sensing of plasmid vs. dumbbell-driven miR-125b overexpression in HepG2 cells. Cells were transfected in 24-wells with 250 ng sensor plasmid alone or together (+) with 250 ng miR-125b expressing dumbbells or plasmid. Dumbbell db-hairpin-miR-125b was generated either using the conventional method (ELAN) or our (New) protocol. HEK293T (C) or CL48 (D) cells seeded in 24-wells were (co-)transfected either with 100 ng pMIR-125b-Sensor alone or together with 100 ng db-hairpin-miR-125b (New) (no feeder used for this). (B) to (D), Luciferase knockdown was monitored 48 h post transfection. Error bars indicate mean deviations from average of three independent experiments. E, Knockdown of luciferase-miR-125b sensor reporter gene expression by miR-125b overexpressed from different dumbbells in HepG2 cells. Cells seeded in 24-wells were (co-)transfected with 100 ng pMIR-125b-Sensor alone or together with 1.5 pmol dumbbell DNA (feeder pUC119) and luciferase knockdown was monitored 48 h post transfection. Error bars indicate mean deviations from average of four independent experiments. Significance was tested using one-way ANOVA with Newman-Keuls post hoc test.
Figure 5:
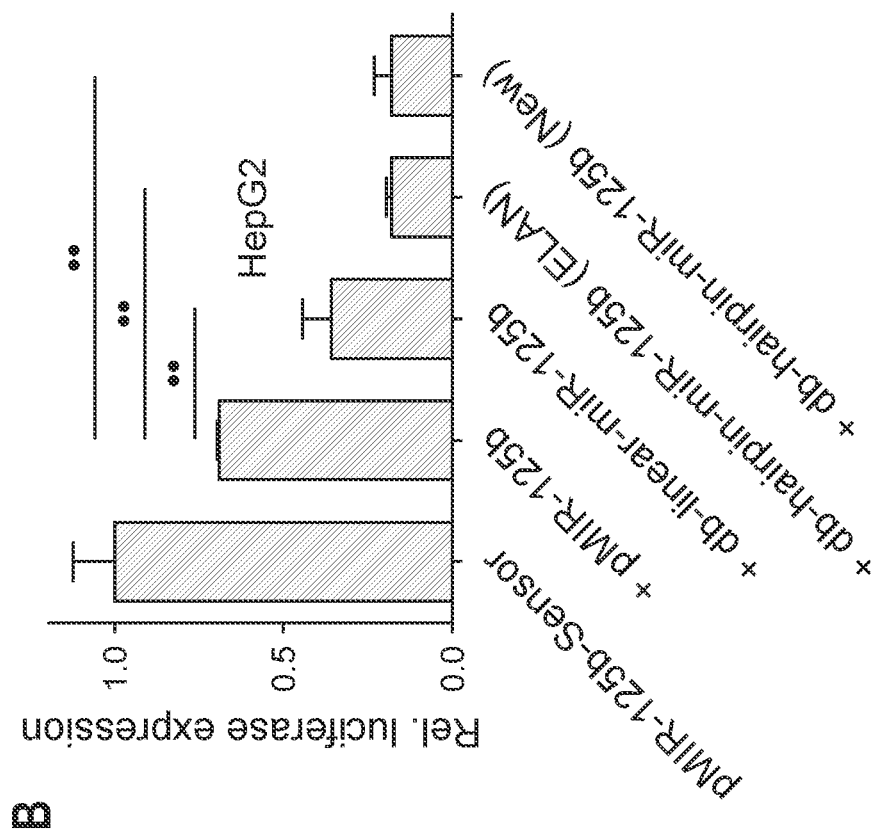
Figure 5:
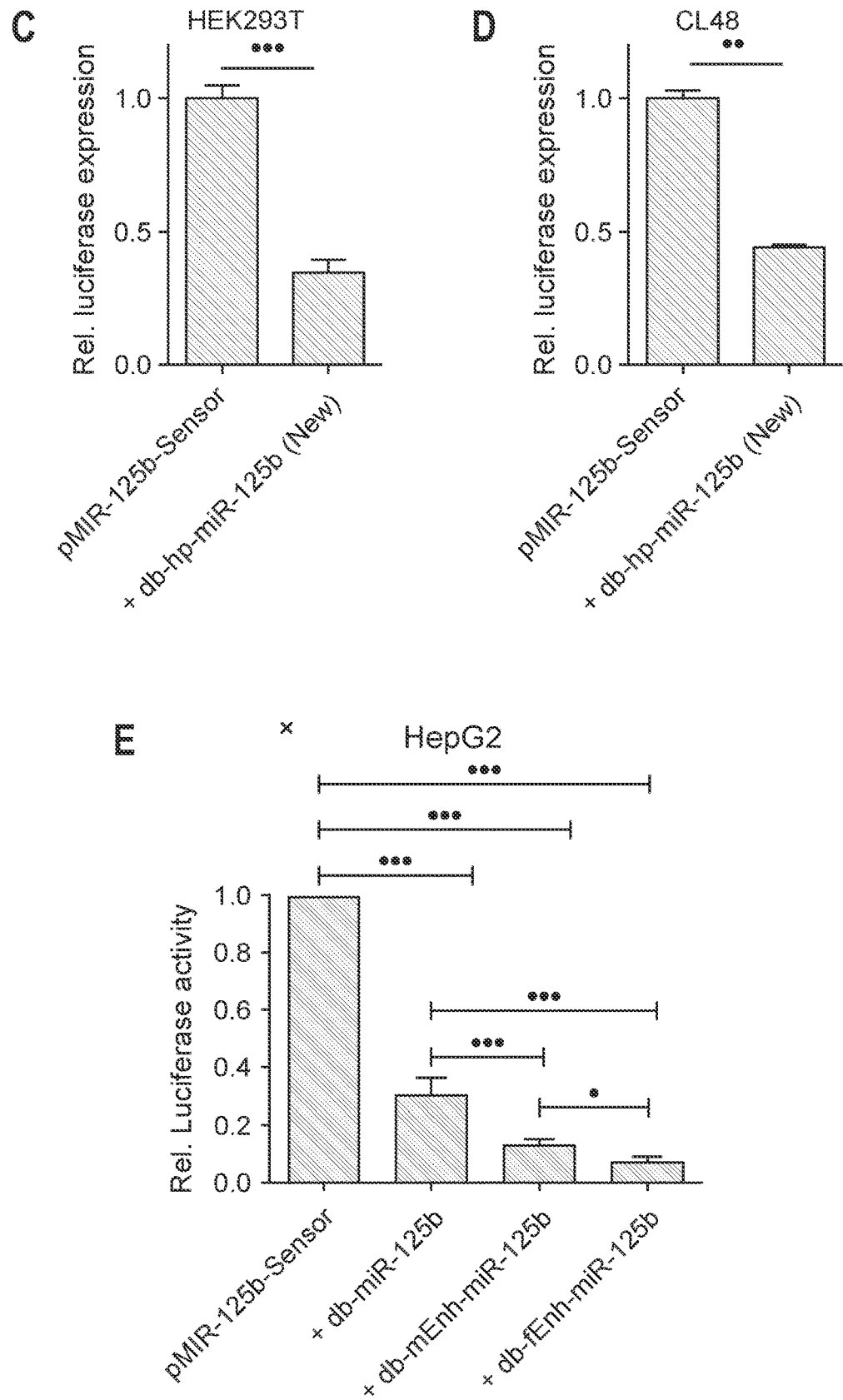

To facilitate dumbbell vector construction from pX330 and pX335, suitable restriction sites were required which separate the necessary components, such as the Cas9/Cas9n and sgRNA expression cassettes, from the components which would be excluded from the dumbbell vectors, such as the ampicillin resistance gene and long non-coding regions on the plasmid backbone. Existing restriction sites on pX330 and pX335 were assessed based on restriction enzyme availability, and the compatibility of their sticky ends for dumbbell loop ligation. Due to the absence of suitable restriction sites, a multiple cloning site bearing the XhoI, NheI and HindIII restriction sites was inserted into the existing PscI restriction site on pX330 and pX335. To introduce this multiple cloning site, an equimolar mixture of a pair of single-stranded DNA oligonucleotides (ssODN) (sense: 5'-CATGCTCGAGGCTAGCAAGCTT-3' (SEQ ID NO 118); antisense: 5'-CATGAAGCTTGCTAGCCTCGAG-3' (SEQ ID NO 119)) was annealed by incubation at 95° C. for 5 min, then placed on the bench to cool gradually to room temperature. 5'-OH phosphorylation was carried out using T4 Polynucleotide Kinase (PNK) (Thermo Scientific), to give a double-stranded DNA fragment with the respective restriction sites as well as PscI sticky ends. The pX330 and pX335 plasmids were digested with PscI (PciI) (Thermo Scientific), and the fragment ligated with T4 DNA Ligase (Thermo Scientific). The same approach was then used to introduce a second multiple cloning site bearing the BamHI, BsrGI and MluI restriction sites (ssODNs: sense: 5'-GGCCACGCGTTGTA-CAGGATCC-3' (SEQ ID NO 120); antisense: 5'-GGCCG-GATCCTGTACAACGCGT-3' (SEQ ID NO 121)) into the existing NotI restriction site on pX330 and pX335. FIG. 5 shows simplified plasmid maps of pX330 and pX335 with the multiple cloning sites ('pX330-MCS' and 'pX335-MCS' respectively).

Ligation products were used to transform chemically competent *Escherichia coli* strain DH5a. Cryostocks (−80° C.) of *E. coli* DH5a were thawed on ice, and added to 1.5 mL microcentrifuge tubes containing 10 μL of ligation product using pre-cooled pipette tips. Tubes were kept on ice for one hour, then subjected to heat shock at 42° C. for 90 seconds, and then immediately returned to ice for five minutes. To each tube, 1 mL of LB broth was added and tubes incubated at 37° C. for one hour with shaking. Bacteria were pelleted at 3,000 rpm and resuspended in 50 μL of LB broth. Suspensions were plated on LB agar plates with 100 μg/mL ampicillin and incubated overnight at 37° C. Viable transformants were screened for successful multiple cloning site insertion using colony PCR with recombinant Taq DNA polymerase (Thermo Scientific) and capillary electrophoresis sequencing (AITbiotech).

Design and Sub-Cloning of Guide Sequences

Possible gRNA target sites terminate in a protospacer adjacent motif (PAM) sequence. The *S. pyogenes*-derived CRISPR system used in this study recognizes target sites terminating in 5'-NGG-3' PAMs (beginning in 5'-CCN-3' for targets on the antisense strand) (9). Four candidate 20-nucleotide genomic target sites terminating in NGG or beginning with CCN were identified in close proximity to (within 50 bases of) the G6PD-Mahidol point mutation on exon 6. A universal negative guide sequence was also designed (adapted from Sigma-Aldrich), which when cloned into the CRISPR expression vectors, would also be transcribed into a sgRNA which folds the appropriate secondary structure and lacks predicted targets in the human genome (based on sequence alignments). This was required as a more suitable negative control as compared to an empty vector, since empty vectors not containing any guide sequence would not be transcribed into appropriately-folded sgRNAs capable of binding the Cas9/Cas9n endonucleases. Empty vectors are therefore unsuitable to control for Cas9/Cas9n activity in the absence of a target-complementary guide sequence.

TABLE gRNA candidates, including universal negative guide sequence. Only 20 nt target-complementary guide sequences are shown.

| Guide sequence | Target-complementary sequence |
|---|---|
| 4 (SEQ ID NO. 108) | 5'-TACCCCCTTGAACCCCTCTT-3' |
| 16 (SEQ ID NO. 109) | 5'-GATGCGGTTCCAGCTTCTGC-3' |
| 17 (SEQ ID NO. 110) | 5'-TCCGGGCTCCCAGCAGAAGC-3' |
| 20 (SEQ ID NO. 111) | 5'-CTCTGCAGGTCCCTCCCGAA-3' |
| Universal negative (SEQ ID NO. 112) | 5'-CGCTACCAGAGCTAACTCA-3' |

Guide sequence and their respective complementary (antisense) ssODNs were designed with 5'-CACCGN . . . N-3' and 3'-CN . . . NCAAA-5' ends respectively to give rise to 5'-CACC and 5'-AAAC overhangs to facilitate cloning into the existing BbsI restriction site of pX330 and pX335. Equimolar mixtures of guide and complementary ssODNs were annealed and phosphorylated with T4 PNK (Thermo Scientific). pX330-MCS and pX335-MCS plasmids were digested with FastDigest BbsI (Thermo Scientific), generating compatible overhangs for guide sequence ligation, then dephosphorylated with FastAP (Thermo Scientific). Ligation was carried out at 22° C. for 4 hours in 20 µL reaction mixtures containing 1 U of T4 DNA Ligase (Thermo Scientific), and the insert and vector at a 5:1 molar ratio.

10 µL of each ligation product was used to transform chemically competent E. coli strain DH5a, plated on LB agar plates with 100 µg/mL ampicillin and incubated overnight at 37° C., and viable colonies subject to colony PCR screening. Colony PCR was performed with 0.5 µM of a universal forward primer binding a region on the U6 promoter (5'-CGATACAAGGCTGTTAGAGAGATAATGG-3' (SEQ ID NO 122)), and 0.5 µM of the respective guide sequence antisense ssODNs as reverse primers. PCR conditions were as follows: 95° C., 10 min; 27 cycles of 95° C. 30 sec, 54° C. 30 sec, 72° C. 1 min; and final extension at 72° C. for 10 min. Colony PCR products were analyzed on 1% agarose gel stained with ethidium bromide.

Generation of Donor Template Oligonucleotides

Two G6PD wild-type donors were generated, one with approximately 50-nucleotide homology arms flanking the site of editing ('short donor'), and another with approximately 200-nucleotide homology arms ('long donor'). The donors were generated using high-fidelity PCR amplification from genomic DNA of cells from a healthy individual, using 1 U of Pfu DNA polymerase (Thermo Scientific) and 0.5 µM of each primer (short donor forward primer: 5'-TGCAGCTCTGATCCTCACTCC-3' (SEQ ID NO 123); short donor reverse primer: 5'-TGGACAGCCGGTCAGAGC-3 (SEQ ID NO 124)'; long donor forward primer: 5'-AAAAGGACGCGTGCCAGCAATGCCACCC-3' (SEQ ID NO 125); long donor reverse primer: 5'-AATATTGGATCCGGCTCCTGAGTACCACC-3' (SEQ ID NO 126)) under the following conditions: 95° C., 5 min; 30 cycles of 95° C. 30 sec, 55° C. 30 sec, 72° C. 1 min; and final extension at 72° C. for 7 min. Capillary electrophoresis sequencing (AITbiotech) was used to ensure that the donors carried segments of the wild-type sequence.

A G6PD-Mahidol donor ('mutant donor'), bearing the G6PD-Mahidol point mutation, was generated using primer extension site-directed mutagenesis, using the wild-type short donor as a template and a pair of mutagenic primers bearing the mutation close to their 5' ends (Mutagenesis primer 1: 5'-TCCAGCTTCTGCTGGGAGC-3' (SEQ ID NO 127); mutagenesis primer 2: 5'-GAAGCTGGAACCGCATCATC-3' (SEQ ID NO 128); mutation site in bold). In the first PCR, mutagenesis primer 1 was paired with the short donor forward primer, and mutagenesis primer 2 with the short donor reverse primer. PCR was performed using 0.5 U of Taq DNA polymerase (Thermo Scientific) and 0.5 µM of each primer, under the following conditions: 95° C., 5 min; 25 cycles of 95° C. 30 sec, 55° C. 30 sec, 72° C. 45 sec; and final extension at 72° C. for 10 min. The 75 bp bands on 1% agarose gel were excised and extracted using a GeneJET Gel Extraction Kit (Thermo Scientific). Both fragments were added to a single, second PCR mixture containing 1 U Pfu DNA polymerase (Thermo Scientific) and 0.5 µM each of the short donor primer pair, to generate the mutant donor. The reaction mixture was first incubated on a heat block at 95° C. for 5 min, then placed on the bench to cool to room temperature. Once cooled, the mixture was returned immediately to the heat block at 72° C. and incubated for 1 min, then placed into the thermal cycler configured as such: 30 cycles of 95° C. 30 sec, 55° C. 30 sec, 72° C. 30 sec; and final extension at 72° C. for 7 min. An aliquot of the PCR product was analyzed on 1% agarose gel stained with ethidium bromide. Capillary electrophoresis sequencing (AITbiotech) was used to verify successful site-directed mutagenesis of the donor.

Production of Minimal-Sized CRISPR Dumbbell Vectors by ELAN Loop Ligation

Figure 7:
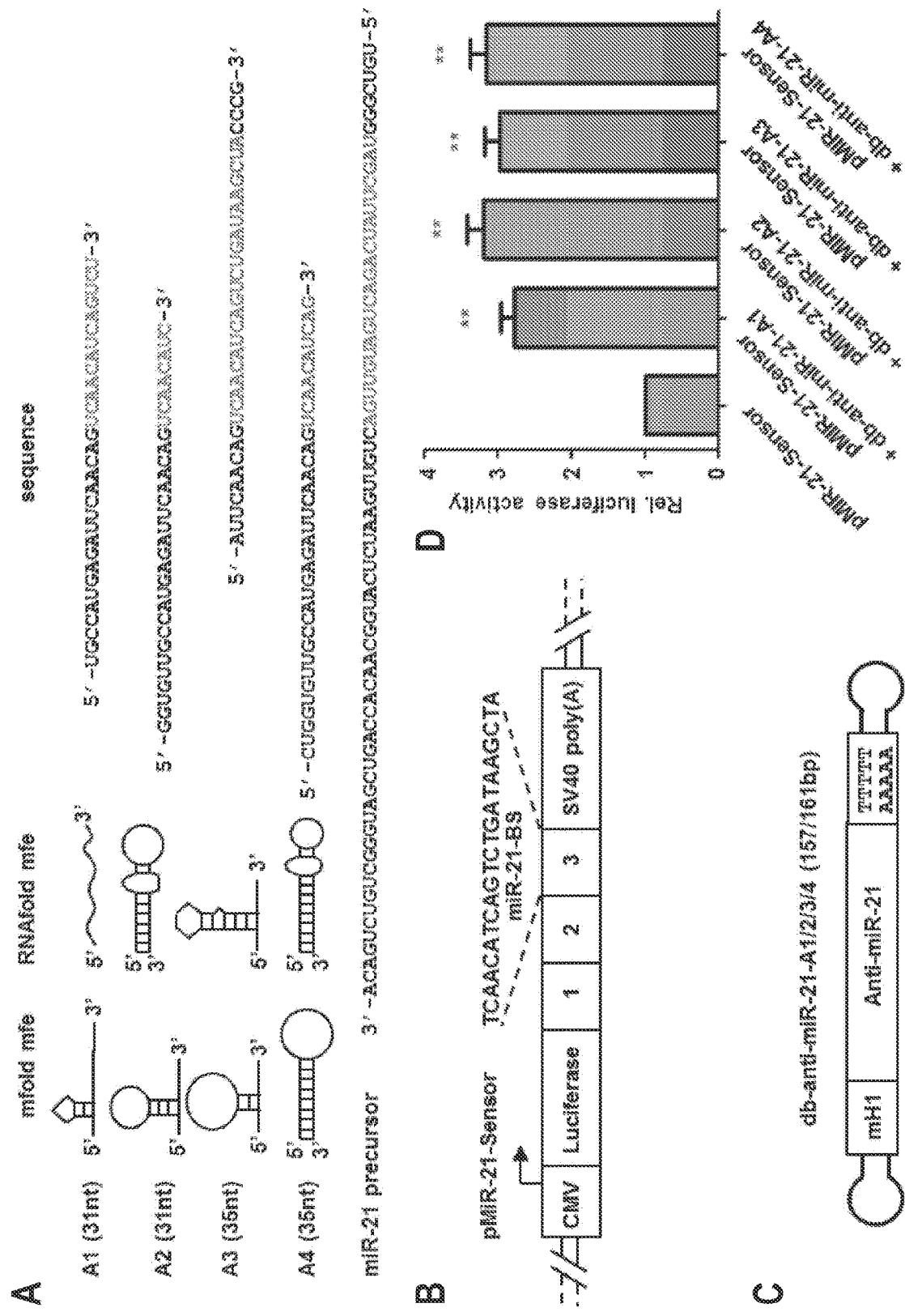
FIG. 7: Functional knockdown of hsa-miR-21 by antisense-miR-21 (anti-miR-21) expressing dumbbell vectors in CL48 cells. A, Sequences and minimum free energy RNA secondary structures of miR-21-targeting antisense RNAs (A1: SEQ ID NO 92, A2: SEQ ID NO 93, A3: SEQ ID NO 94 and A4: SEQ ID NO 95) as predicted by mfold and RNAfold and positioning relative to the miR-21 precursor (SEQ ID NO 113). B, Design of the miR-21 sensing luciferase reporter plasmid with three fully complementary miR-21 binding sites. C, Design of anti-miR-21-A1, -A2, -A3, or -A4-expressing dumbbell vectors. D, CL48 cells seeded in 24-wells were (co-)transfected with 100 ng pMIR-21-Sensor alone or together with 100 ng anti-miR-21-expressing dumbbell vector DNA and functional miR-21 knockdown was monitored 24 h post transfection. Error bars indicate mean deviations from average of two independent experiments. Significance was tested using one-way ANOVA with Newman-Keuls post hoc test.
Figure 8:
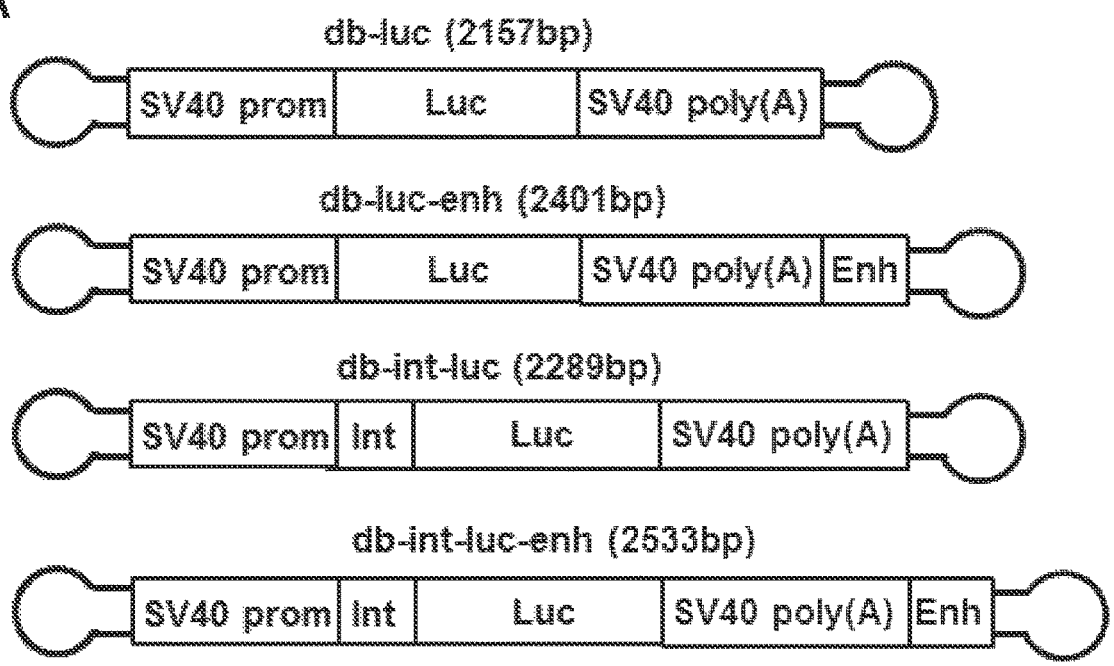
FIG. 8: Enhancement of dumbbell vs. plasmid-driven luciferase expression by the β-globin gene chimeric intron and/or the full length SV40 enhancer. A, Design of dumbbell vectors. db-luc: parental vector; db-luc-enh: SV40 enhancer dumbbell; db-int-luc: intron dumbbell; db-int-luc-enh: intron-enhancer dumbbell. Luciferase expression triggered by equimass amounts dumbbell vectors and equivalent plasmids in HEK293T (B) or HepG2 (C) cells 48 h post transfection. Error bars indicate mean deviations from average of three to five independent experiments. Significance was tested using one-way ANOVA with Newman-Keuls post hoc test.
Figure 8:
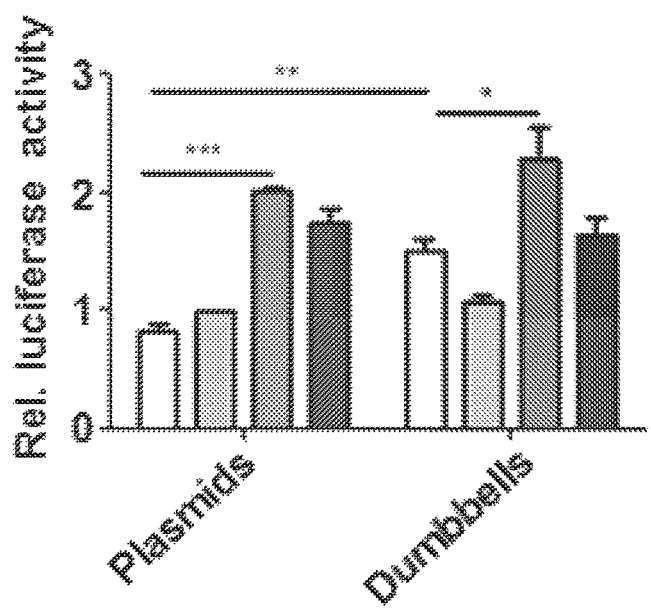
Figure 8:
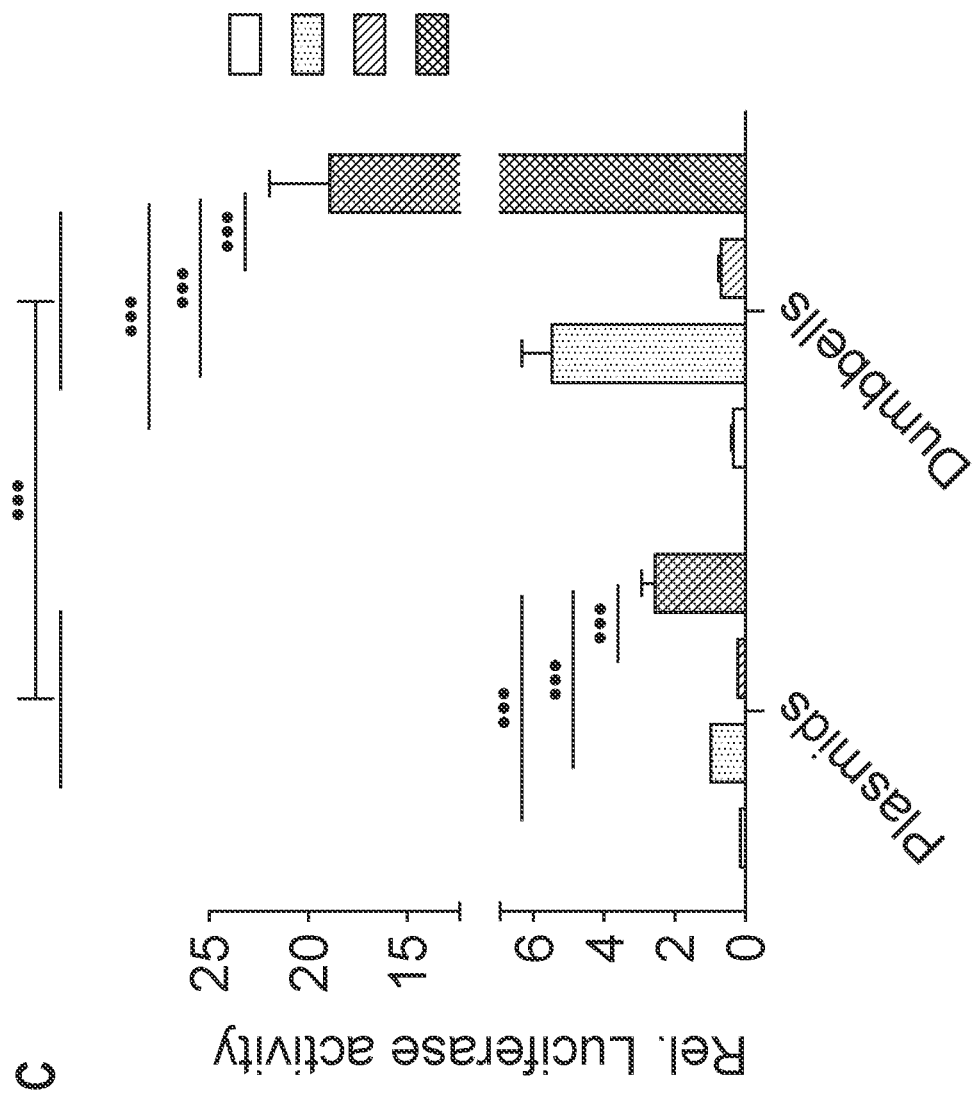

Dumbbell vectors were generated from the pX330-MCS and pX335-MCS plasmids carrying the guide sequences, using the enzymatic ligation assisted by nucleases (ELAN) method (4,7). The XhoI and MluI sites contained within the introduced multiple cloning sites were chosen to be the termini of the main double-stranded component of the dumbbells. ssODNs were designed with base sequences thermodynamically favouring the formation of hairpin loops. After hairpin formation, the loops would leave SalI (G/TCGAC) and SgsI (AscI) (GG/CGCGCC) 5' overhangs, which were compatible for ligation to the XhoI (C/TCGAG) and MluI (A/CGCGT) overhangs from digestion of the pX330-MCS/pX335-MCS plasmids at their multiple cloning sites. Loop ssODN folding predictions were obtained using mfold (10) (FIG. 7). Each correct ligation would eliminate both restriction sites, while undesired by-products such as loop dimers retaining SalI or SgsI restriction sites, or linearized plasmid dimers retaining XhoI or MluI restriction sites, would be cleaved by the respective restriction enzymes present in the reaction mixture, and therefore be susceptible to exonuclease degradation during post-treatment. A fifth restriction enzyme, EheI, was also included in each reaction mixture to cleave the unneeded plasmid backbone, also rendering it susceptible to exonuclease degradation. At completion of the reaction, desired dumbbells were exonuclease resistant, while all by-products had free DNA ends due to restriction enzyme cleavage. Reaction mixtures were cleaned up using T7 DNA Polymerase (New England Biolabs), which has strong 3'→5' exonuclease activity. A graphical summary of the loop ligation method is shown in FIG. 8, while a detailed protocol is described in Table 2.

Statistical Analysis

Results were shown as mean±S.E.M when more than one experiments were performed. Unpaired student t-test was used to determine significance when comparing two groups. For the comparison of more than two groups of data, one-way ANOVA with Newman-Keuls post hoc test was used. Prism 5 Graphpad software was used for the statistical analysis. * represents p value<0.05,  represents p value<0.01, and * represents p value<0.001.

EXAMPLE 1

Figure 2:
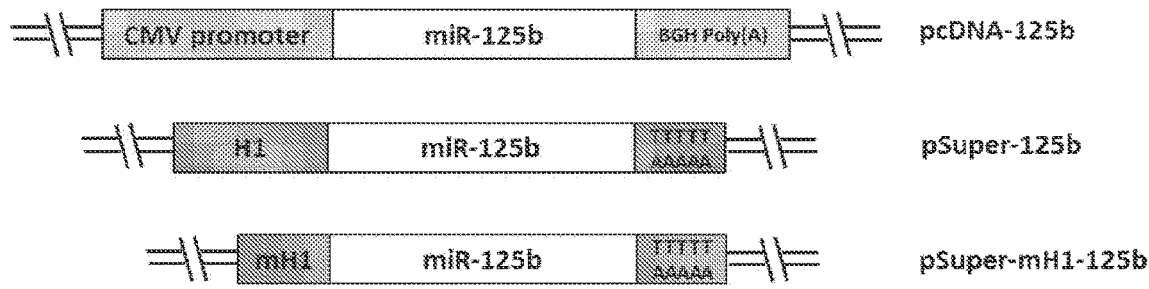
FIG. 2: Comparison of promoter strengths with regard to miR-125b expression. A, The miR-125b expression cassette was cloned into plasmid vectors pCDNA3.1 (CMV promoter), pSuper (H1 promoter) and a modified pSuper-mH1 (mH1 promoter) to generate pCDN3.1-125b, pSuper-125b, and pSuper-mH1-125b. B, $5 \times 10^5$ cells seeded in 6-well were transfected with 1000 ng miR-125b expressing vectors or the respective empty control vectors. 24 h post transfection small RNA was isolated and absolute miR-125b levels were quantified using TaqMan-probe-based rtRT-PCR (4). C, $5 \times 10^4$ cells seeded in 24-well were transfected with 300 ng miR-125b expressing vectors or the respective empty control vectors.
Figure 2:
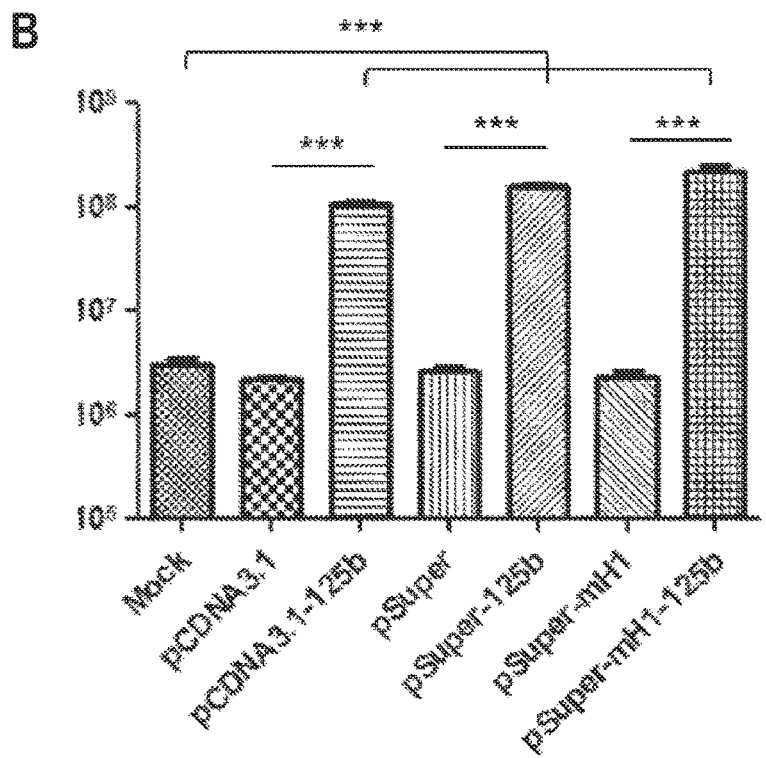
Figure 2:
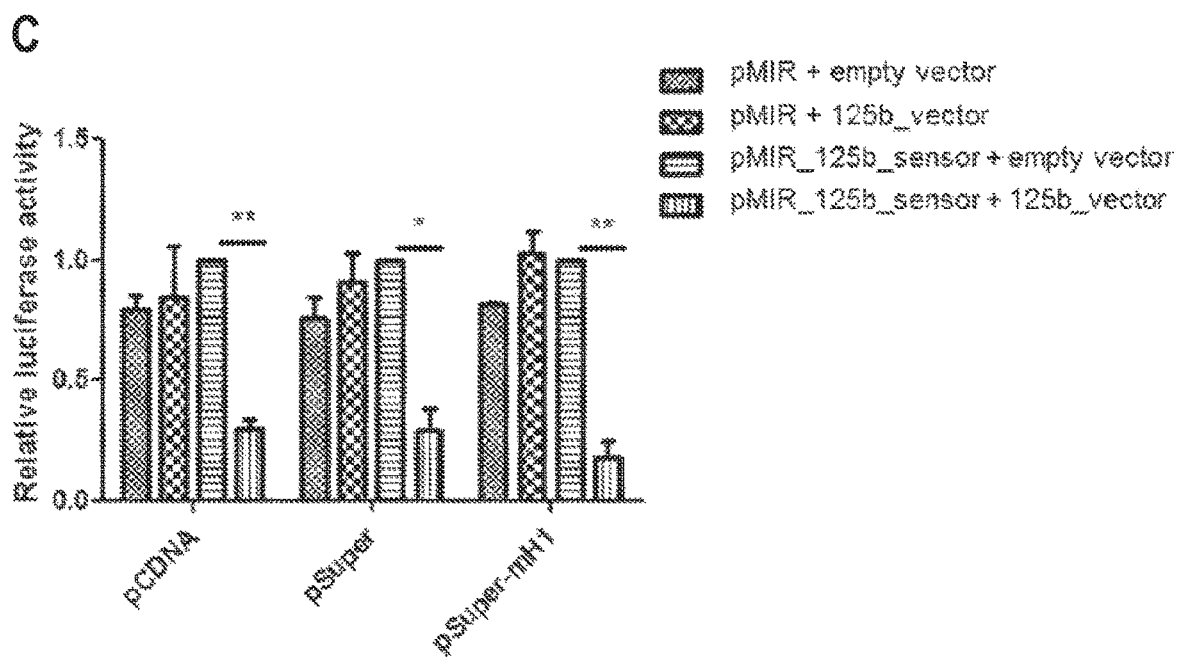

Design, Generation, and Cellular Activity of Hairpin-Template Transcribing Dumbbell Vectors for Small RNA Expression We investigated dumbbells as a safe and cheap alternative vector system to trigger transient expression of small non-coding RNAs. To capitalise on the fact that db-vectors know no lower size limit, we sought to minimise dumbbells for small RNA expression as much as possible employing three strategies: Firstly, conventional shRNA- or miRNA-expression cassettes consist of a promoter, a linear RNA-coding sequence, and a transcriptional terminator. Since shRNAs and precursor miRNAs (pre-miRNA) form hairpin structures which harbour a significant degree of self-complementarity, linear expression cassettes contain redundant sequences as the sense and antisense portions forming the stem are included in both strands of the DNA duplex. We eliminated such redundant sequences and in the minimised dumbbells, part of the db-DNA structure resembles the structure of the hairpin RNA, i.e. the duplex of the dumbbell forms the stem of the RNA and one of the terminal db-loops codes for the loop of the RNA hairpin (FIG. 1A). This design implies that RNA transcription goes around the hairpin template including the loop of the db-DNA. This strategy, to which we refer as 'hairpin template'-transcription, shortens the respective vectors by about 30 to 40 base pairs (bp) for shRNA expression or 60 bp or more for miRNA expression depending on the miRNA precursor length. Secondly, we implemented the minimal human H1 (mH1) promoter (5). This 99 bp polymerase III promoter is 128 bp shorter than the full length H1 promoter, was found to be as active or better in terms of miRNA expression compared with the full length H1 or CMV promoter (FIG. 2), and hasn't found applications in dumbbells yet. Thirdly, earlier studies suggested non-essential sequence positions at the 3' end of the H1 promoter directly upstream of the transcriptional start (5). We replaced six of these nucleotides by a restriction site and another five by an inverted polymerase III transcriptional terminator, i.e. an adenosine pentamer ($A_5$), which terminates hairpin template-transcription in the opposite strand shortening the vectors by another five base pairs (FIGS. 1A,B). Transcription of the integrated promoter/terminator element starts downstream of the inverted termination signal and its sequence is not added to the 5' end of the transcript. Together, the novel features allow reducing the size of shRNA- or miRNA-expressing dumbbells by 171 bp (57%) or 191 bp (56%) enabling the production of small RNA expressing dumbbells as short as 130 bp, the smallest genetic expression vectors reported.

We developed a novel protocol for the generation of minimised hairpin template-transcribing db-vectors (FIG. 1C). Therefore, the mH1 promoter sequence is being amplified by PCR using primers introducing upstream a Nb.Bpu10I nicking site and downstream a BamHI cleavage site. After Nb.Bpu10I/BamHI cleavage, the upstream loop is generated by intramolecular ligation of the Nb.Bpu10I 5' overhang. The small RNA coding sequence is concurrently (simultaneously) added by intermolecular ligation of a chemically synthesised oligomeric DNA hairpin structure that provides a BamHI-compatible BglII 5' overhang and that resembles the template for the transcription of the RNA precursor (FIG. 1B). Upon dumbbell formation neither (none) of the cleavage sites is reconstituted and the presence of BamHI and BglII in the ligation reaction destroys mis-ligated homo dimers shifting the equilibrium towards the correctly ligated dumbbell. Exonuclease digestion subsequently yields only the correctly ligated dumbbell. This new protocol combines features of two dumbbell production techniques that were reported earlier (6-8). However, due to the hairpin-template technology, alternative hairpin-forming oligodeoxy-ribonucleotides can be ligated to the same db-core structure to generate dumbbells for alternative targets. The conversion yields for the new protocol approximate 90% when the small DNA fragments resulting from endo-nucleolytic cleavage are functionally neutralised with a complementary sequence and/or removed prior to loop ligation (FIGS. 1C,D).

To investigate different design features of minimised hairpin-template-transcribing dumbbells, HEK293T or HepG2 cells were co-transfected with the pGL3-Control reporter plasmid and equimolar amounts of different luciferase shRNA-expressing dumbbells, and luciferase gene expression was monitored 24 h post transfection. This comparison indicates that the dumbbell equipped with the integrated promoter/terminator/restriction element (db-iPRT-hp-s/as) triggered as strong or better target gene knockdown compared with a construct harbouring separated promoter and terminator sequences (db-iPR-hp-s/as) (FIGS. 1E,F). We further aimed to improve shRNA processing by implementing the hsa-miR-30 stem (11) as an extension of the shRNA template stem into db-iPR-hp-s/as. To achieve expression of the correct miR-30 precursor structure including the mismatches in the miR-30 stem region, we considered appropriate mismatches in the stem of the DNA hairpin template structure (FIG. 1A). The implementation of mismatches in the dumbbells did not impair the dumbbell production process. Neither miRNA stems nor mismatches or bulges were reported in the context of dumbbell vector design. The miR-30 stem was previously reported to improve shRNA expressing plasmid vectors (11). The resulting dumbbell db-iPR-miR-hp-s/as triggered 15%/1.5-fold (p<0.01) or 14%/1.3-fold (p<0.05) stronger luciferase knockdown in HEK293T or HepG2 cells compared with the parental vector, despite its 17 bp (34 nt or 12.6%) larger vector size (FIGS. 1E,F). All the three discussed vectors harboured a sense-loop-antisense (5' to 3') orientation of the hairpin transcription cassette. Changing the sense-loop-antisense orientation of construct (db-iPTR-hp-s/as) to an antisense-loop-sense orientation significantly improved the silencing activity of the resulting vector db-iPTR-hp-as/s in HepG2 cells by 28% (p<0.01) but not in HEK293T cells (FIGS. 1E,F). These differences are likely due to alternative shRNA processing and/or processing efficiencies.

Earlier studies reported superior delivery and transcriptional activity triggered by db-vectors compared with plasmid DNA (12,13). First-time we investigated in detail the kinetics of cellular and nuclear db-delivery, transcriptional activity, and target gene knockdown triggered by db-driven shRNA expression in comparison with equivalent plasmid vectors. HepG2 cells were co-transfected using lipofectamine 2000 with the firefly luciferase reporter vector pGL3-Control and equimolar amounts of either a conventional db-vector (db-iPR-linear-s/as) harbouring a linear expression cassette, a minimised hairpin template-transcribing dumbbell (db-iPRT-hp-s/as) or a plasmid (p-iPR-linear-s/as), each expressing a mH1 promoter-driven luciferase targeting shRNA (FIG. 1A). After 10 min, 1 h, 6 h, and 24 h, total episomal DNA, nuclear episomal DNA or total small RNA was isolated and either the mH1 promoter DNA or the shRNA was quantified by rtPCR or rtRT-PCR, respectively. According to the design of our shRNA expression cassettes (5'sense/3'antisense), the rtRT-PCR was suitable to detect both the shRNA precursor and the processed antisense shRNA guide strand via binding of the reverse transcription hairpin primer to the RNA 3'ends. Since db-vectors and plasmids have different PCR amplification efficiencies, we used individual rtPCR standard curves for the absolute quantification of each of the respective vectors. Target gene expression and hence target gene knockdown wasn't detectable 10 min or 1 h post transfection and was instead monitored at 6 h, 12 h, and 24 h.

Figure 3:
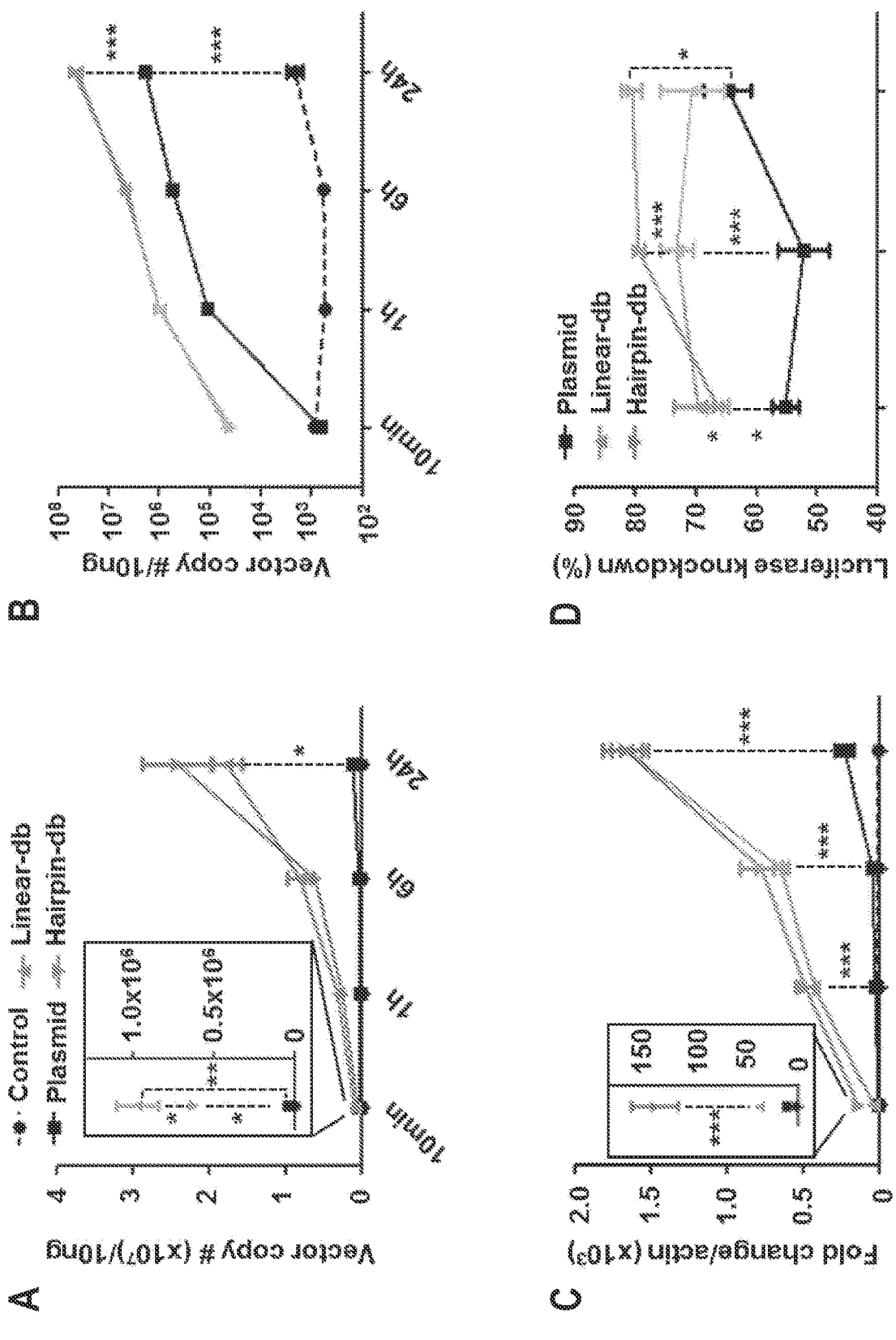
FIG. 3: Kinetics of cellular dumbbell (db) delivery (A), nuclear db-delivery (B), dumbbell-driven small hairpin (sh) RNA expression (C), and shRNA-dumbbell-triggered target gene knock-down in human tissue culture cells (D). HEK293T cells were co-transfected in 24-wells using Lipofectamin 2000 with a luciferase reporter vector (250 ng/well) and equimolar amounts (0.12 pmol/well) of either a db-vector (two different designs) or a plasmid expressing a luciferase targeting shRNA. 10 min, 1 hrs, 6 hrs, and 24 hrs post transfection total episomal DNA, nuclear episomal DNA or small RNA was isolated and either the shRNA gene or the shRNA was quantified by SybrGreen rtPCR (A) or TaqMan-probe-based rtPCR (B) or rtRT-PCR (C). 6 hrs, 12 hrs, and 24 hrs after transfection, shRNA-triggered luciferase knock-down was measured. Luciferase expression was not yet detectable 10 min and 1 hrs post transfection. Error bars indicate mean deviations from average of two (A) or three (B, C, D) independent experiments. Significance was tested using one-way ANOVA with Newman-Keuls post hoc test.
Figure 4:
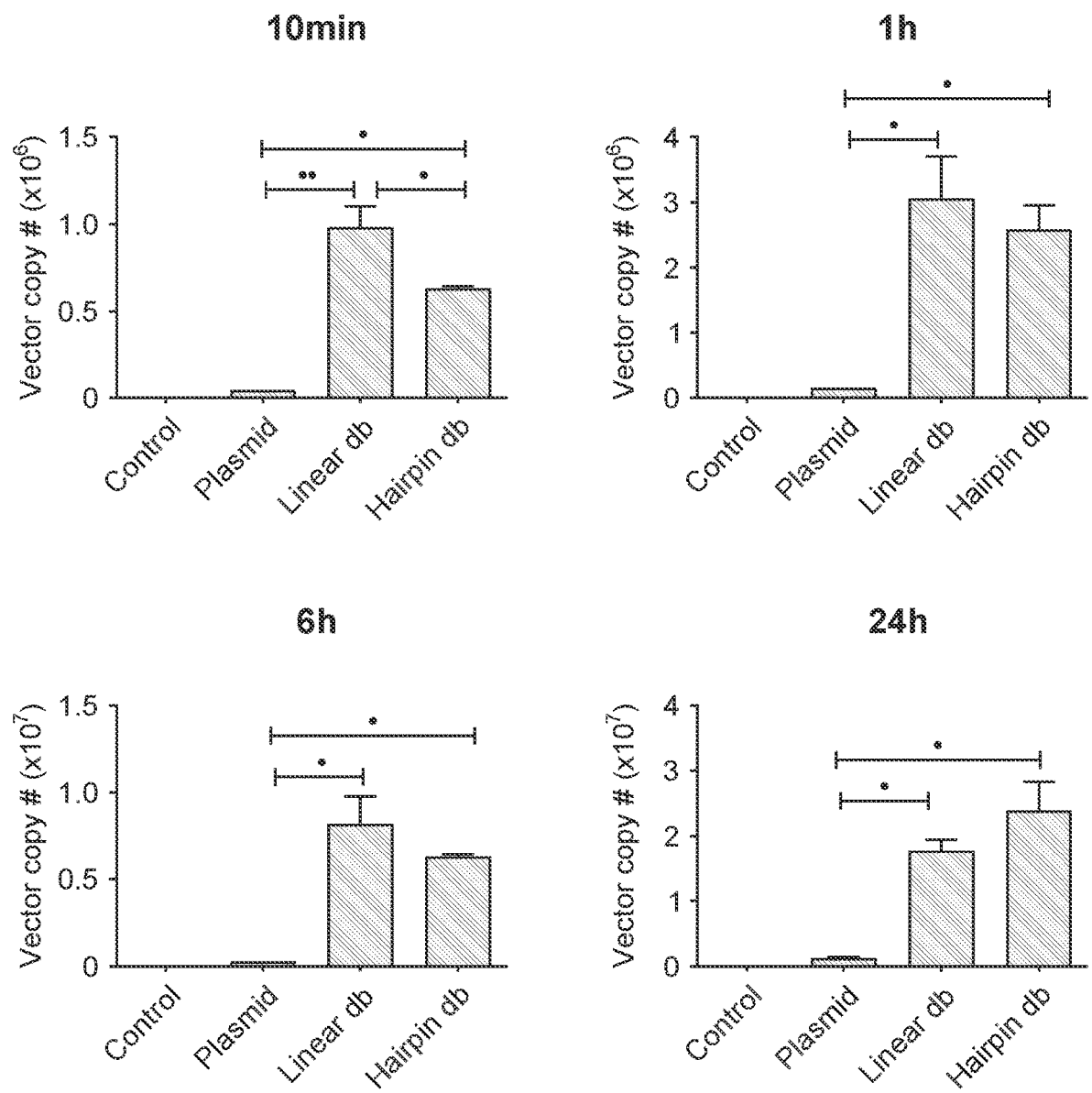
FIG. 4: Kinetics of cellular dumbbell (db) delivery (A), nuclear db-delivery (B), dumbbell-driven small hairpin (sh) RNA expression (C), and shRNA-dumbbell-triggered target gene knock-down in human tissue culture cells (D). HEK293T cells were co-transfected in 24-wells using Lipofectamin 2000 with a luciferase reporter vector (250 ng/well) and equimolar amounts (0.12 pmol/well) of either a db-vector (two different designs) or a plasmid expressing a luciferase targeting shRNA. 10 min, 1 hrs, 6 hrs, and 24 hrs post transfection total episomal DNA, nuclear episomal DNA or small RNA was isolated and either the shRNA gene or the shRNA was quantified by SybrGreen rtPCR (A) or TaqMan-probe-based rtPCR (B) or rtRT-PCR (C). 6 hrs, 12 hrs, and 24 hrs after transfection, shRNA-triggered luciferase knock-down was measured. Luciferase expression was not yet detectable 10 min and 1 hrs post transfection. Error bars indicate mean deviations from average of two (A) or three (B, C, D) independent experiments. Significance was tested using one-way ANOVA with Newman-Keuls post hoc test.
Figure 4:
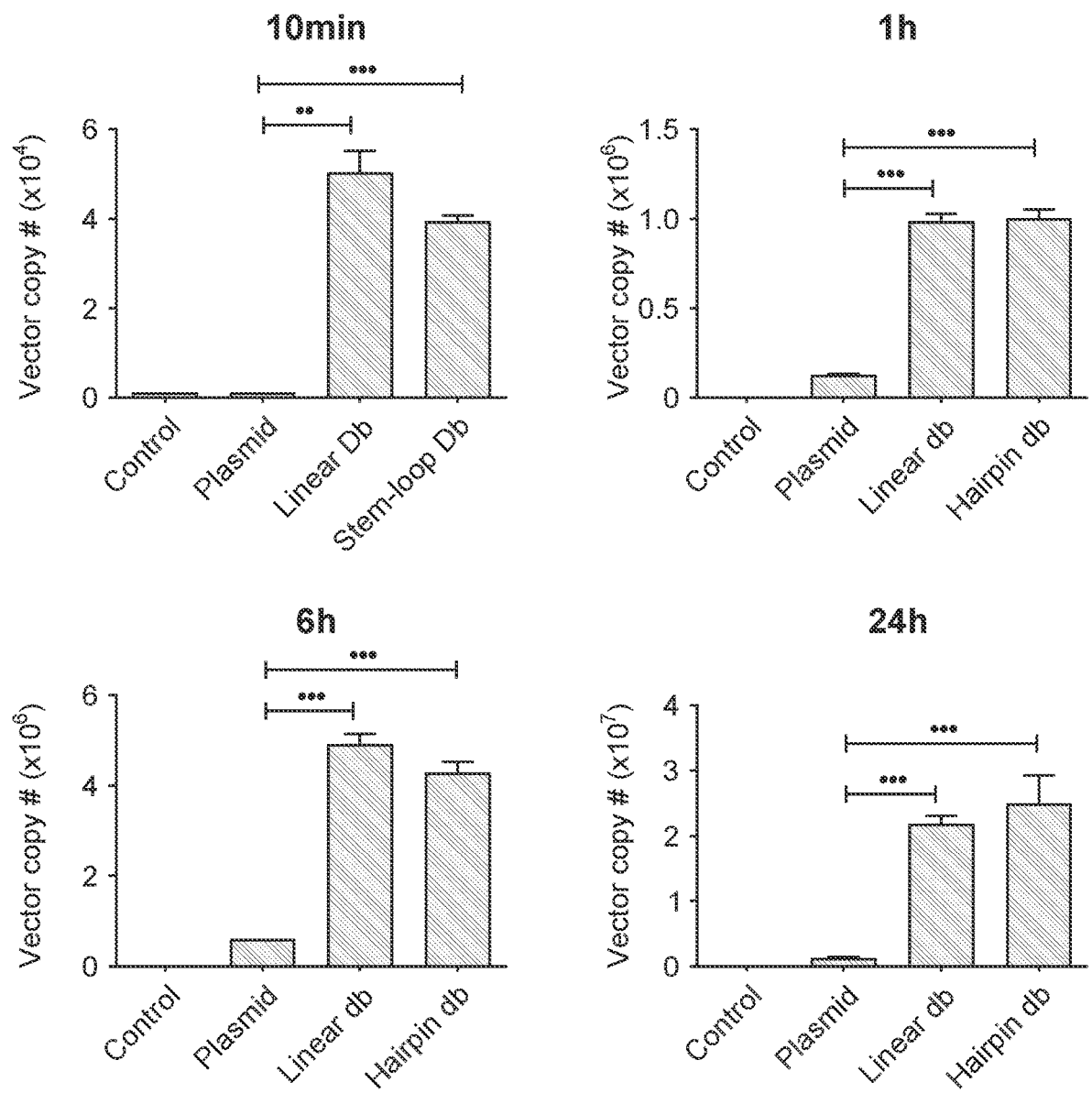
Figure 4:
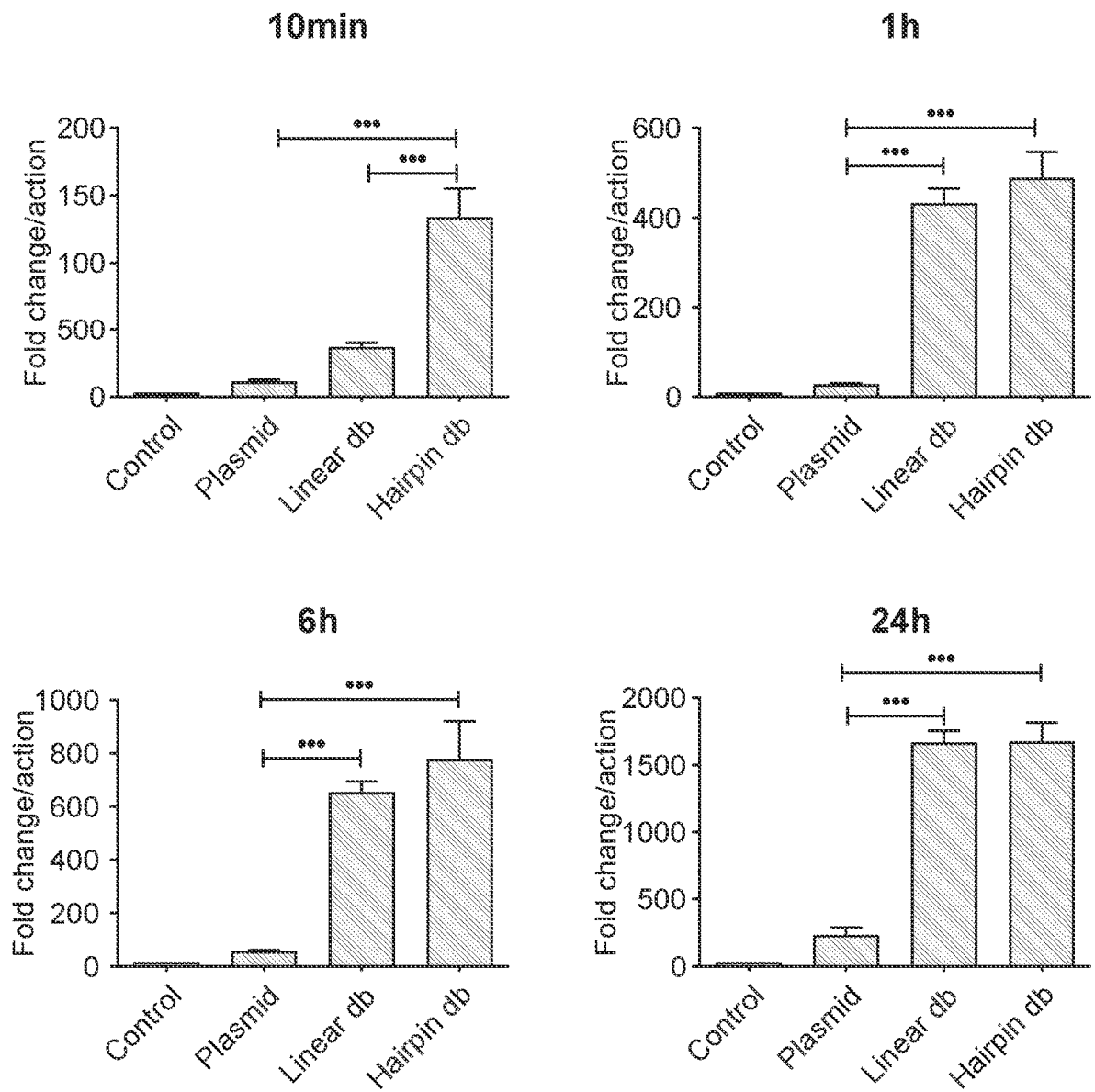
Figure 4:
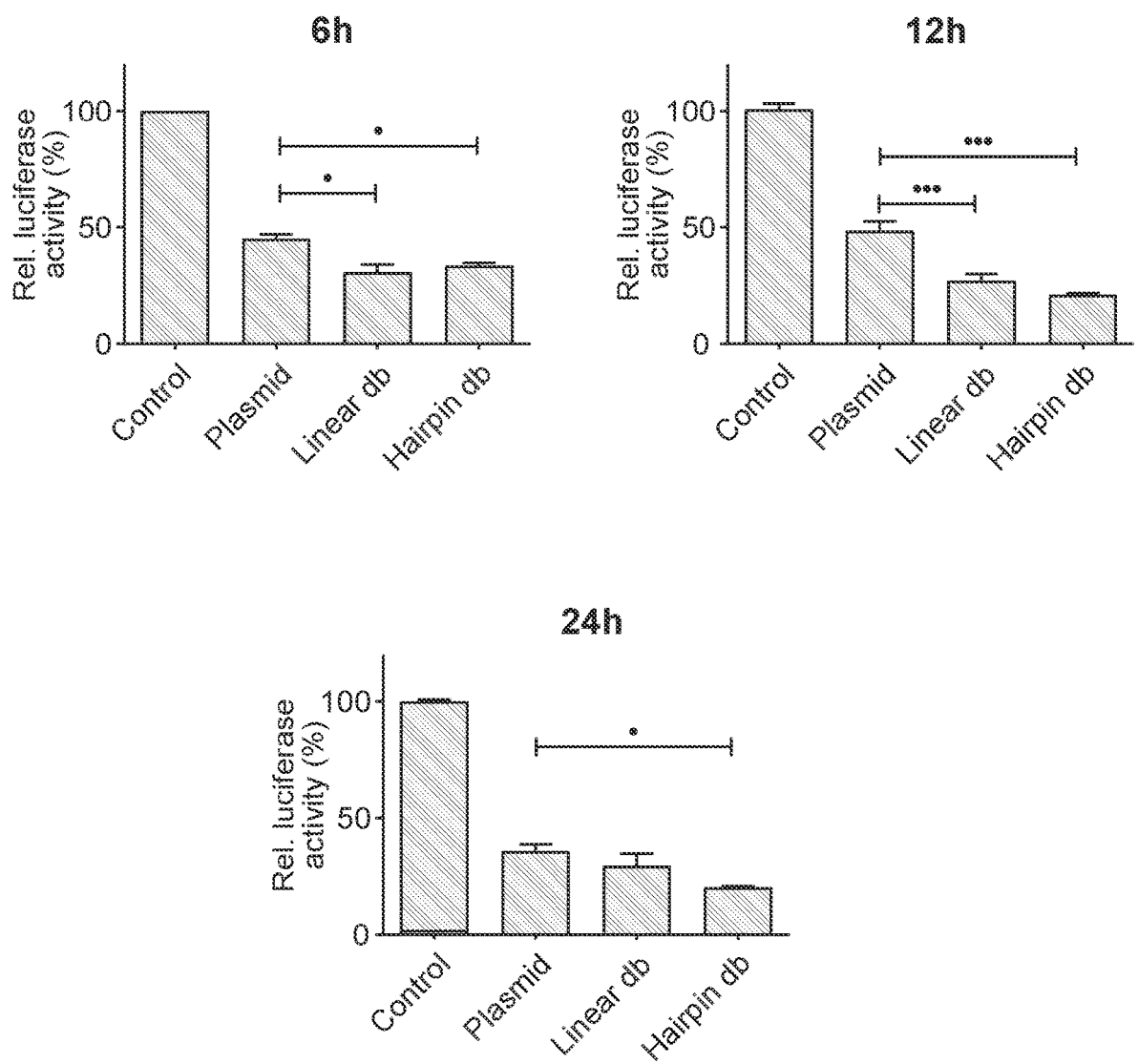

At all investigated time points, the kinetics indicate a clear advantage of the dumbbells over the corresponding plasmid in terms of cellular delivery (transfection) and in particular regarding nuclear delivery and shRNA transcription (FIG. 3; FIG. 4). Cellular db-delivery was enhanced up to 5-fold ($p<0.050$) (FIG. 3A); that is difficult to understand and could be explained by different efficiencies of liposome formation for the different vector molecules. Nuclear db-delivery was enhanced up to 74 or 25-fold ($p<0.001$) 10 min or 24 h post transfection compared with the plasmid (FIG. 3B), pointing towards an accelerated rate of dumbbell diffusion from the cytoplasm into the nucleus. Accordingly, shRNA transcription increased 12 to (or) 7-fold ($p<0.001$) (FIG. 3C) 10 min or 24 hours post transfection. Finally, the db-vectors triggered significantly stronger luciferase knock-down compared with the plasmid vector (FIG. 3D). An advantage of the minimised dumbbell as compared with the conventional dumbbell was most evident (3.7-fold enhancement; $p<0.001$) in terms of the transcriptional activity early (10 min) after transfection and was also indicated by approx. 0% improved knockdown activities. Only in the case of the minimised dumbbell, transcription has to go around the DNA hairpin structure which one would not consider advantageous. Thus, the enhanced transcriptional activity can most likely be assigned to accelerated nuclear diffusion assuming nuclear diffusion of the minimised dumbbell reaches its steady state in less than 10 min and that differences in terms of nuclear delivery between the minimised and the 'linear' dumbbell were not captured anymore by the investigated 10 min time point.

At 10 min post transfection, cellular delivery levels had reached about 6% (plasmid and linear db) or 3% (minimised db) of the 24 h levels, the transcriptional levels about 5/2/8% (plasmid/linear db/minimised db) (FIGS. 3A,C). Nuclear delivery on the other hand increased by approx. three orders of magnitude from 10 min to 24 h ($2.8 \times 10^3 / 0.8 \times 10^3 / 1.2 \times 10^3$-fold for plasmid/linear-db/minimised-db) (FIG. 3B). Notably, the absolute vector copy numbers detected in the whole cell vs. the nuclear extracts cannot be directly compared since we added feeder cells to isolate the nuclei and copy numbers refer to 10 ng of total RNA. The observation that a 1000-fold increase in nuclear delivery of all vectors from 10 min to 24 h post transfection only triggers an about 10-fold augmentation of the detectable RNA levels during the same period of time could be due to (i) transcriptional inactivation of the vector DNA, (ii) enhanced degradation of the transcribed RNA, (iii) incomplete processing of the shRNA precursors which are expected be detected with lower sensitivity compared with the processed antisense shRNA due to their self-complementarity and formation of stable secondary structures, or (iv) toxicity and cell death in the consequence of an oversaturation of the cellular silencing machinery (14). Pathway oversaturation and shRNA-triggered toxicity would be dose-dependent and expected to be much more pronounced in case of the db-vectors which expressed the shRNA at much higher levels. However, the discrepancy between the kinetics of nuclear delivery and shRNA transcription (abundance) was independent of the vectors and the corresponding expression levels.

EXAMPLE 2

Figure 6:
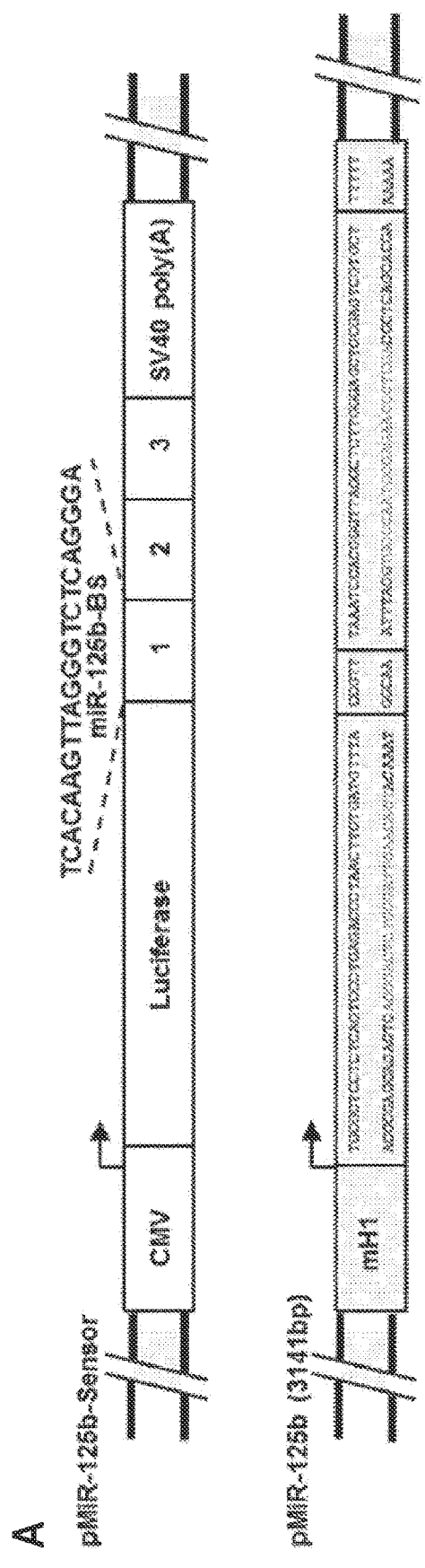
FIG. 6: Knock-down of firefly luciferase-miR-125b sensor reporter gene expression triggered by hsa-miR-125b-expressing dumbbells. A, Design of the miR-125b sensor plasmid pMIR-125b-Sensor (SEQ ID NO 88) harbouring three miR-125b binding site in the 3' UTR and plasmid pMIR-125b (SEQ ID NO 89 and SEQ ID NO 90). Sequences coding for mature miR-125b (red) and miR-125b* (blue) are highlighted. B, Sensing of endogenous and/or pMIR-125b-triggered miR-125b overexpression. HepG2 cells seeded in 24-wells were (co-)transfected with 400 ng pMIR or pMIR-125b-Sensor plus 400 ng pSuper feeder DNA or 100 ng pMIR-125b.
Figure 6:
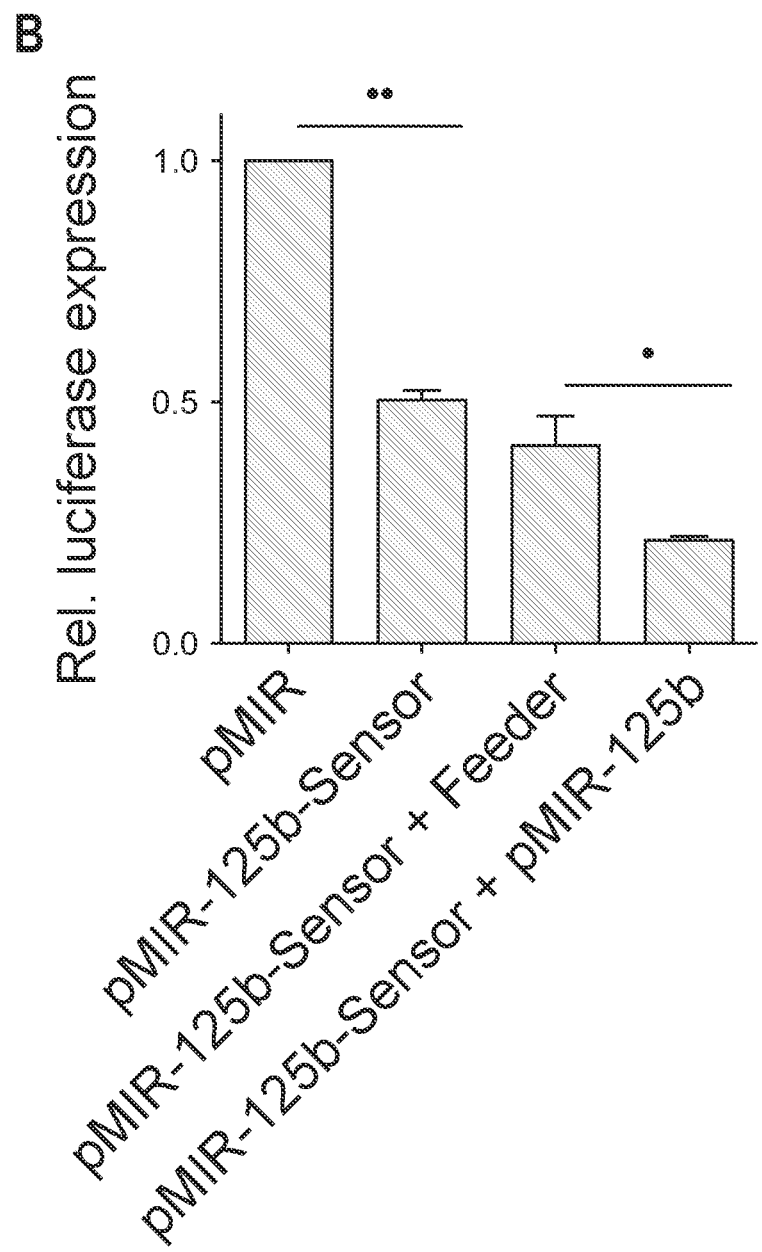

Design of Hairpin-Template Transcribing Dumbbell Vectors for microRNA Expression The minimised db-design along with the new protocol for db-generation is applicable for shRNA- and miRNA-expressing dumbbells. We designed a human miR-125b-1 expressing minimised hairpin template-transcribing dumbbell with integrated promoter/restriction/terminator element (db-iPRT-hp-miR) as well as a conventional dumbbell (db-linear-miR) and a plasmid vector (p-linear-miR), the latter each with linear miR-125b-1 expression cassettes (FIG. 5A). miR-125b-1 was reported to function as tumour suppressor miRNA by targeting the oncogenes LIN28B and IL6R (15,16). All three vectors express the miR-125b-1 precursor structure and to achieve that, various mismatches and bugles were implemented into the design of the minimised dumbbell. To efficiently sense miR-125b-1 expression we constructed a miR-125b-1 sensor plasmid by replacing the firefly luciferase 3'UTR of plasmid pMIR-Report with a repeat of three miR-125b binding sites (FIG. 6A). The functionality of the sensor plasmid was tested by transfection of HepG2 cells with the sensor plasmid alone and compared with co-transfection of sensor plasmid plus feeder DNA or the miR-125b-1-expressing plasmid. 24 h post transfection luciferase expression was measured and standardised relative to the expression of the sensor-negative reporter vector (FIG. 6B). The sensor vector efficiently detected endogenous miR-125b-1 expression as well as plasmid-triggered miR-125b-1 overexpression. Next we co-transfected HepG2 cells with the sensor plasmid and the different miR-125b-1-expressing vectors. We compared equimass amounts of the miR-125b expressing vectors in this experiment using identical amounts of lipofectamine 2000. Under these experimental conditions, the db-vectors and most pronounced the minimised dumbbell triggered 3.9-fold ($p<0.01$) stronger target gene knockdown as compared with the plasmid vector (FIG. 5C). No difference in knockdown activity was detected for dumbbells produced with our new protocol or alternatively using the enzymatic ligation assisted by nuclease (ELAN) method (8), indicating both protocols produce functionally equivalent minimised dumbbells (FIG. 5C). The functionality of the minimised miR-125b-1-expressing dumbbell was confirmed in HEK293T and CL48 cells (FIGS. 5D,E).

EXAMPLE 3

Nuclear DNA Import Sequences Improve Target Gene Knockdown Triggered by Small RNA Expressing Dumbbell Vectors Fast passive diffusion from the cytoplasm into the nucleus is regarded to be one of the key features that can be assigned to db-vectors. For larger plasmid DNA it was reported that certain sequences harbouring transcription factor binding sites significantly enhance gene expression. Examples are the SV40 enhancer sequence (17,18), the smooth muscle γ-actin (SMGA) promoter (19,20), and the origin of replication of the Epstein-Barr virus (oriP), the latter of which depends on the expression of the viral nuclear antigen 1 (EBNA1) in order to be functional (21). We investigated whether this strategy is suitable to further improve nuclear import and gene expression of db-vectors. Therefore we implemented either the 237 bp full-length SV40 enhancer (fEnh) or a 72 bp minimal version (mEnh) of it (17) into the minimised miR-125b-1-expressing dumbbell upstream of the mH1 promoter (FIG. 5A) to generate dumbbells db-fEnh-iPT-hp-miR and db-mEnh-iPT-hp-miR. In HepG2 cells co-transfected with the pMIR-125b-1 sensor plasmid and the db-vectors, strongest miR-125b-1-mediated luciferase knockdown (93%; $p<0.001$) relative to the control was triggered by the dumbbell harbouring the full-length SV40 enhancer, followed by the dumbbell with the minimal SV40 enhancer (87%; $p<0.001$), and the enhancer-negative parental db-vector (69%; $p<0.001$) (FIG. 5F). These data demonstrate, SV40 enhancer elements can significantly enhance db-driven miRNA expression, 2.3 (mEnh) or 4.5-fold (fEnh) compared with the enhancer-negative control, though their implementation triggers a relatively stronger increase of vector size in case of the small dumbbells (47 or 156%) compared with a much larger plasmid vector (2.4 or 8%). Though, both transcriptional activation and/or active nuclear DNA import and retention can account for the enhancement of gene expression triggered by these sequence elements, it is unlikely that the SV40 enhancer promotes transcriptional activation of the heterologous mH1 polymerase III promoter in this experimental setting. The postulated mechanism underlying an active nuclear DNA import is that transcription factors harbouring peptide nuclear localisation signals bind to these DNA sequences and co-import the bound DNA piggy-back into the nucleus by means of the protein nuclear import machinery (22).

EXAMPLE 4

Design of Antisense miRNA-Expressing Dumbbell Vectors

As miRNAs are important posttranscriptional regulators of metazoan gene expression, both their overexpression and functional inhibition can be of therapeutic value. Most miRNA antagonists are chemically synthesised oligodeoxyribonucleotides with antisense orientation to the miRNA and/or its precursor (23,24). Alternatively, long miRNA targeting antisense RNAs (miRNA sponges) or siRNAs were described as well. Short endogenously expressed miRNA-targeting antisense RNA (asRNA) has not been described yet. We investigated the possibility to use small db-vectors for antisense miRNA expression. As a target we selected hsa-miR-21 which is overexpressed in the context of hepatocellular carcinoma (25) and designed four antisense miRNA (as-miRNA) structures targeting at the same time the mature miR-21 and part of its precursor (pre-miR-21), thus overlapping with one of the dicer cleavage sites. That is, these as-miRNAs would be suitable to target the primary miR-21 transcript, pre-miR-21, and/or mature miR-21 (FIG. 7A). Despite the fact that the available as-miRNA sequence and structure spaces were very limited, we identified two highly structured and two less structured as-miRNA candidates using in silico tools for RNA secondary structure analysis (26,27). In particular free unpaired ends of asRNAs were reported to correlate with efficient target binding and activity. Accordingly, selected highly structured as-miRNAs fold stable hairpin structures avoiding free ends; the less structured antagonists fold less stable secondary structures and harbour free 5' and 3' ends (FIG. 7A). We designed a luciferase reporter-based miR-21 sensor plasmid (p21-Sensor) harbouring a repeat of three miR-21 binding sites in the firefly luciferase 3'UTR as well as db-vectors expressing the selected 'unstructured' (A1 and A3) or structured (A2 and A4) as-miRNAs (FIGS. 7B,C). CL48 cells were transfected either with the sensor construct alone or together with the respective as-miR-expressing db-vectors and luciferase activity was monitored 48 h post transfection (FIG. 7D). All four dumbbells/as-miRNAs triggered comparable levels of endogenous hsa-miR-21 inhibition as indicated by an about 3-fold increase ($p<0.01$) of luciferase expression. AsRNA-mediated inhibition of gene expression is a kinetically controlled process (28), i.e. fast target binding correlates with activity, and longer asRNAs are faster target binders compared with short asRNAs on a statistical basis (29). However, it was also shown that relatively short asRNAs of about 100 nt in length can be very strong inhibitors provided they form flexible RNA secondary structures with long free ends (26,30). Thus it was at first view surprising that as-miRNA structures with closed ends were as potent inhibitors of miR-21 function as structures with free ends. However, it was also reported that unstructured asRNA is much more prone to ribonucleolytic degradation (26,30). For the group of very short as-miRNAs investigated here we hypothesise that (i) the more unstructured RNAs might be faster target binders but less stable whereas (ii) the more structured RNAs might be slower binding though more stable and that (iii) target binding is just balanced against endogenous RNA stability.

Our analyses indicate an inverse correlation between the sizes of equally featured 'naked' DNA-based vectors and the kinetics of gene expression. The advantage of the dumbbells over the plasmids was found to be highly evident when delivering equimolar amounts of vector DNA and is expected to become even more pronounced when equimass amounts would be applied. Considering limitations associated with some delivery strategies e.g. with regard to maximally deliverable volumes or toxicity triggered by liposomal or other complexing compounds, together with the fact that the total mass of deliverable DNA is limited, it can be regarded as a strong advantage of the db-vector system that equimass amounts correspond to much higher molar amounts as compared with larger minicircles or plasmids.

In our in vitro system, small dumbbell size is advantageous mainly in terms of improved nuclear delivery and it remains to be tested whether that goes along with a disproportionate higher risk of nuclear vector integration. In vivo, genetic vectors additionally have to manage extracellular transport including extravasation, diffusion through the extracellular matrix network, target cell binding and internalisation. To overcome these physical including membrane barriers, a small vector size can be highly beneficial. Our data demonstrate that dumbbell vectors trigger accelerated, prolonged, transient small RNA expression. Thus, in terms of small RNA delivery, dumbbell vectors may close the existing gap between short-term knockdown effects triggered by siRNAs or miRNA mimics and long-term effects that can be achieved with integrating lentiviral vectors thereby enabling and facilitating therapeutic applications of this vector system.

EXAMPLE 5

Design of Dumbbell Vectors for Coding RNA Expression—A Spliceable Intron and/or the SV40 Enhancer Improve Dumbbell-Driven Gene Expression Most db-vectors reported in the literature were designed to express functional proteins and, hence, much larger in size compared with the small RNA expressing dumbbells discussed above. We investigated as to whether the full length SV40 enhancer would be suitable to enhance protein expression driven by large db-vectors. As a second molecular feature to enhance protein expression we implemented a spliceable intron. While the implementation of introns into db-vectors was reported earlier (31), SV40 enhancer elements have not been described in dumbbells yet. Using the ELAN method we generated a db-vector containing a SV40 promoter-driven firefly luciferase gene and the SV40 polyadenylation site (db-luc) as well as variations of this parental vector harbouring either the full-length SV40 enhancer (db-luc-enh), the human β-globin gene chimeric intron (32) (db-int-luc), or both (db-int-luc-enh) (FIG. 8A). As controls we constructed four plasmid vectors having identical expression cassettes and features but which in addition contained the 2855 bp pGL3-Control backbone. HEK293T and HepG2 cells were transfected with equimass amounts of the plasmid and db-vectors and luciferase gene expression was monitored 48 h post transfection. In HEK293T cells, plasmids and dumbbells triggered a comparable level of gene expression; in HepG2 cells db-triggered expression was 3 to 7-fold ($p<0.001$) stronger (FIGS. 8B,C). While the implementation on an intron enhanced gene expression of all constructs unconditionally and in both cell lines, the SV40 enhancer was active in HepG2 cells but not in HEK293T cells in which the SV40 enhancer slightly impaired gene expression. In HepG2 cells, implementation of the SV40 enhancer triggered a remarkable 16-fold ($p=0.005$) or 27-fold ($p<0.001$) enhancement of luciferase expression compared with the respective enhancer-negative dumbbells db-luc or db-int-luc. Highest levels of luciferase expression were triggered by dumbbell db-int-luc in HEK293T cells and by the dumbbell db-int-luc-enh in HepG2 cells. In HepG2, db-int-luc-enh-triggered gene expression was 7-fold higher ($p<0.001$) than for the equally featured plasmid p-int-luc-enh, x-fold higher ($p<0.001$) than for the standard dumbbell db-luc, and 160-fold higher ($p<0.001$) compared with the basic plasmid p-luc. These numbers are still remarkable when considering the about 50% smaller dumbbell size and the approx. twofold higher molar dumbbell amounts tested.

EXAMPLE 6

Design of Trans-Splicing RNA-Expressing Dumbbells

Figure 9:
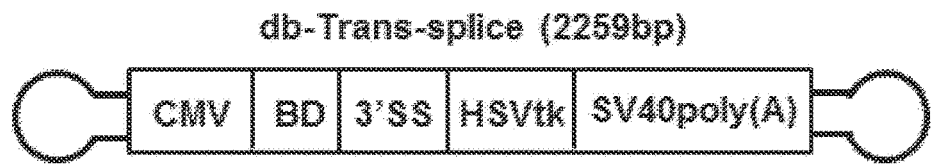
FIG. 9: Generation of a chimeric AFP-HSVtk RNA in HepG2 cells triggered by a trans-splicing RNA expressed from a dumbbell or plasmid vector. A, Design of a dumbbell vector for the expression of a trans-splicing RNA suitable to label the AFP pre-mRNA with the HSVtk message via 3' exon labelling. BD: AFP-specific antisense binding domain; 3'SS: 3' splice acceptor site. B, The trans-splicing RNA binds to intron 5 of the AFP pre-mRNA via the specific binding domain and triggers splicing in trans between the splice donor site of AFP intron 5 and the splice acceptor site of the trans-splicing RNA. Binding sites of AFP- or HSVtk-specific TaqMan probes are indicated. BP: branch point; Ppy: poly pyrimidine tract. C, HepG2 cells seeded in 24-wells were (co-)transfected with 500 ng of a vector expressing an AFP minigene (encompassing exons 3 to 6 including introns 3 and 5) alone or together with 0.2 pmol of a trans-splicing RNA expressing plasmid or dumbbell vector. 24 h post transfection total RNA was isolated and relative levels of chimeric AFP-HSVtk transcripts were detected by TaqMan-probe-based rtRT-PCR using an AFP- or HSVtk-specific probe. Relative trans-splice activities were calculated by the comparative Ct method ($\Delta\Delta Ct$) using β-actin as internal control. The indicated chimeric RNA levels were calculated as 2-$\Delta\Delta Ct$ Error bars indicate mean deviations from average of three independent experiments. Significance was tested using one-way ANOVA with Newman-Keuls post hoc test.
Figure 9:
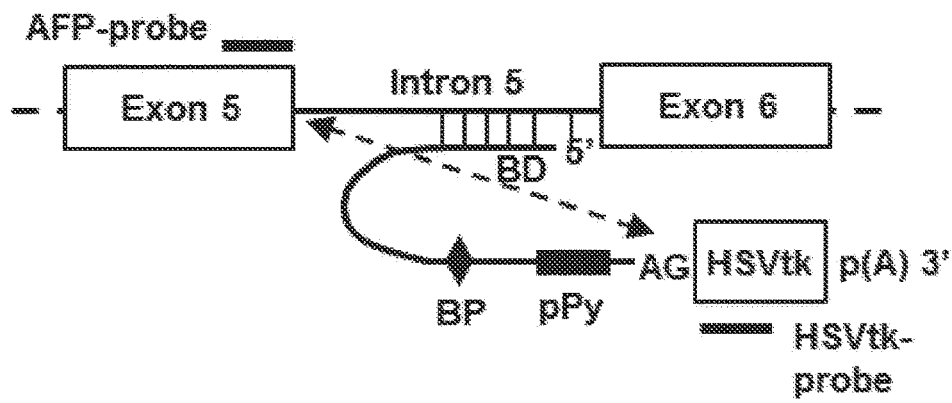
Figure 9:
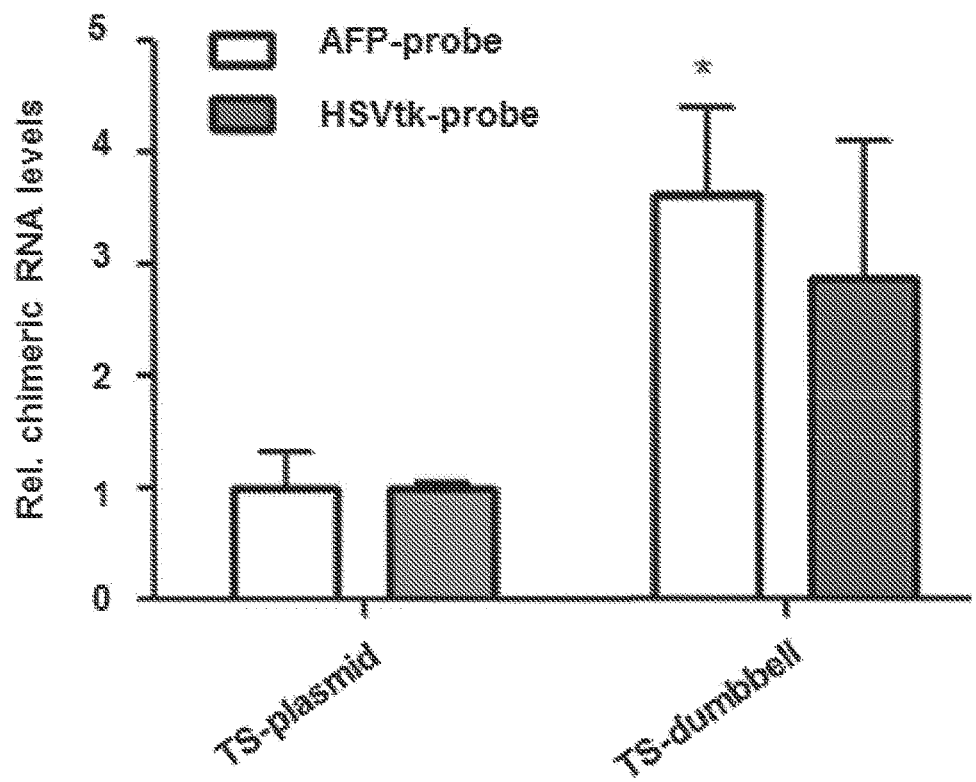

We explored the possibility of using db-vectors for delivery of RNA trans-splicing into human tissue culture cells and compared the db-based with the plasmid-based delivery approach. Spliceosome-mediated RNA trans-splicing represents an alternative form of splicing that describes the joining of sequences originating from distinct transcripts (33). RNA trans-splicing is increasingly being explored for diagnostic and therapeutic applications as it can be used for genetic repair and reprogramming as well as for labelling of endogenous transcripts with death signals for suicide gene therapy or with fluorescent proteins for gene expression imaging. Our trans-slicing RNA was composed of a 5'-terminal antisense binding domain targeting intron 5 of the alpha-fetoprotein pre-mRNA, a splice acceptor site, and a sequence coding for a fusion protein of the P2A proteolytic cleavage site (34) and the herpes simplex virus thymidine kinase (HSVtk). This trans-splicing RNA was capable of tagging the endogenous AFP or an overexpressed AFP mini-gene with the HSVtk message via trans-splicing-based 3'-end labelling. Successful trans-splicing leads to the expression of the HSVtk enzyme which can trigger a cell death signal upon delivery of the drug ganciclovir for suicide gene therapy (35-37). HepG2 cells were transfected with equimolar amounts of the trans-splicing RNA-expressing plasmid or db-vector, and total RNA was isolated 24 h post transfection. The efficiency of trans-splicing was monitored by rtRT-PCR-based detection of the resulting chimeric AFP-HSVtk RNA using each one AFP-specific and one HSVtk-specific TaqMan-probe (FIG. 9A). The db-vector triggered a 3.6-fold stronger ($p<0.05$ for the AFP-probe) chimeric RNA signal compared with the plasmid expressing the identical trans-splicing RNA molecule (FIG. 9B).

EXAMPLE 7

Figure 10:
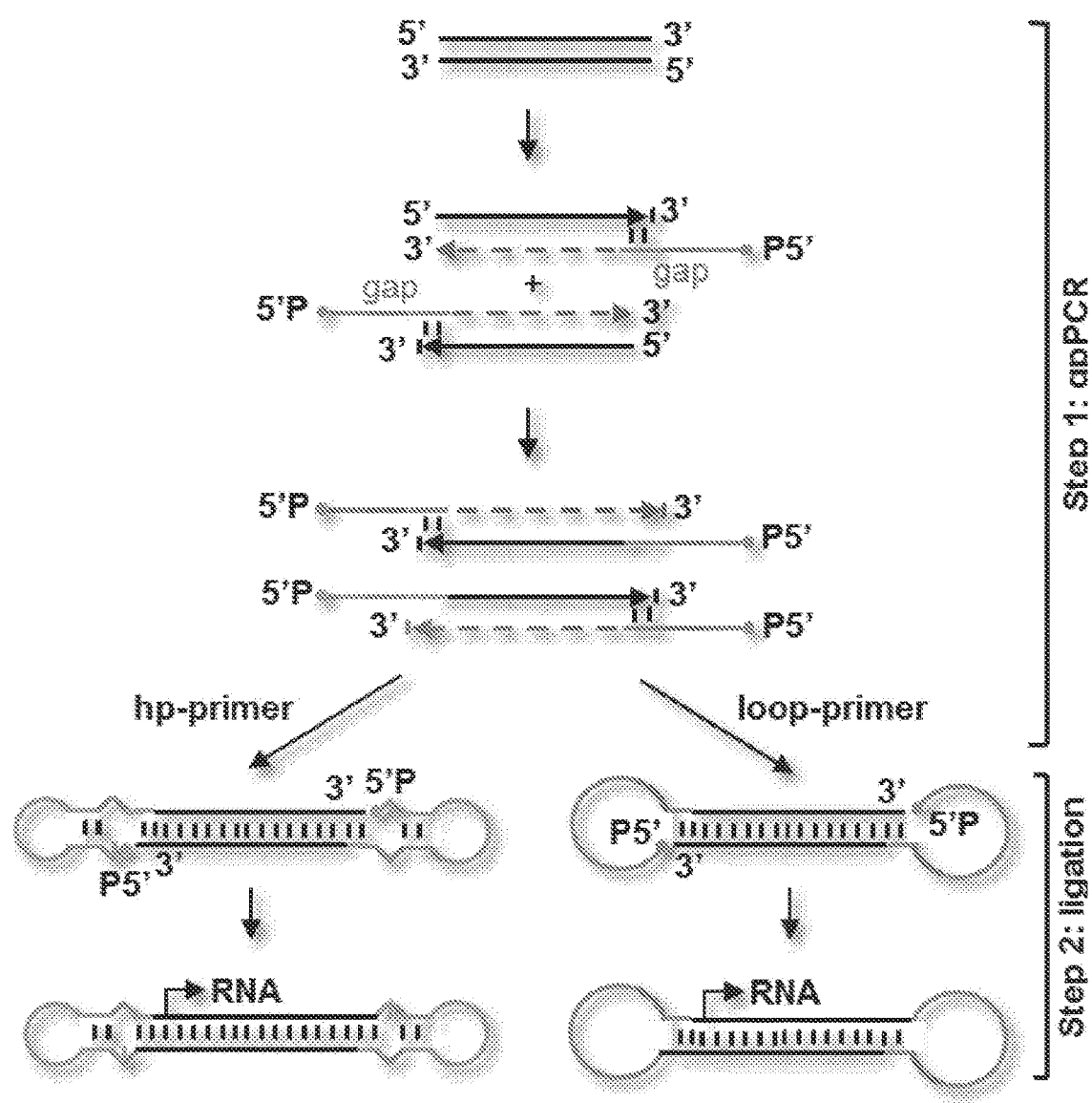
FIG. 10: Schematic depiction of gap-primer-PCR (gpPCR)-based formation of DNA dumbbell vectors. In step 1, 5'-phosphorylated primers harboring abasic gaps are used to amplify the expression cassette of interest. The polymerase halts as soon as the gap is reached, yielding a PCR product with 5'-overhangs. Two kinds of gap-primers can be used: hairpin primers (hp) which prompt the 5'-overhangs to fold back and to position them close to the 3'-OH groups (left panel); or unstructured (loop) primers (right panel). In step 2, the gpPCR products are ligated to form the covalently closed dumbbell structure. Hp-primer products are ligated with the double-strand-specific T4 DNA ligase; loop-primer are ligated using the single-strand-specific CircLigase. Optionally, exonuclease treatment can be considered to purify the dumbbell DNA.
Figure 11:
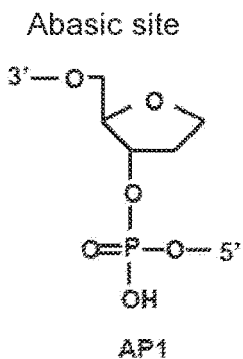
FIG. 11: Design and structure of chemically-modified gap-primers. Left panel: molecular structures of the abasic gaps; right panel: sequence and structure of hairpin and loop gap-primers. A, AP1 (dSpacer1) primers harbouring a single tetrahydrofuran-based abasic site mimic (forward primers SEQ ID NO 96, SEQ ID NO 97; reverse primers SEQ ID NO 98, SEQ ID NO 99). B, AP3 (dSpacer3) primers harbouring three tetrahydrofuran-based abasic site mimics (forward primers SEQ ID NO 100, SEQ ID NO 101; reverse primers SEQ ID NO 102, SEQ ID NO 103). C, S9 (PEG-150) primers harbouring a triethylene glycol-based spacer (forward primers SEQ ID NO 104, SEQ ID NO 105; reverse primers SEQ ID NO 106, SEQ ID NO 107)
Figure 11:
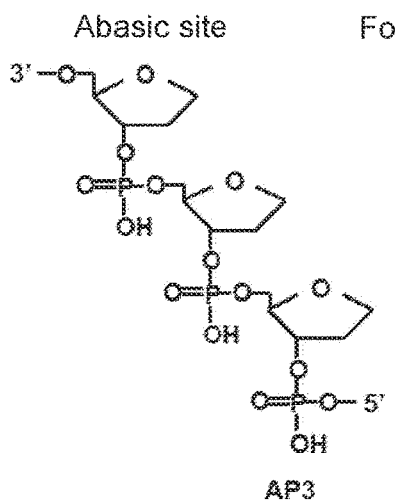
Figure 11:
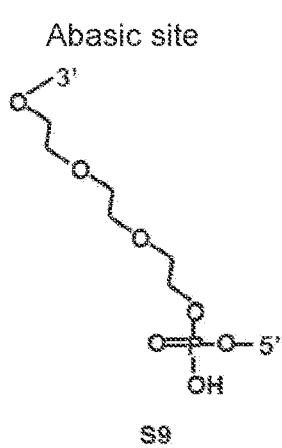

Gap-Primer PCR—Efficient Production of Superior Dumbbell-Shaped DNA Minimal Vectors for Small RNA Expression To further simplify and cheapen dumbbell production and to increase the yields, we developed a two-step PCR-based method that involves chemically-modified gap-primers (FIG. 10). The new gap-primer-based PCR (gpPCR) method maximally reduces number and amount of enzymes and oligonucleotides needed for the production of dumbbell-shaped DNA vectors. In step 1, the expression cassette of interest (coding or non-coding) is amplified by PCR with a pair of primers containing a 5'-phosphate, a central gap, and a 3'-terminal target binding site with a 3'-hydroxyl group (3'-OH). The extension of both newly synthesized strands is terminated upon reaching the gap yielding PCR products with 5'-overhangs. In step 2, the phosphorylated 5'-overhangs are ligated intramolecularly to the 3'-OH groups to form the covalently closed dumbbell structure. The essential idea behind our method is that the abasic gaps cannot function as templates for base-pairing during primer extension forcing the polymerase to halt, thus directly yielding 5'-overhangs ready for efficient intramolecular ligation. The chemical nature of the abasic gaps may affect the efficiency of PCR amplification, ligation, or the biological function of the final dumbbell vector, and the length of the gap may impact polymerase halting. To achieve optimal efficiency and efficacy of dumbbell-production, we investigated oligonucleotides harbouring abasic gaps of different chemistry and length (FIG. 11): dSpacer1 (AP1) and dSpacer3 (AP3) are tetrahydrofuran-based mimics of one or three apurinic/apyrimidinic abasic sites; and PEG-150 (TEG) is a triethylene glycol-based spacer with a molecular weight of 150 Da and a length of 1.3 nm which approximately corresponds to four base pairs (38,39). For each of the three gap variants we investigated two sets of primers: Firstly, self-complementary hairpin (hp) primers causing the 5'-overhangs to fold back forming a stem loop structure and positioning the 5'-phosphate close to the 3'-OH groups (FIG. 11, left panel). To form linear dumbbell vectors, we bridged the AP1 or AP3 gaps in the opposing strand with one or three nucleotides (nt), and the TEG gap with four nt respectively, and ligated the ends using T4 DNA ligase. Secondly, we designed unstructured (loop) primers forming open 5'-overhangs which were ligated using the single-strand-specific Circligase (FIG. 11, right panel) (40) Exonuclease resistance represents a characteristic feature of covalently closed dumbbell-shaped DNA (41). Thus, ligation reactions can be treated with T7 DNA polymerase, which exhibits a strong 3' to 5' exonuclease activity, to degrade all educts and by-products yielding purified dumbbell DNA (42).

Figure 12:
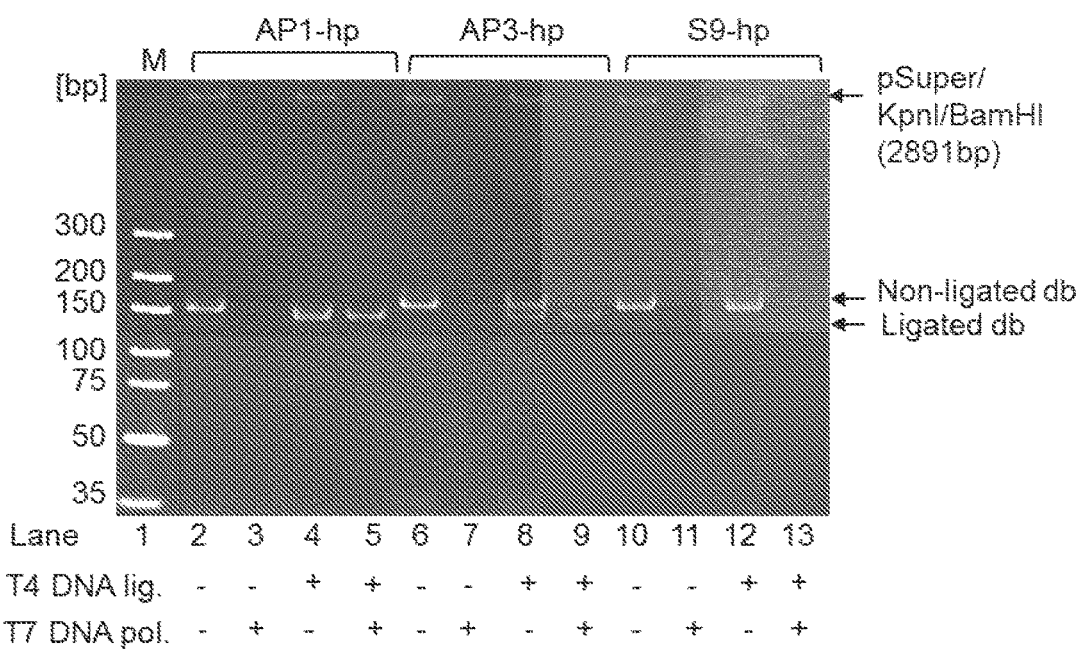
FIG. 12: Dumbbell DNA vector formation using hairpin (hp)-gap-primer PCR. Products yielded from gpPCR using the AP1-hp, AP3-hp, and S9-hp primers were analysed before (lanes 2, 6, and 10) and after ligation (lanes 4, 8, and 12). The unligated (lanes 3, 7, and 11) and ligated products were subjected to T7 DNA polymerase (exonuclease) treatment (lanes 5, 9, and 13). Highest dumbbell yields were observed with AP1-hp primers (lane 5) followed by the AP3-hp primers (lane 9). No dumbbell DNA was detectable with the S9-hp primers (lane 13). Ethidium bromide stain of a 10% PAGE.

We investigated the efficiency of our new method in terms of dumbbell production using first the hp-primers together with T4 DNA Ligase (FIG. 12). Therefore, hp-primer PCR products were treated with exonuclease either before or after ligation and the resulting DNA products were analysed by 10% polyacrylamide gel electrophoresis (PAGE). All hp-primer PCR reactions yielded products of the expected size of 179 to 185 bp (lanes 2, 6, and 10) which were completely degraded during exonuclease treatment (lanes 3, 7, and 11) due to the availability of free 3' ends. Ligase treatment triggered a detectable change in DNA topology reflected by an increase in mobility, which is characteristic for dumbbell DNA under the conditions of this analysis. Such a mobility shift was observed for PCR products generated using the AP1- (lane 4) or with lower yields the AP3-gap-primers (lane 8), but not with the TEG-primers (lane 12). Accordingly, exonuclease treatment left highest dumbbell yields for the AP1-gpPCR (lane 5), followed by the AP3-gpPCR (lane 9); no dumbbell was produced based on TEG-gpPCR (lane 13).

Our results indicate that among the series of hp-primers, only those harbouring tetrahydrofuran-based gaps are suitable to produce dumbbell vectors, with highest yields obtained for the smallest gap AP1. That is, a single abasic site efficiently pauses the polymerase without providing any evidence that the enzyme may jump over the gap. It is reasonable to assume that the larger AP3 gap halts the polymerase as effectively as the shorter AP1 gap. However, AP1-primer ligation likely is more efficient due to the more precise positioning of the 5'-end for ligation with the 3'-end. Currently the question cannot be answered as to whether TEG-gaps are either skipped by the polymerase yielding double-stranded DNA ends which would be unsuitable for dumbbell formation, or alternatively trigger the formation of substrates which are difficult to ligate.

Figure 13:
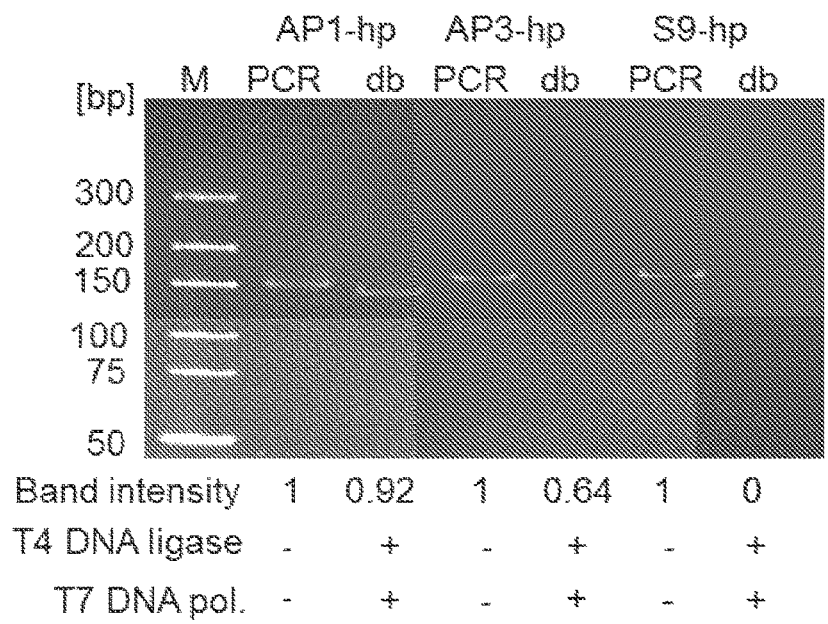
FIG. 13: Conversion yields from linear gpPCR products to covalently closed dumbbell DNA. gpPCR products were either treated with ligase and exonuclease or not, and subjected to 10% PAGE. Band intensities of the ethidium bromide stained gels were quantified using ImageJ 1.37v software (NIH, USA). A, hp-primer PCR products. B, AP1-loop-primer PCR product. C, Anti-GFP-shRNA expressing dumbbell db-Nick produced with the nicking enzyme method. D, Anti-luciferase-shRNA expressing dumbbell db-ELAN produced with the ELAN method.
Figure 13:
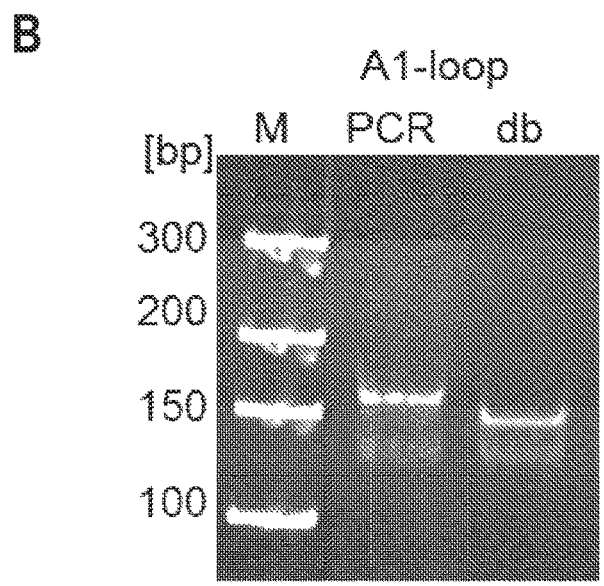
Figure 13:
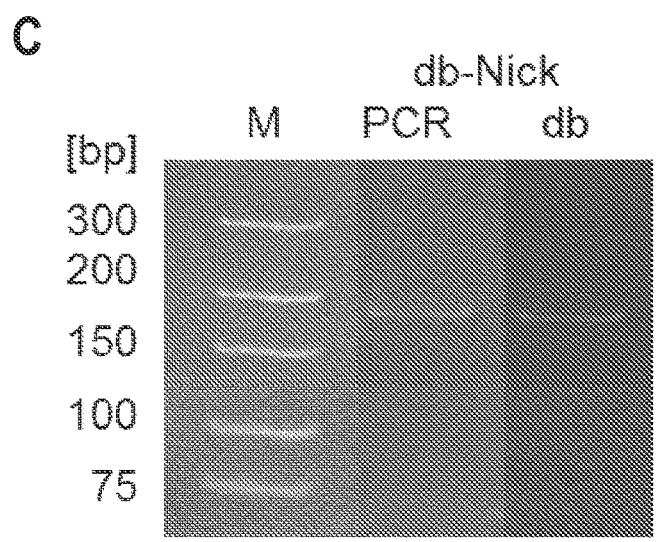
Figure 13:
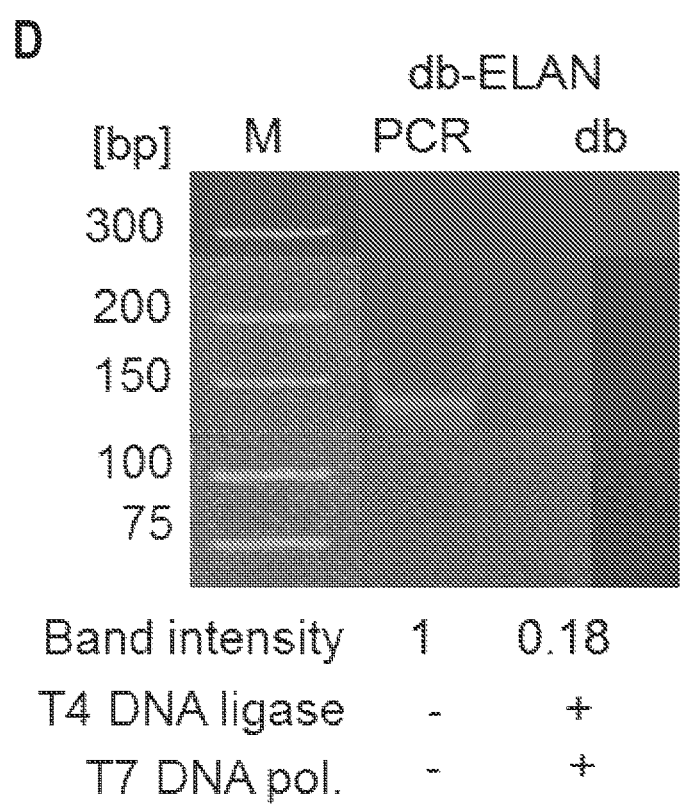

Next, we evaluated the dumbbell conversion yields by determining the ratios of dumbbell vector DNA after ligation and exonuclease treatment divided by the PCR product yields prior to enzymatic treatment. Among the hp-primer series, highest conversion yields were obtained with the AP1-hp-primers (92%), followed by the AP3-hp-primers (64%), and no dumbbell DNA was produced with the TEG-hp-primers (FIG. 13A). Among the loop-primer series, only the AP1-loop-primers triggered dumbbell formation (75%) supporting the hypothesis that larger abasic gaps lead to difficult-to-ligate DNA substrates (FIG. 13B). In comparison with our new method, the conventional dumbbell production techniques exhibited significantly lower conversion yields of 57% (nicking enzyme method) or 18% (ELAN method), both lower than initially reported in the literature based on the same quantification method (FIGS. 13C,D). The yields of converting the expression cassette of interest into covalently closed exonuclease-resistant dumbbells as well as the purity of the obtained dumbbells were found to inversely correlate with the numbers of (i) manufacturing steps, (ii) involved enzymes, and (iii) possible by-products that can be formed. Accordingly, highest yields of purest dumbbells were achieved with the new gpPCR-method, followed by the nicking enzyme method and the ELAN-method. Notably, though the measured yields may vary depending on the used method of quantification or the batch of ligase, they represent a reliable indicator to compare the relative strengths' of the methods.

Figure 14:
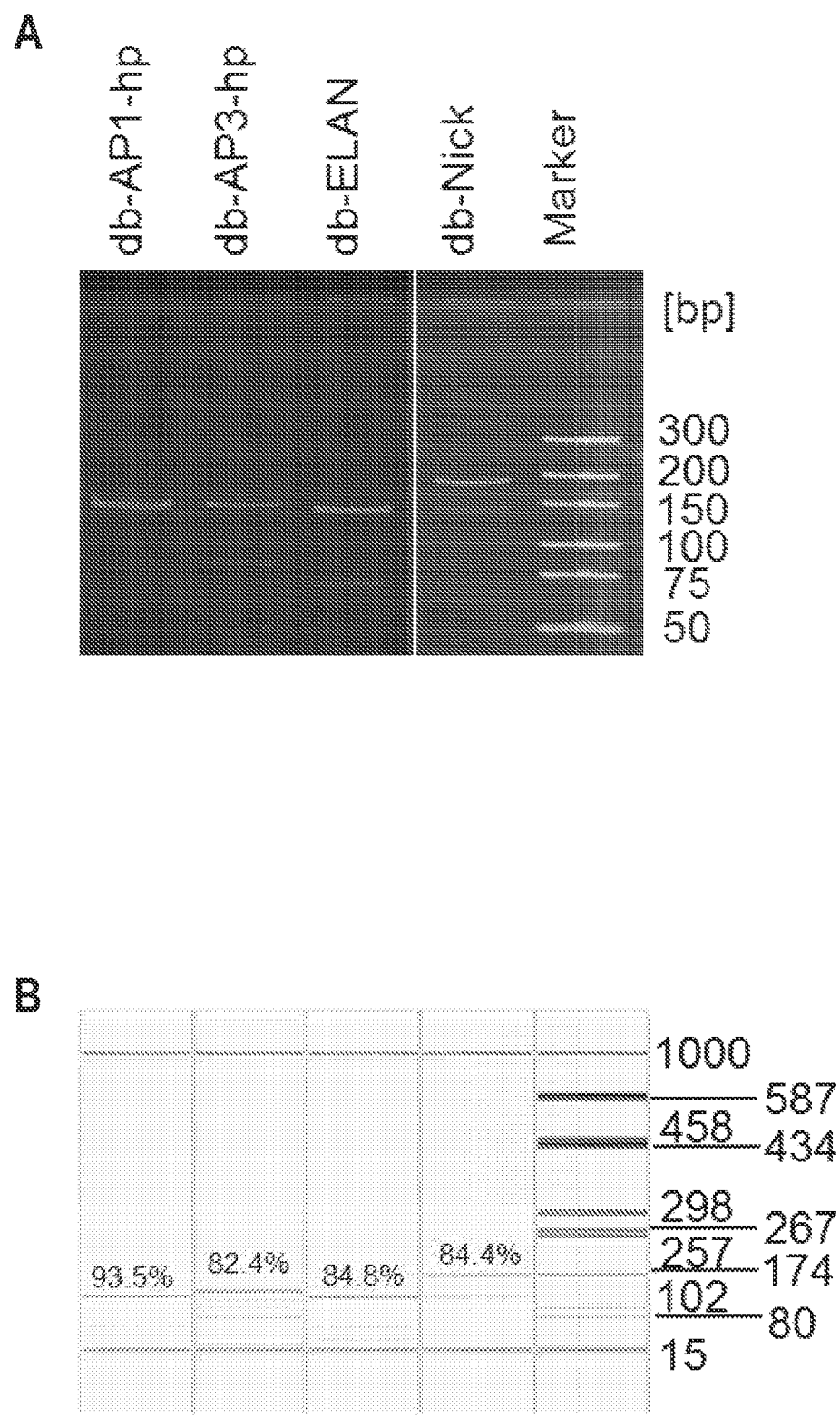
FIG. 14: Purity of dumbbell vectors produced using different technologies. db-AP1-hp and db-AP3-hp: gpPCR-produced dumbbells using primers AP1-hp or AP3-hp; db-ELAN: ELAN-produced dumbbell; db-Nick: egfp-targeting dumbbell produced using the nicking enzyme method. A, 10% PAGE analysis. B, High-resolution capillary gel electrophoresis. The indicated purity in % refers to the total fraction of dumbbell vector DNA in the analysed sample.

Dumbbell purity after exonuclease treatment was investigated using PAGE and high-resolution capillary gel electrophoresis (FIG. 14). Both methods indicate that gap-primer PCR using AP1-hp-primers generates dumbbells with the highest level of purity which was calculated to be 93.5% by the QIAxcel system. AP3-hp gap-primer PCR as well as the ELAN or nicking enzyme methods produced dumbbells with purity levels ranging between 82 to 85%.

We calculated and compared the overall input and expenses for the production of 1 μg dumbbell DNA produced either with the conventional methods or our new strategy (Table 1). Among all investigated protocols including the different gpPCR protocols, AP1-hp-primers generated the most active dumbbells at highest yields and lowest costs. In comparison, both the ELAN and the nicking enzyme method require more and higher amounts of primers and enzymes. A major cost factor involved with the conventional methods is the need for restriction endonucleases. Though gpPCR depends on modified primers, AP1-hp-primer PCR is 10 or 5-fold cheaper compared with the ELAN method and 3.1 or 1.6-fold cheaper compared with the nicking enzyme method, depending on whether the final exonuclease treatment is skipped or not.

EXAMPLE 8

Figure 15:
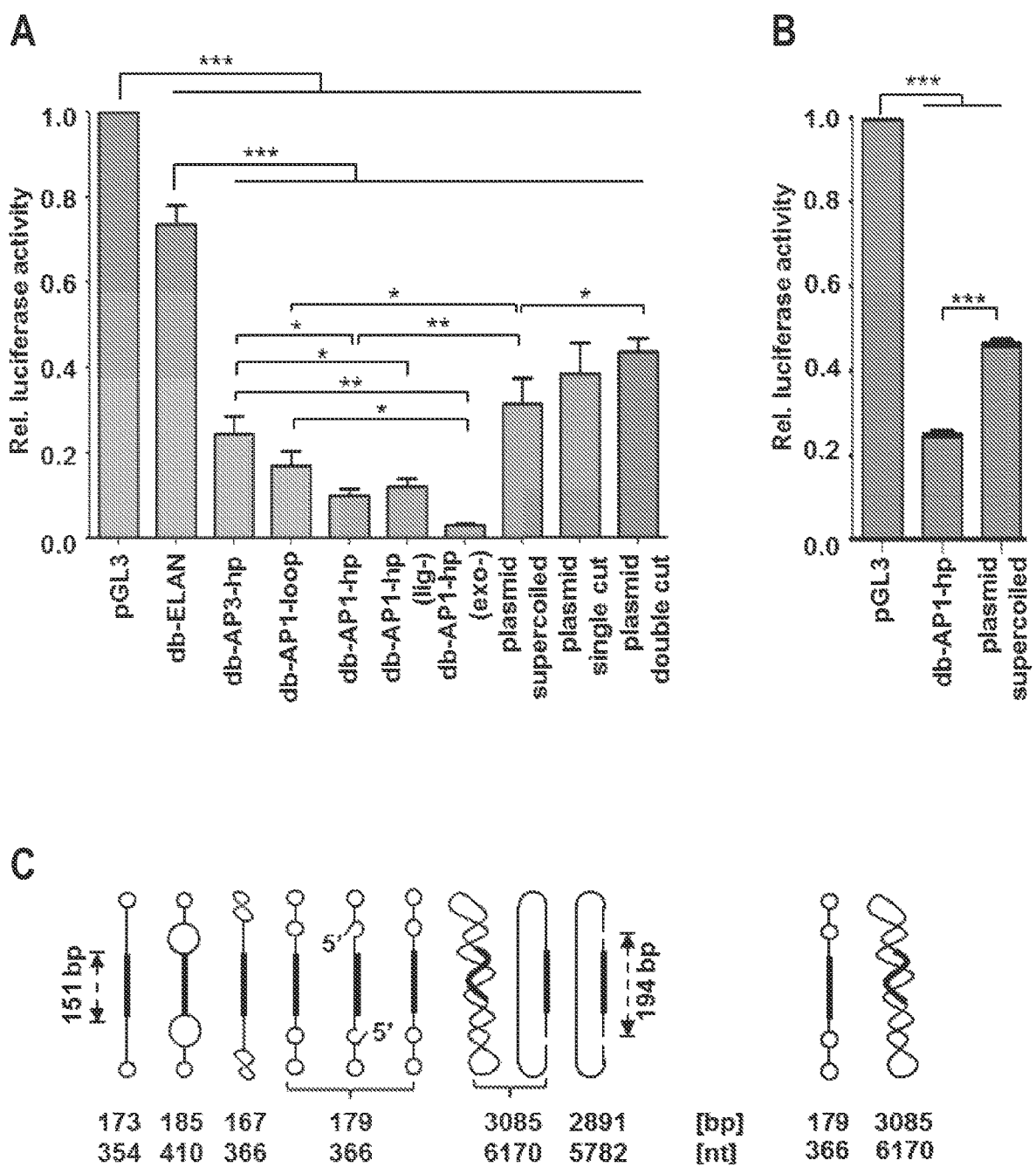
FIG. 15: Luciferase target gene knockdown in HEK293T cells triggered by shRNA expressing dumbbells and plasmids. A, Cells were co-transfected with 90 ng luciferase reporter vector pGL3 and 90 ng (equimass amounts) dumbbell or plasmid DNA. Firefly luciferase expression levels relative to the uninhibited negative control. Values are mean values±SEM of two (d-ELAN) or three (rest) independent experiments. B, Cells were co-transfected with 90 ng luciferase reporter vector pGL3 and 0.5 pmol (equimolar amounts) dumbbell or plasmid DNA. Firefly luciferase expression levels relative to the uninhibited negative control. Values are mean values±SEM of three independent experiments. A and B, the statistical analysis was performed using repeated one-way ANOVA plus a post-hoc Newman-Keuls test. The significance was denoted as * $p<0.001$;  $p<0.01$; * $p<0.05$. C, Structures/topology of the tested DNA vectors. All vectors harbour a 151 bp shRNA expression cassette. Hairpin loops and internal loops within the dumbbell (db) vectors are indicated as circles, i.e. small/large circles indicate small/large loops. All dumbbell vectors were tested after ligation and exonuclease treatment. Vector db-AP1-hp was additionally tested after skipping either the exonuclease treatment (exo-) or both ligation and exonuclease treatment (lig-). The pSuper plasmid vector was tested as supercoiled DNA, after linearization with KpnI (single cut), or after KpnI/BamHI digestion (double-cut). The shRNA expression cassette was contained in the smaller 194 bp KpnI/BamHI fragment. AP1 or AP3 abasic site mimics were counted as 1 or 3 nt, respectively.

Gap-Primer PCR Generated Dumbbells are Superior Compared with Conventionally Produced Dumbbells All dumbbell vectors investigated in this study harbour the expression cassette for a pre-validated firefly luciferase targeting small hairpin RNA (shRNA). We tested the functionality of gpPCR-generated dumbbells, i.e. luciferase knockdown in human tissue culture cells, in comparison with a dumbbell produced using the ELAN method or a pSuper-based plasmid vector, all expressing the same shRNA driven by the minimal H1 promoter (FIG. 15). HEK293T cells were co-transfected with 90 ng of dumbbell or plasmid DNA and 90 ng of the pGL3 luciferase reporter vector and luciferase knock-down was monitored 48 h post transfection (FIG. 15A). Under these conditions, all gpPCR-generated dumbbells and the plasmid vector triggered significantly stronger luciferase knockdown compared with the ELAN-produced dumbbell (db-ELAN; 17% knockdown; $p<0.001$). Strongest knockdown (90%; $p<0.001$) was measured for the AP1-hp-primer-produced dumbbell (db-AP1-hp), followed by the AP1-loop-primer-generated (db-AP1-loop) dumbbell (83%; $p<0.001$), and db-AP3-hp (75%; $p<0.001$). The non-ligated dumbbell db-AP1-hp-(lig$^-$) was with 88% knockdown was almost as effective as its ligated counterpart which might pretend that exonuclease resistance is not that relevant under the assay conditions. However, as db-AP1-hp-(lig$^-$) was not exonuclease treated, it was contaminated by a small quantity the KpnI/BamHI-digested plasmid DNA which served as PCR template for dumbbell production. Hence, the best way to investigate the meaning of exonuclease resistance is to compare db-AP1-hp-(lig⁻) with the ligated but not exonuclease treated DNA db-AP1-hp-(exo⁻). The latter was observed to trigger a substantial stronger knockdown (97%) highlighting the importance of the ligation step. This assumption is further supported by the observation that single- (61% knockdown) or double-digestion (57% knockdown) of the supercoiled plasmid vector (68% knockdown) increasingly impaired its silencing activity. Nevertheless, it is unlikely that the small amount of undigested PCR template, which is not detectable on the gel, considerably contributes to the profound knockdown effect triggered by db-AP1-hp-(exo⁻). Thus, considering the high conversion yields of 92%, the exonuclease step may be skipped for db-AP1-hp production to further simplify the protocol. Considering limitations associated with some delivery strategies such as delivery volumes or toxicity triggered by liposomal compounds, together with the fact that the total mass of DNA that can be delivered can be limited, small db-vectors harbour the advantage that equimass amounts correspond to much higher (here about 17-fold higher) equimolar amounts as compared with larger plasmids. To directly compare the activity of our best dumbbell db-AP1-hp with the corresponding supercoiled plasmid DNA, HEK293T cells were co-transfected with equimolar amounts, i.e. 0.5 pmol, of dumbbell or plasmid and 90 ng of the pGL3 luciferase reporter vector and luciferase knock-down was monitored 48 h post transfection (FIG. 15B). Even under these conditions, db-AP-1-hp triggered significantly ($p<0.001$) stronger luciferase knockdown (74.7%) compared with the plasmid vector (53.7%) highlighting the advantage of the dumbbell size and/or structure.

Figure 16:
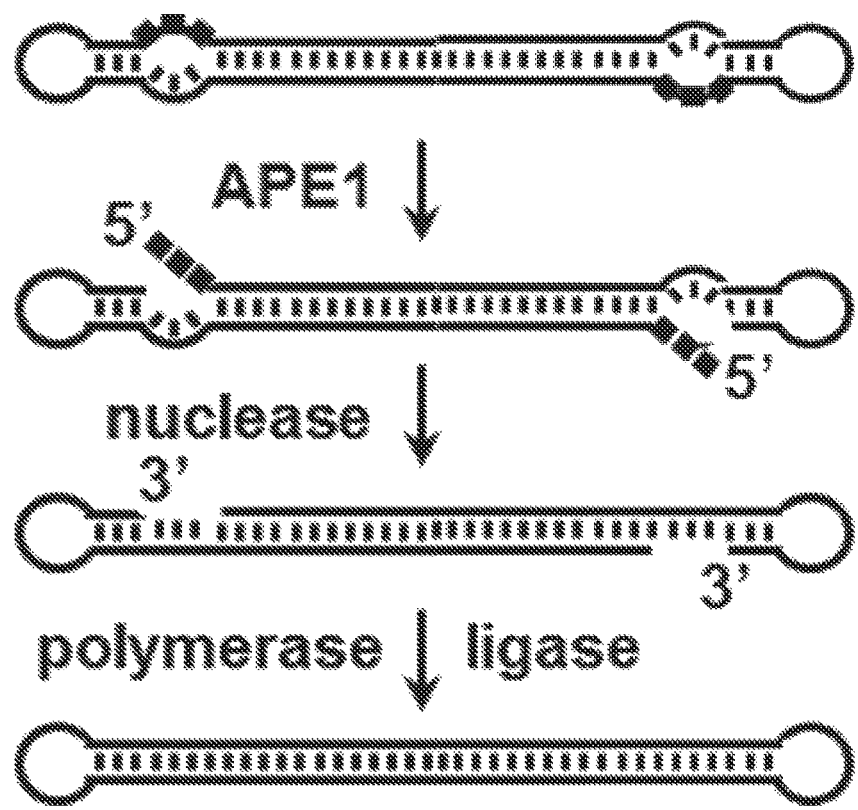
FIG. 16: gpPCR-generated dumbbells harbour abasic sites that trigger the formation of internal loops close to the ends of the dumbbells. Abasic sites can be cleaved by the apurinic/apyrimidinic enzyme 1 (APE1) in human cells prior to base excision and/or nucleotide incision repair.
Figure 17:
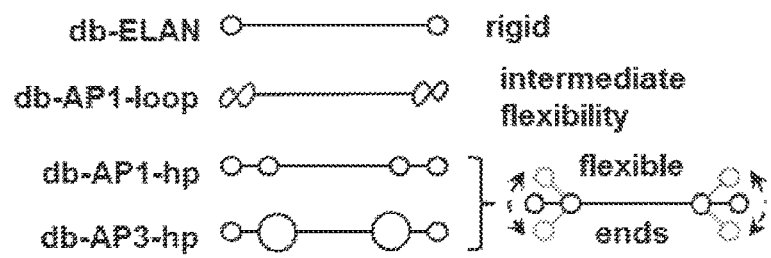
FIG. 17: Model describing facilitated NPC entry by dumbbell vectors with flexible ends. A, Internal loops generated by hairpin-gap-primer PCR trigger increased flexibility of dumbbell ends. B, Rigid dumbbells might enter the NPCs only when approaching them in nearly perpendicular orientation to the nuclear membrane. C, The more flexible ends of the gpPCR-dumbbells could facilitate dumbbell entry into the NPCs even from more oblique angles. D, Dumbbells harbouring small loop might freely pass through the medium-sized NPC channels; however, larger loops may enlarge the DNA effective diameter beyond the cut-off value for passage through midsize NPC meshes, forcing them to enter the nucleus via the much less abundant larger channels.
Figure 17:
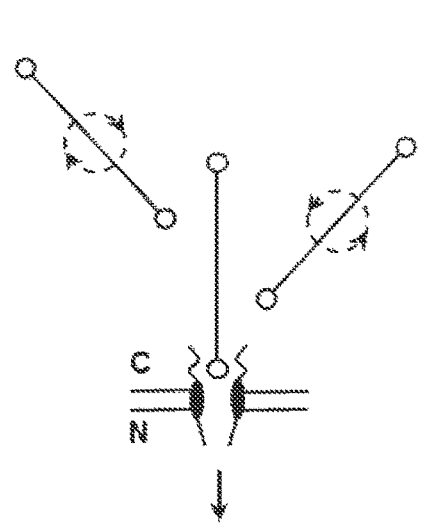
Figure 17:
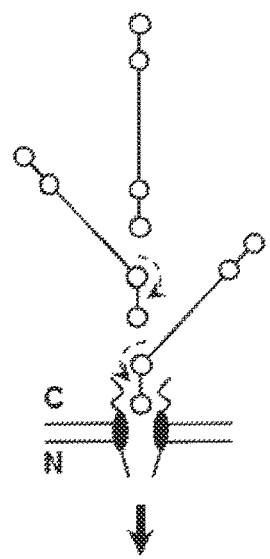
Figure 17:
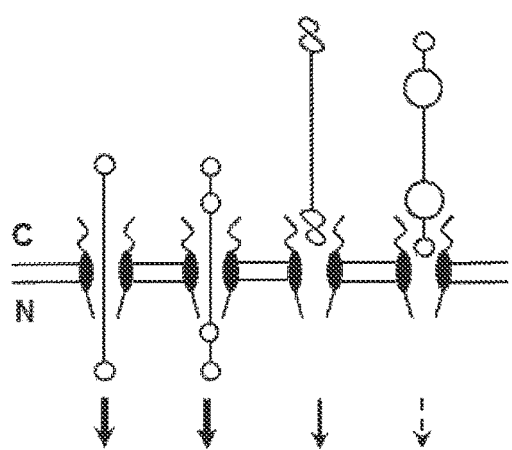

The gpPCR-generated dumbbells triggered significantly ($p<0.001$) stronger knockdown compared with the ELAN-produced dumbbell, the latter of which was equal in size and uses the same expression cassette to transcribe the same shRNA. Thus, the only difference between gpPCR- and ELAN-produced dumbbells relies in a) abasic sites that trigger the formation of b) internal loops close to the ends of the gpPCR-generated dumbbells. Abasic sites are being cleaved by the apurinic/apyrimidinic enzyme 1 (APE1) in human cells prior to base excision and/or nucleotide incision repair (FIG. 16) (43). Thus, these might not be considered advantageous for a genetic vector though the abasic site mimics used in this study, which are lacking the OH-group at the C-1 position of the 2'-deoxyribose, are considerably more stable. The internal loops as well as larger terminal loops, however, trigger increased flexibility of the gpPCR-dumbbell ends (FIG. 17A). While rigid rod-like ELAN-dumbbells might enter the nuclear pore complexes (NPCs) only in nearly perpendicular orientation to the nuclear membrane (FIG. 17B), the more flexible ends of the gpPCR-dumbbells could enable NPC threading even from sub-perpendicular angles, that way accelerating the trajectory through the NPCs (FIG. 17C). A recent study suggested that passive fluxes through NPCs are controlled by channels with three distinct radii of 1.74 nm (78%), 2.63 nm (22%), and 4.32 nm (0.07%) corresponding to diameters of 3.48 nm, 5.26 nm, and 8.64 nm (44). The DNA double-helix effective diameter ($d_{eff}$) in solutions containing the physiological salt concentration was calculated to be 5 nm, which is significantly larger than the geometric diameter of 2 nm (45). That implies that base-paired double-helical DNA can freely pass through the medium-sized NPC channels; however, depending on their size, terminal and internal loops would rapidly enlarge $d_{eff}$ beyond the cut-off value for passage through midsize meshes, thus significantly delaying the nuclear influx. Given a certain minimum size, however, terminal loops are more flexible then internal loops. This model is suitable to explain the reduced activity of dumbbells db-AP3-hp and db-AP3-loop as compared with db-AP1-hp (FIG. 17D).

Figure 18:
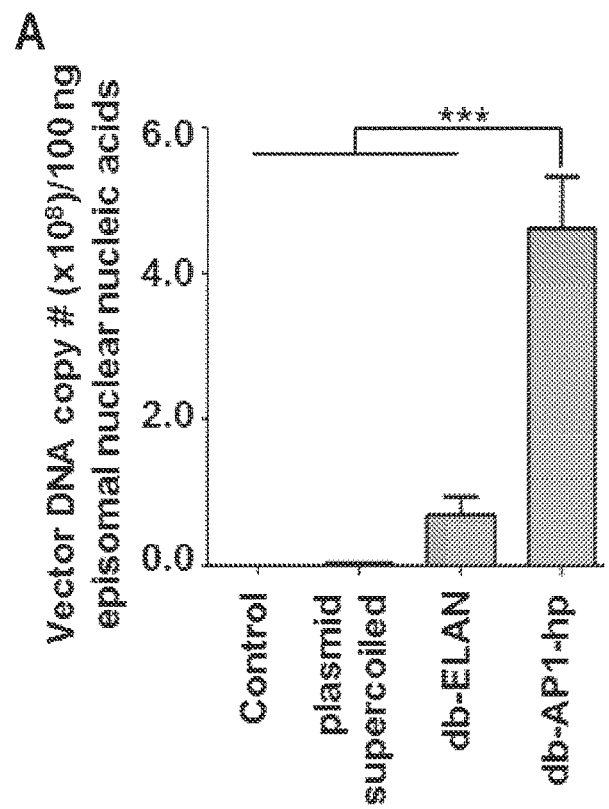
FIG. 18: Nuclear vector delivery (A) and transcriptional vector activity (B) measured by qPCR or qRT-PCR respectively. Values in B refer to the control value 1. Values are mean values±SEM of three independent experiments. The statistical analysis was performed using repeated one-way ANOVA plus a post-hoc Newman-Keuls test. The significance was denoted as * $p<0.001$;  $p<0.01$; * $p<0.05$.
Figure 18:
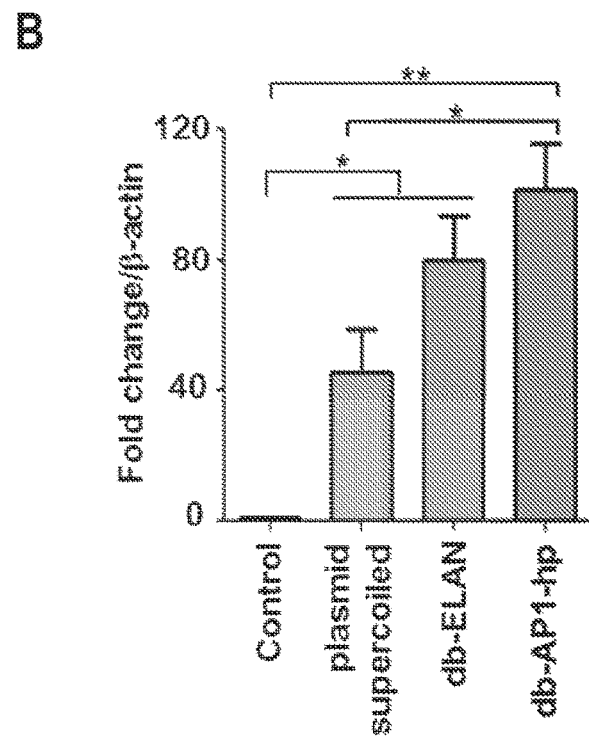

To prove our hypothesis that gpPCR-dumbbells are more efficiently entering cellular nuclei, HepG2 cells were transfected with equimolar (1 pmol) amounts of db-AP1-hp, db-ELAN, or plasmid DNA and both nuclear vector abundance as well as transcriptional vector activity were monitored 24 h post transfection using qPCR (FIG. 18). Since db-vectors and plasmids have different PCR amplification efficiencies, we used individual rtPCR standard curves for the absolute quantification of each of the respective vectors. For example, a db-AP1-hp standard curve was used to quantify db-AP1-hp and so forth. As shown in FIG. 18A, nuclear delivery of the gpPCR-produced dumbbell was 6.4-fold ($p<0.001$) or 94.7-fold ($p<0.001$) enhanced compared with the ELAN-produced dumbbell or the plasmid. The fact that db-AP1-hp entered the nucleus much more efficiently compared with the equally sized db-ELAN indicates that not only the vector size but also the vector structure matters in terms of nuclear delivery. In accordance with the measured nuclear vector abundancies, highest transcriptional activity was detected for db-AP1-hp followed by db-ELAN and the plasmid DNA (FIG. 18B). These findings are consistent with our suggested model that the flexible ends of gpPCR-produced dumbbells might accelerate the trajectory through the nuclear pores. However, one has to keep in mind that the observed nuclear vector abundance is the result of a multi-step process and depends not only on diffusion through the nuclear pores but also on cellular delivery, endosomal escape, cytoplasmic and nuclear DNA stability, and the efficiency of vector DNA isolation from the nuclear compartment. To fully understand the phenomenon of facilitated nuclear targeting by gpPCR-produced dumbbells, more detailed studies of the delivery kinetics will be required.

In summary, our novel two-step gpPCR method produces higher yields of superior dumbbells at lower costs within a shorter period of time. The protocol is scalable and may facilitate large-scale production of RNA or protein expressing dumbbell vectors for pre-clinical and clinical investigation towards efficient and safe genetic therapy. The current focus and future challenge lies in covalent linkage of RNA, peptide or protein helper functions to the loops of the dumbbells for targeted delivery in vivo.

EXAMPLE 9

Dumbbell Vectors Trigger Prolonged Expression of Transgenes in Human Primary Cells Many promising approaches in molecular medicine depend on efficient delivery of recombinant DNA into primary cells ex vivo or in vivo in order to trigger the expression of non-coding RNAs or proteins and subsequently a therapeutic phenotype. These approaches include the genetic therapy of inherited and acquired genetic diseases, genetic vaccination, stem cell programming, somatic cell reprogramming, immunotherapy, and protein expression.

Figure 19:
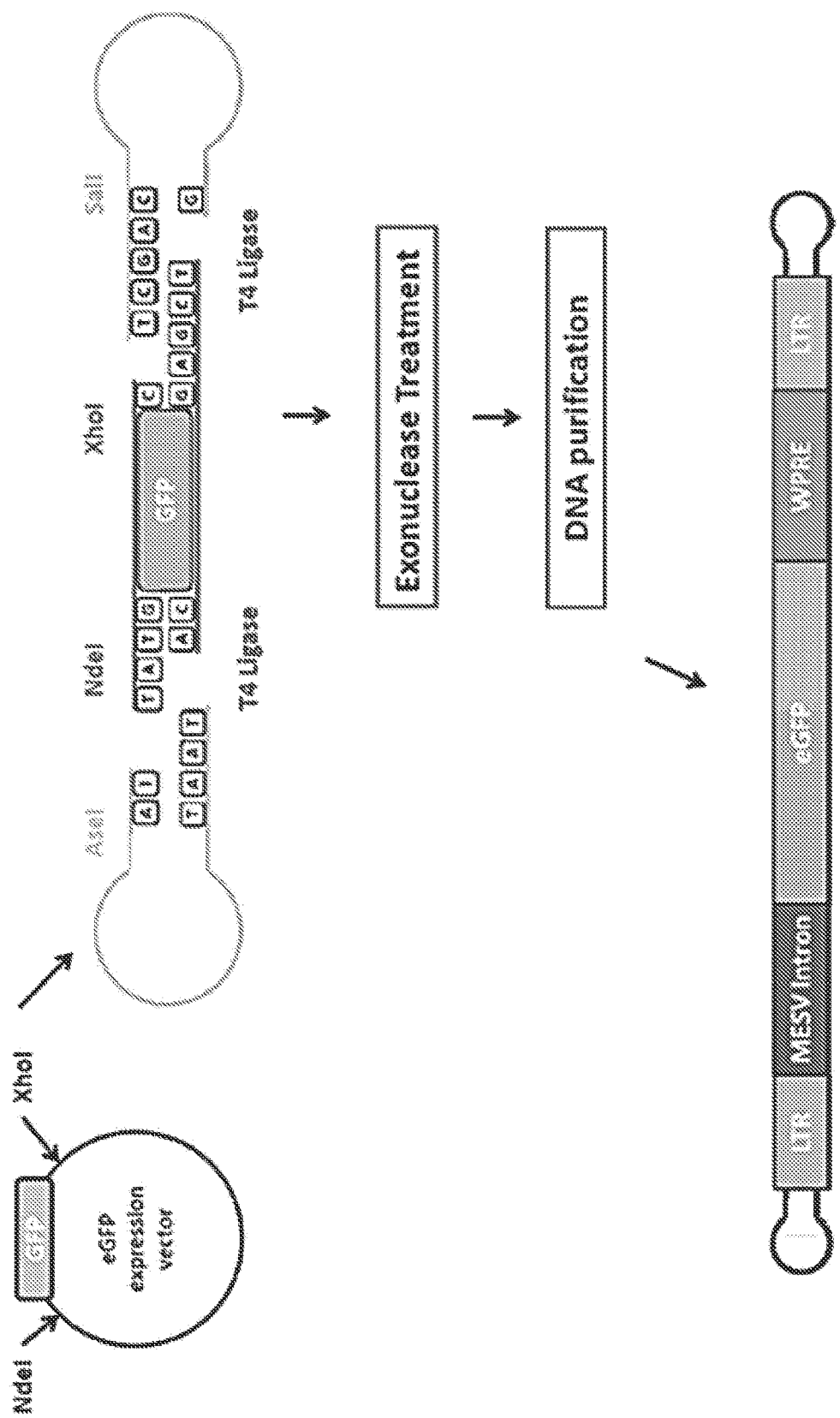
FIG. 19: Scheme of the generation of the dumbbell-shaped DNA vector. The eGFP expression cassette was cut out from an eGFP expression vector using the restriction enzymes NdeI and XhoI. Though the vector used in this example uses a retroviral LTR as promoter, it is not an integrating vector because it lacks the integrase as well as any other coding viral sequences. Subsequently loops were ligated to the eGFP expression cassette using T4 DNA ligase. Ligation was supported by the restriction enzymes which can cleave mis-ligated products but not the correct dumbbell. The dumbbell structure was then purified by exonuclease digestion using DNA polymerase I which protects the covalently closed dumbbell but hydrolyses all unligated DNA.
Figure 20:
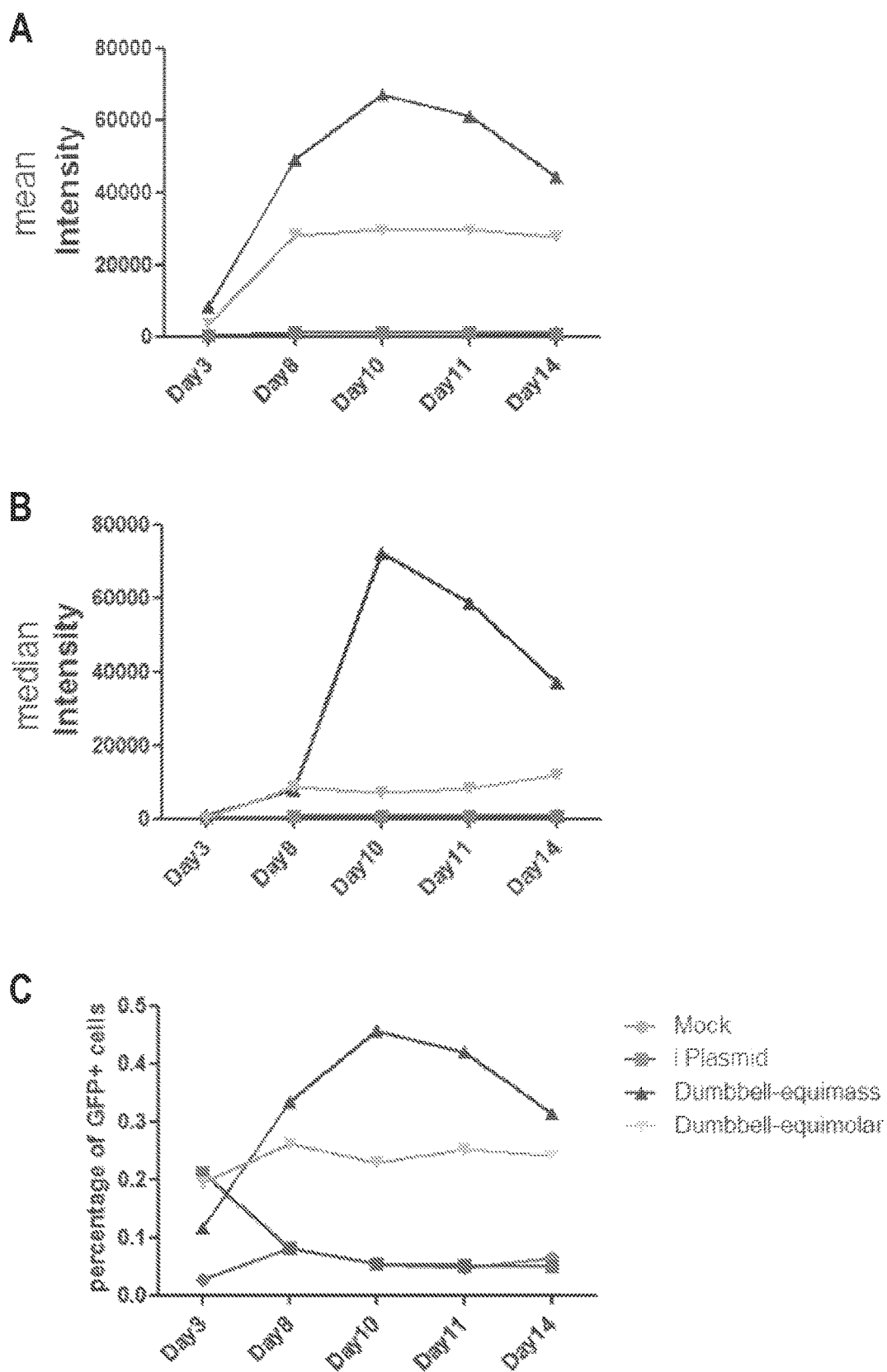
FIG. 20: Sustained eGFP expression in primary human PBMCs triggered by the dumbbell-shaped DNA vector measured using flow cytometry. Equimolar and equimass amounts of the dumbbell vector were compared with the corresponding parental plasmid vector and a buffer control (Mock). A, Mean intensity of eGFP-positive cells; B, median intensity of eGFP-positive cells; C, percentage of eGFP-positive cells.

All state-of-the-art technologies harbor major disadvantages: the expression of conventional naked DNA-based vectors such as plasmids is silenced in primary cells within 24 hours after delivery and RNA-based vectors achieve only short-term effects due the kinetic instability of RNA in living cells or organisms. Sustained transgene expression was only achieved with integrating viral delivery vectors, such as retroviral, lentiviral, or AAV vectors, which harbor severe safety concerns and risks. The dumbbell vector-based technology of this invention enables researchers and clinicians to achieve sustained transgene expression in primary cells without the need to integrate the foreign DNA into the host cell genome. In our example we designed and generated dumbbell-shaped DNA vectors for the expression of the eGFP reporter gene (FIG. 19). This dumbbell-shaped vector was then delivered via nucleofection into primary human PBMCs and subsequently eGFP expression was monitored using flow cytometry analyses (FIG. 20). Sustained expression triggered by the dumbbell-shaped vector could be monitored up to day 14 post delivery after which the primary cells died due to the tissue cell culture conditions. eGFP expression of a conventional plasmid vector containing the identical eGFP expression cassette plus the bacterial sequence backbone was silenced down to mock levels (cells treated with buffer only) within the first two days as reflected by the mean and median eGFP intensities detected by FACS analyses (FIGS. 20A,B). A fraction of cells expressing very low eGFP levels was still detectable in the plasmid sample until day 8 (FIG. 20C). However, the expression levels of these cells were too low to be reflected in the mean and median of expression levels. The presented dumbbell-DNA vector-based system triggers sustained transgene expression in human primary cells representing a promising tool for genetic therapy of human diseases as well as a safe and cheap alternative to viral gene delivery vectors.

EXAMPLE 10

Dumbbell Vectors for RNA-Guided Genome Editing

We designed, generated, and tested dumbbell vectors to deliver the CRISPR/Cas9(n)-mediated RNA-guided genome editing system into human cells for reversal of Glucose-6-phosphate dehydrogenase (G6PD) deficiency.

RNA-guided genome editing is based on RNA-mediated adaptive defense systems evolved from bacteria and archaea (46-49) termed clustered regulatory interspaced short palindromic repeats (CRISPR)/CRISPR-associated (Cas) systems which originally use short RNAs to direct degradation of foreign invading DNA originating from viruses or plasmids. The most popular system is the *Streptococcus pyogenes* (SP) type II CRISPR system. For editing of genomic DNA in human cells several system adaptations were made: 1. The originally distinct two short RNA molecules, called CRISPR RNA (crRNA) and trans-activating crRNA (tracrRNA), necessary to guide the enzyme to the DNA target in order to trigger cleavage were fused to form a single guide RNA (gRNA). The scaffolding tracrRNA domain, hereinafter referred to as Cas-interacting domain, can be fused to any crRNA domain, hereinafter referred to as DNA binding domain (BD) (50). 2. Codon optimization converted the SPCas9 into the hSPCas9 (51). 3. To reduce off-target editing, an aspartate-to-alanin substitution (D10A) was introduced to convert the DNA double-strand break (DSB) triggering hSPCas9 into the DNA nickase hSPCas9n (9). The DNA binding domain (20 to 17 nt in length) of the gRNA can now guide the gRNA-Cas9 complex to complementary/homologous DNA sites termed protospacer, hereinafter referred to as DNA target site, which has to be followed 3' by a second short identifier called PAM (protospacer adjacent motif) which is 5'-NGG for the system described here. The BD of the gRNA can overlap with the site to be edited, or should alternatively be in proximity to this site. hSPCas9 complexes will then trigger DSBs, hSPCas9n complexes trigger nicks. Two hSPCas9n complexes with different gRNAs and shifted target sites will be required to trigger a double nick. DSBs including double nicks induced by Cas9 or Cas9n will then activate one of two endogenous repair mechanisms: 1. In the error-prone non-homologous end-joining (NHEJ) pathway, the ends will be processed and rejoined which can result in random insertion/deletion (indel) mutations. 2. Alternatively, a repair template in form of a plasmid, PCR product or single-stranded oligodeoxyribonucleotides (termed oligonucleotides in the following) can be supplied to leverage the homology-directed repair (HDR) pathway triggering high fidelity, precise editing. Single nicks trigger HDR using the intact strand as template. Beauty and simplicity of this technology, as opposed to transcription activator-like effector nucleases (TALENs) or zinc-finger nucleases (ZFNs), are given by the facts that (i) genomic target site selection is determined solely by base-complementarity to the gRNA and the optimized enzyme does not require further reengineering, (ii) higher targeting efficiencies (repair rates in the range of up to several ten %), and (iii) the possibility to perform multiplex genome editing (9,52).

Red blood cell disorders also termed erythrocytic abnormalities (EAs) are the most prevalent inherited disorders worldwide. In particular, Southeast (SE) Asia bears a considerable burden of heritable EAs, which in most cases adversely affect normal human development and life span. The only cure has been the transplantation of bone-marrow cells (BMCs) from foreign donors whose success depends on the limited availability of suitable donors. Therapies based on genetic correction of a patient's own BMCs using state-of-the-art viral delivery vectors have shown promise, however its clinical application is limited by the alarming possibility of uncontrolled genomic vector integration. Thus there is a pressing need to develop gene therapies that are both safe and efficient. We developed dumbbell-shaped DNA minimal vectors to deliver the CRISPR/Cas9(n) genome editing technology into human tissue culture cells and cord blood stem cells (HSCs) isolated from patients to cure an important SE Asian EA, the Glucose-6-phosphate dehydrogenase deficiency.

RNA-guided genome editing requires the CRISPR/Cas9 (n) components to be expressed for a sufficient but limited period of time. While plasmid vectors are suitable due to rapid transgene silencing in primary cells, lentiviral vectors irreversibly change the host cell genome offside the intended editing site. Dumbbell vectors trigger prolonged gene expression in primary cells and do not interfere with the target cell genome and, hence, are most suitable to deliver RNA-guided genome editing into primary including human primary cells.

Figure 21:
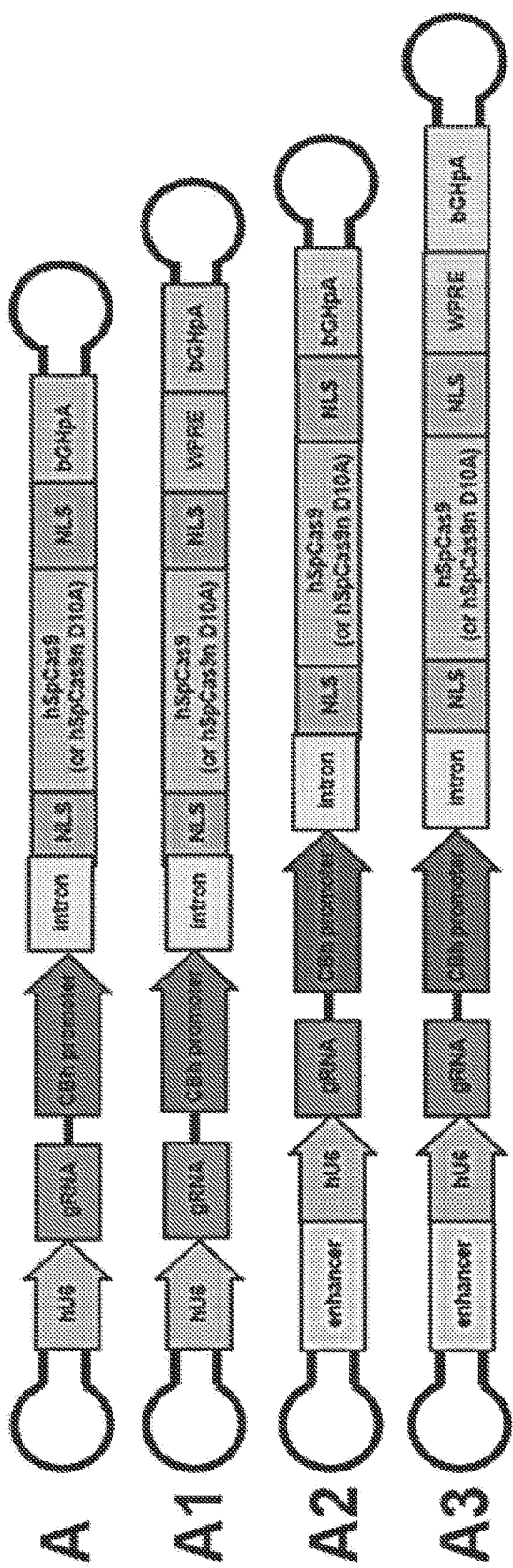
FIG. 21: Design of db-vectors for RNA-guided genome editing. A, Basic vector expressing one gRNA and either Cas9 or Cas9n. Two vectors expressing different gRNAs are needed if the nickase is used. Basic vector equipped with WPRE (A1), an enhancer/nuclear targeting signal (A2), or both functional elements (A3). B, Nickase vector with two gRNA genes. Nickase vectors following designs C1 to D2 will also be tested with two gRNA genes. C1/C2, vector as A to B including the double-stranded DNA donor template upstream/downstream of the caspase gene. D1 and D2, vectors harboring a single-stranded donor template embedded in one of the respective terminal loops. E, vector amalgamating all functional elements/those confirmed to improve genome editing activity.
Figure 21:
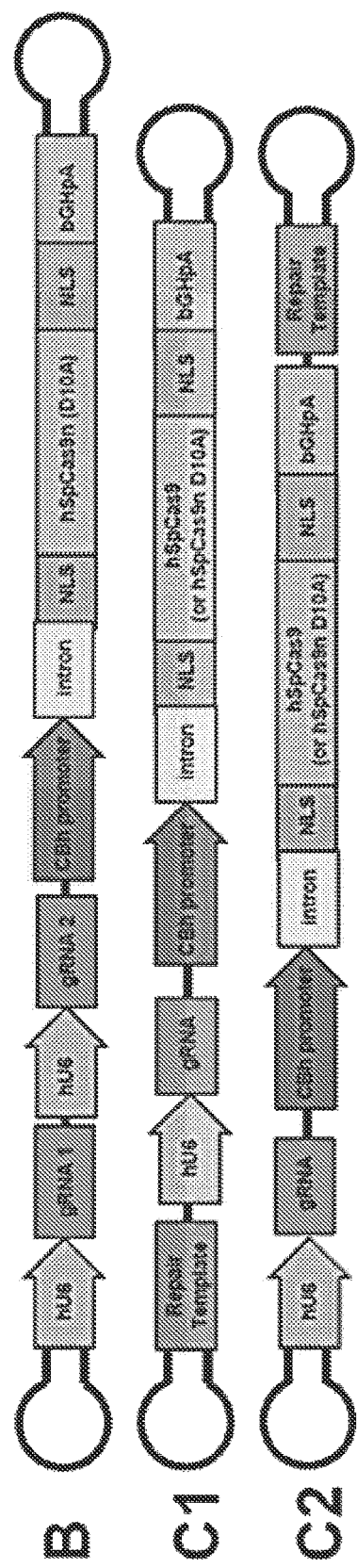
Figure 21:
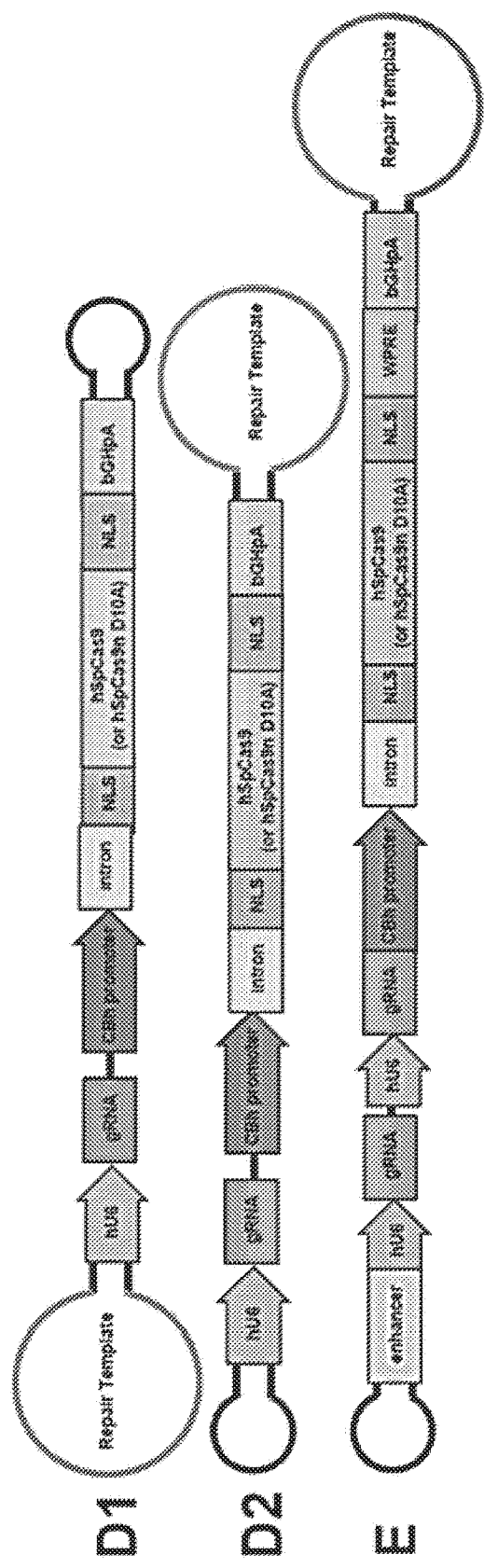

We demonstrated that distinct molecular features can enhance the expression of coding and non-coding genes from db-vectors. We considered these features to design vectors which show strongest expression of hSPCas9(n). The basic dumbbell is composed of the gRNA and hSPCas9 (n) expression cassettes of vectors pX330 and pX335 (9), containing the gRNA under control of the human U6 (hU6) promoter, followed by the CBh promoter, an modified MVM intron 3, the hSPCas9(n) coding sequence flanked by two nuclear localization signals, and the bGHpA (bovine growth hormone) polyadenylation signal (FIG. 21, construct A). We fused the Woodchuck hepatitis virus posttranscriptional regulatory element (WPRE) to the mRNA 3' end for facilitated mRNA processing, enhanced nuclear RNA export, and gene expression (construct A1) (53). Secondly, we included the SV40 enhancer sequence or truncated versions thereof to support promoter function and/or trigger active nuclear import of the db-vectors (construct A2). Finally, we designed a vector harboring both WPRE and SV40 enhancer to achieve maximum synergistic effects on gene expression (construct A3). Applications involving the nickase enzyme require the expression of two different gRNAs which are usually expressed from two distinct vectors. We designed db-vectors harboring expression cassettes for the nickase and two gRNAs (construct B). The DNA repair templates required for homologous recombination are usually co-delivered as separate DNA molecules (ssDNA or dsDNA) together with the Cas9 and gRNA(s). Vectors unifying all three components, the gRNA gene(s), the Cas9 enzyme, and the repair template have not been described yet, presumably because dsDNA templates can be cleaved due to the high degree of homology with the genomic DNA target sequence. Single-stranded DNA repair templates, however, are no substrate of the Cas9 enzymes. Hence the unique structure of the db-vectors will allowed us to implement non-cleavable single-stranded repair templates of about 80 nt or longer in the terminal loop structures of the dumbbells (constructs D1 & D2). For comparison we also designed db-vectors containing dsDNA repair templates of 1 kb in length (constructs C1 & C2). Finally, we designed db-vectors amalgamating computationally designed gRNAs with all molecular features found to support the overall genetic editing efficiency (e.g. construct E). Neither Cas9/CRISPR-based reversal of EAs nor db-vector-based Cas9/CRISPR nor any of the molecular dumbbell features to be investigated in this work have ever been tested before.

Figure 22:
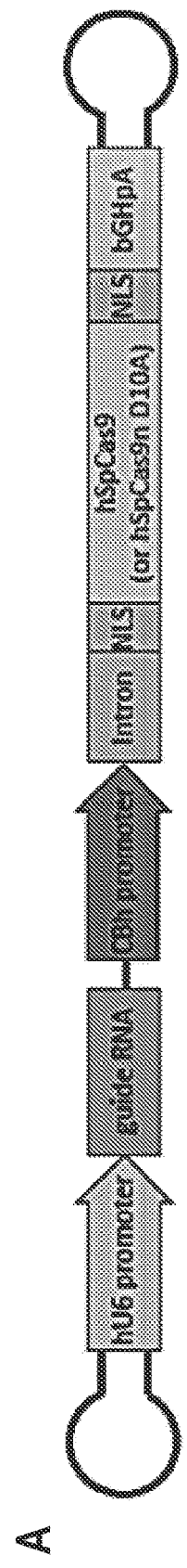
FIG. 22: Design and generation of dumbbell vector for CRISPR/Cas-based RNA-guided genome editing. A, Basic dumbbell vector as described in FIG. 12 expressing one G6PD-Mahidol-targeting gRNA and either Cas9 or Cas9n. Generation of Cas9 or Cas9n-expressing dumbbells harbouring different guide RNAs using the ELAN method before (B) or after (C) exonuclease treatment. Ethidium bromide stain of 1% agarose gel.
Figure 22:
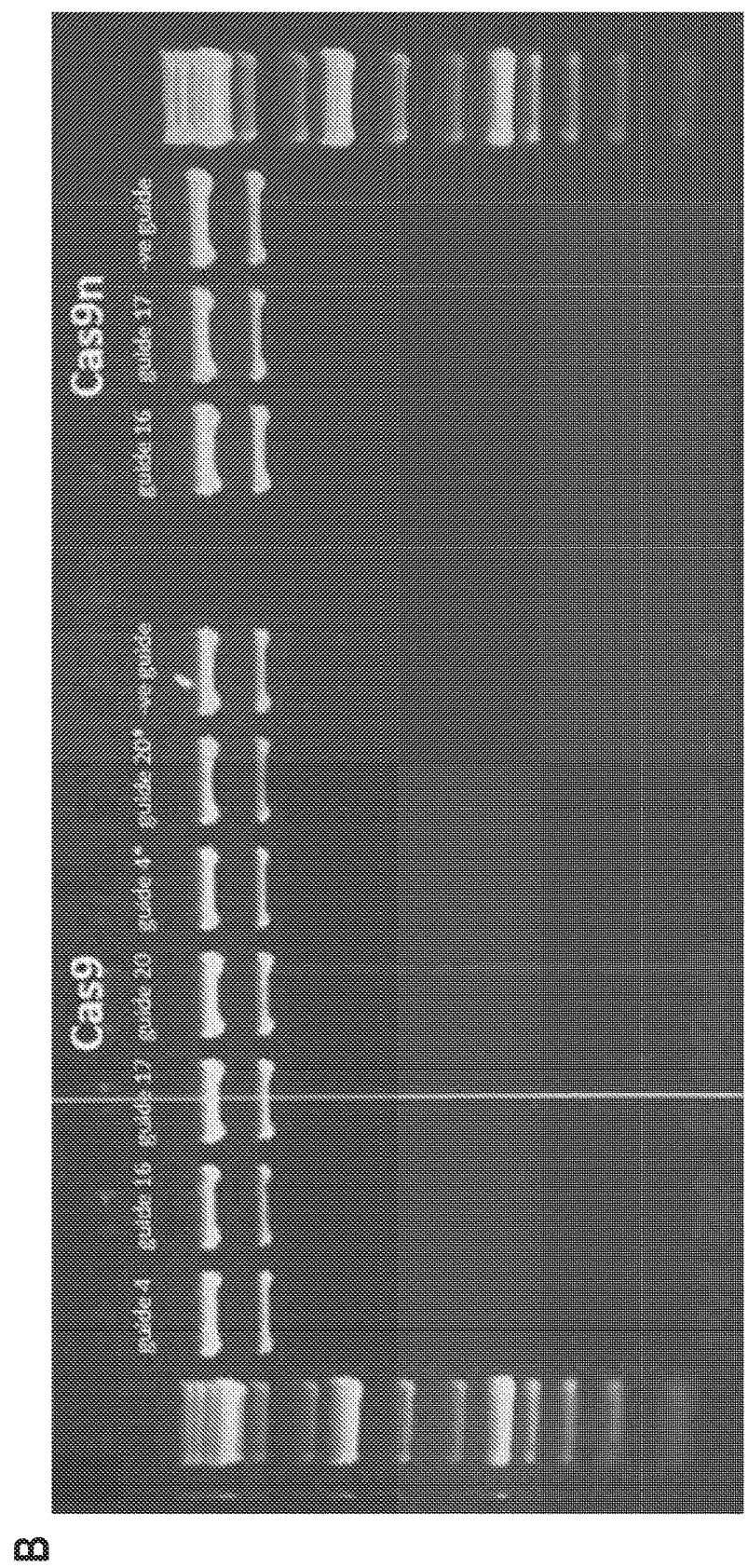
Figure 22:

Dumbbell construct A was generated from corresponding plasmid DNA using an optimized ELAN protocol (FIG. 22). Before exonuclease treatment, the ligation products showed a 5.6 kb band corresponding to the desired dumbbells, and bands at 2.8 kb and 180 bp corresponding to the EheI-cleaved plasmid backbone (FIG. 22B). Following exonuclease treatment, the 5.6 kb band remained while the 2.8 kb and 180 bp bands were no longer present (FIG. 22C) as expected. The expected 5.6 kb products corresponded to the exonuclease-resistant dumbbell vectors generated from pX330-MCS and pX335-MCS (FIG. 22C).

Figure 23:
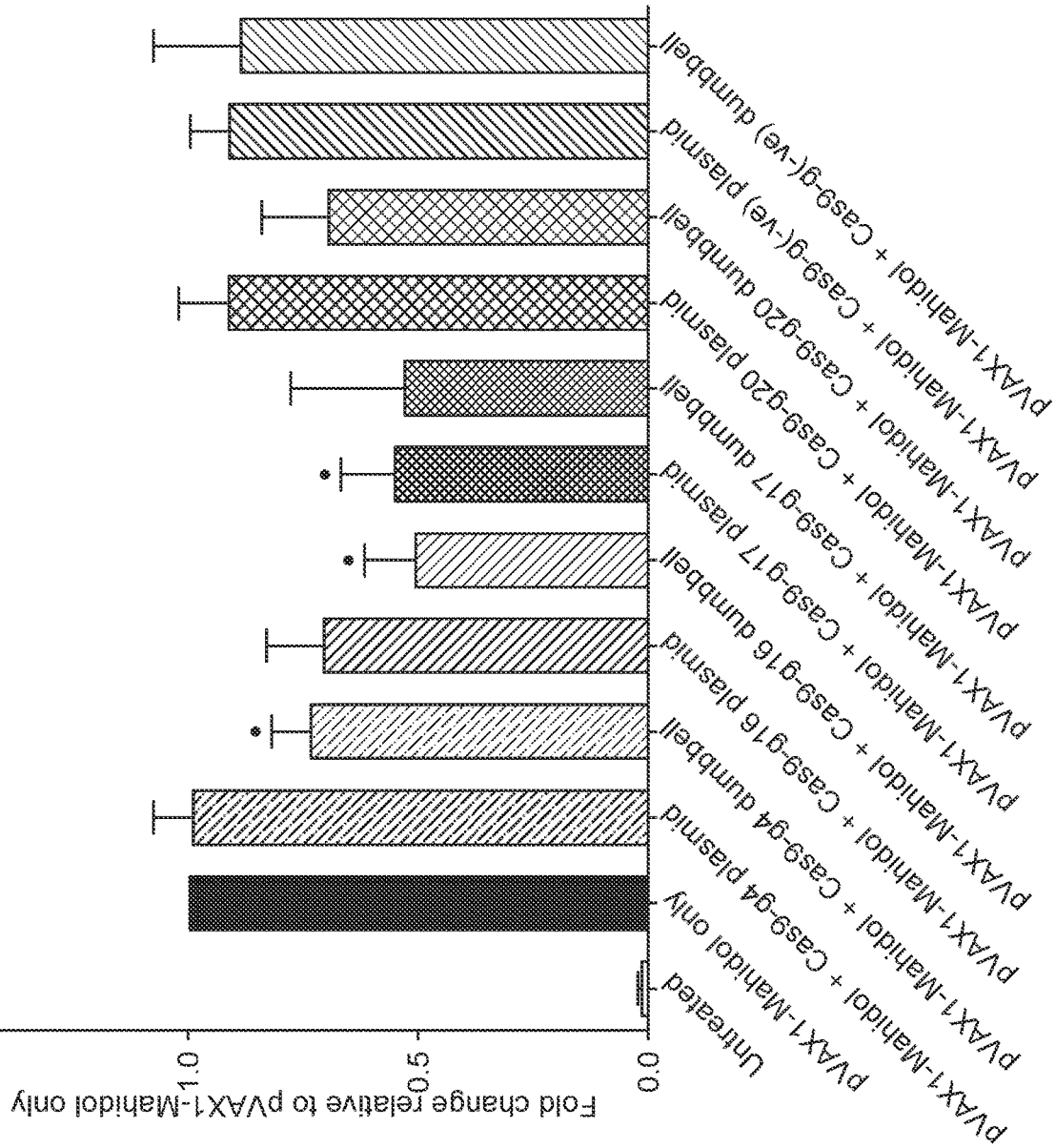
FIG. 23: A, Cutter assay results for Cas9 editing. Real-time PCR relative quantification of remaining intact pVAX1-Mahidol in episomal DNA extract after co-transfection with Cas9-exressing plasmid or dumbbell constructs in 293T cells, with respect to pVAX1-Mahidol-only control. g4/g16/g17/g20: guide sequence candidates. g(-ve): universal negative control guide sequence, which does not bind the target region but still gives rise to a guide RNA transcript folding the necessary secondary structure for Cas9 recruitment. Guide RNAs containing guide sequences 4, 16 and 17 were found to be effective cutters, when used in conjunction with wild type Cas9. (*: $p<0.05$, two-tailed t-test, n=3; error bars represent SEM). B, PCR-RFLP qualitative analysis of reversal of G6PD-Mahidol mutation in 293T episome. A 104 bp fragment of G6PD exon 6 was PCR amplified using a mutagenic primer pair. If the template carries the G6PD-Mahidol mutation, the amplicon is cut by subsequent HindIII restriction digestion, showing two bands at 88 bp and 22 bp. If the template is WT (repaired), the amplicon is not cut, and the single 104 bp band remains. All samples run in pairs; uncut on left lane and HindIII digested on right lane. +ve: positive control treated with only the WT repair target plasmid. -ve: negative control treated with only pVAX1-Mahidol. p: plasmid; db: dumbbell. Appearance of 104 bp bands (arrowed) on 'cut' lanes of Cas9-g4, Cas9-g16, Cas9-g17 and Cas9n-g16+g17 pair plasmid and dumbbell treated samples indicate successful repair of the G6PD-Mahidol point mutation on the episomal target—however only qualitatively. (3% agarose, EtBr stained).
Figure 23:
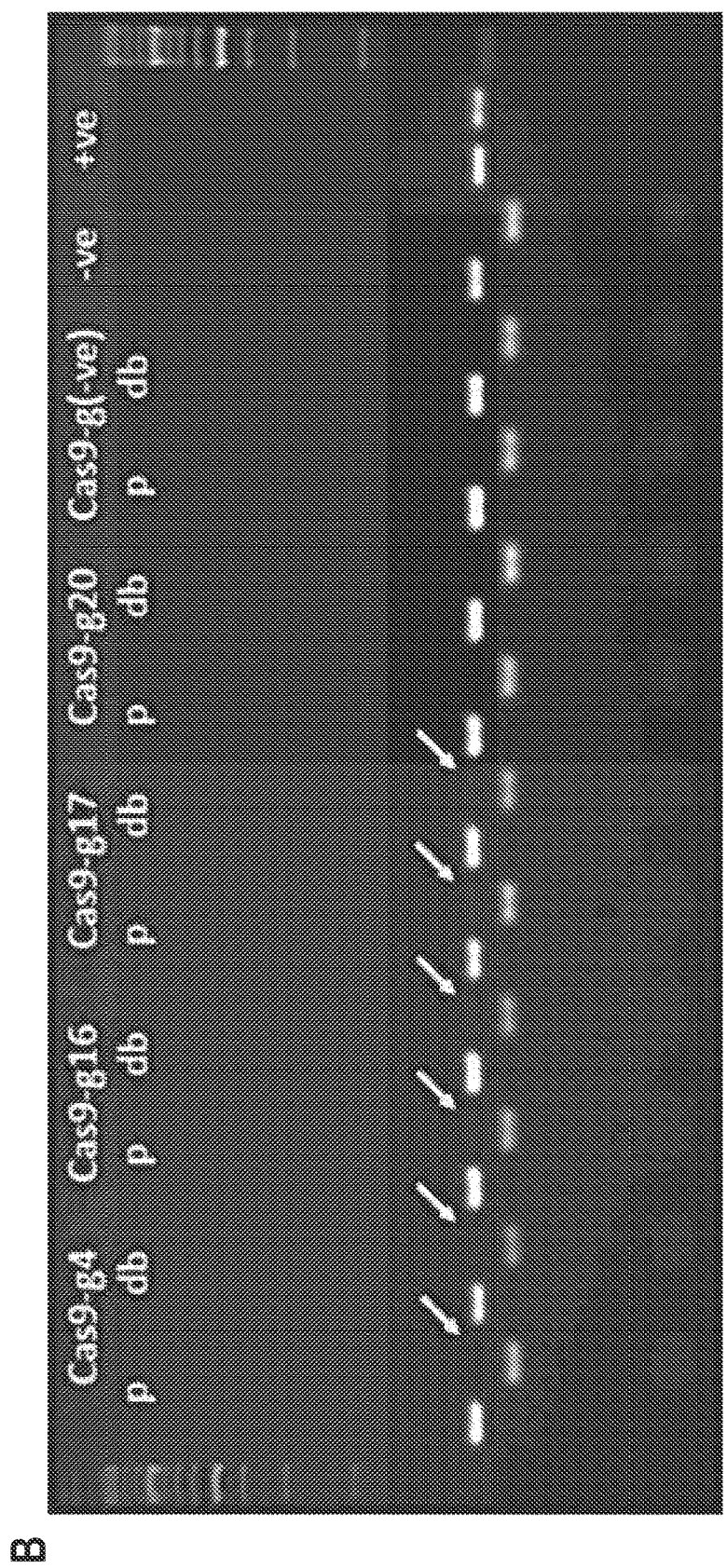

We performed a 'cutter assay' to investigate the target cleavage activities. Therefore, 293T cells were co-transfected with the pVAX plasmid harbouring the G6PD Mahidol mutation as a target site and equimolar amounts of either a dumbbell vector or the corresponding plasmid expressing different guide-RNAs (g4, g16, g17, and g20). Episomal DNA was isolated and target cleavage was quantified using qPCR (FIG. 23A). Compared to the plasmid vectors, dumbbells showed enhanced CRISPR/Cas9-triggered target DNA cleavage.

Next we measured reversal of the G6PD Mahidol mutation on episomal plasmid target DNA in human tissue culture cells. PCR-RFLP qualitative analysis of episomal DNA extracts revealed successful editing of the G6PD-Mahidol mutation on the pVAX1-Mahidol repair target, to the wild-type sequence in 293T cells after 24 hours (FIG. 23B). Repair was observed in cells treated with the Cas9-g4, Cas9-g16 and Cas9-g17 plasmids and dumbbells. For Cas9-g4 constructs, dumbbell-triggered editing was more efficient than plasmid-triggered editing. As expected, no detectable repair was observed with any of the constructs bearing the universal negative guide sequences.

REFERENCES

1. Paul W E (2008). Fundamental Immunology. Philadelphia, Wolters Kluwer/Lippincott Williams & Wilkins.
2. Murphy K, Travers P, Walport M, Janeway C (2012). Janeway's immunobiology. New York, Garland Science.
3. Wagner R W, Matteucci M D, Grant D, Huang T, Froehler B C (1996). Potent and selective inhibition of gene expression by an antisense heptanucleotide. *Nat Biotechnol* 14, 7, 840-4.
4. Jung U, Jiang X, Kaufmann S H E, Patzel V (2013). A universal stem-loop primer-based TaqMan RT-PCR protocol for cost efficient detection of small non-coding RNA. *RNA* 19, 1864-73.
5. Myslinski E, AméJ-C, Krol A, Carbon P (2001). An unusually compact external promoter for RNA polymerase III transcription of the human H1RNA gene. *Nucleic Acids Res.* 29, 2502-9.
6. Taki M, Kato Y, Miyagishi M, Takagi Y, Sano M, Taira K (2003). A direct and efficient synthesis method for dumbbell-shaped linear DNA using PCR in vitro. *Nucleic Acids Res Suppl* 3, 191-2.
7. Taki M, Kato Y, Miyagishi M, Takagi Y, Taira K (2004). Small-interfering-RNA expression in cells based on an efficiently constructed dumbbell-shaped DNA. *Angew Chem Int Ed Engl* 43, 24, 3160-3.
8. Cost G J (2007). Enzymatic ligation assisted by nucleases: simultaneous ligation and digestion promote the ordered assembly of DNA. *Nat Protoc* 2, 9, 2198-202.
9. Cong L, Ran F A, Cox D, Lin S, Barretto R, Habib N, Hsu P D, Wu X, Jiang W, Marraffini L A, Zhang F (2013). Multiplex genome engineering using CRISPR/Cas systems. *Science* 339, 6121, 819-23.
10. Zuker M (2003). Mfold web server for nucleic acid folding and hybridization prediction. *Nucleic Acids Res* 31, 13, 3406-15.
11. Zeng Y, Wagner E J, Cullen B R (2002). Both natural and designed micro RNAs can inhibit the expression of cognate mRNAs when expressed in human cells. *Mol Cell* 9, 6, 1327-33.
12. Schakowski F, Gorschluter M, Junghans C, Schroff M, Buttgereit P, Ziske C, Schottker B, Konig-Merediz S A, Sauerbruch T, Wittig B, Schmidt-Wolf I G (2001). A novel minimal-size vector (MIDGE) improves transgene expression in colon carcinoma cells and avoids transfection of undesired DNA. *Mol Ther* 3, 5 Pt 1, 793-800.
13. Schakowski F, Gorschluter M, Buttgereit P, Marten A, Lilienfeld-Toal M V, Junghans C, Schroff M, Konig-Merediz S A, Ziske C, Strehl J, Sauerbruch T, Wittig B, Schmidt-Wolf I G (2007). Minimal size MIDGE vectors improve transgene expression in vivo. *In Vivo* 21, 1, 17-23.
14. Grimm D, Streetz K L, Jopling C L, Storm T A, Pandey K, Davis C R, Marion P, Salazar F, Kay M A. (2006). Fatality in mice due to oversaturation of cellular microRNA/short hairpin RNA pathways. *Nature* 441, 7092, 537-41.
15. Liang L, Wong C M, Ying Q, Fan D N, Huang S, Ding J, Yao J, Yan M, Li J, Yao M, Ng I O, He X (2010). MicroRNA-125b suppressesed human liver cancer cell proliferation and metastasis by directly targeting oncogene LIN2862. *Hepatology* 52, 5, 1731-40.
16. Jia H Y, Wang Y X, Yan W T, Li H Y, Tian Y Z, Wang S M, Zhao H L (2012). MicroRNA-125b Functions as a Tumor Suppressor in Hepatocellular Carcinoma Cells. *Int J Mol Sci* 13, 7, 8762-74.
17. Dean D A (1997). Import of Plasmid DNA into the Nucleus Is Sequence Specific. *Experimental Cell Research* 230, 293-302.

18. Dean D, Dean B, Muller S, Smith L (1999). Sequence Requirements for Plasmid Nuclear Import. *Experimental Cell Research* 253, 713-22.
19. Vacik J, Dean B S, Zimmer W E, Dean D A (1999). Cell-specific nuclear import of plasmid DNA. *Gene Therapy* 6, 1006-14.
20. Miller A M, Dean D A (2008). Cell-specific nuclear import of plasmid DNA in smooth muscle requires tissue-specific transcription factors and DNA sequences. *Gene Ther* 15, 15, 1107-15
21. Längle-Rouault F, Patzel V, Benavente A, Taillez M, Silvestre N, Bompard A, Sczakiel G, Jacobs E, Rittner K (1998). Up to 100-Fold Increase of Apparent Gene Expression in the Presence of Epstein-Barr Virus oriP Sequences and EBNA1: Implications of the Nuclear Import of Plasmids. *Journal of Virology* 72, 6181-5.
22. Miller A, Dean D (2009). Tissue-specific and transcription factor-mediated nuclear entry of DNA. *Advanced Drug Delivery Reviews* 61, 603-13.
23. Krützfeldt J, Rajewsky N, Braich R, Rajeev K G, Tuschl T, Manoharan M, Stoffel M (2005). Silencing of microRNAs in vivo with 'antagomirs'. *Nature* 438. 7068. 685-9
24. Chabot S, Orio J, Castanier R, Bellard E, Nielsen S J, Golzio M, Teissie J (2012). LNA-based oligonucleotide electrotransfer for miRNA inhibition. *Mol Ther* 20, 8, 1590-8.
25. Meng F, Henson R, Wehbe-Janek H, Ghoshal K, Jacob S T, Patel T (2007). MicroRNA-21 regulates expression of the PTEN tumor suppressor gene in human hepatocellular cancer. *Gastroenterology* 133, 647-58.
26. Patzel V, Sczakiel G (1998). Theoretical design of antisense RNA structures substantially improves annealing kinetics and efficacy in human cells. *Nature Biotechnology* 16, 1, 64-8.
27. Patzel V (2004). In silico design of functional RNA molecules. *Curr Opin Drug Discov Dev* 7, 3, 360-9.
28. Patzel V, Sczakiel G (2000). In vitro selection supports the view of a kinetic control of antisense RNA-mediated inhibition of gene expression in mammalian cells. *Nucleic Acids Res.* 28, 13, 2462-6.
29. Patzel V, Sczakiel G (1999). Length dependence of RNA-RNA annealing. *J. Mol. Biol.* 294, 1127-34.
30. Lehmann M J, Patzel V, Sczakiel G (2000). Theoretical design of antisense genes with statistically increased efficacy. *Nucleic Acids Res* 28, 13, 2597-604.
31. Schirmbeck R, Konig-Merediz S A, Riedl P, Kwissa M, Sack F, Schroff M, Junghans C, Reimann J, Wittig B (2001). Priming of immune responses to hepatitis B surface antigen with minimal DNA expression constructs modified with a nuclear localization signal peptide. *J Mol Med* (Berl) 79, 5-6, 343-50.
32. Brinster R L, Allen J M, Behringer R R, Gelinas R E, Palmiter R D (1988). Introns increase transcriptional efficiency in transgenic mice. *Proc Natl Acad Sci USA* 85, 3, 836-40.
33. Mansfield S G, Chao H, Walsh C E (2004). RNA repair using spliceosome-mediated RNA trans-splicing. *Trends Mol Med* 10, 6, 263-8.
34. Kim J H, Lee S R, Li L H, Park H J, Park J H, Lee K Y, Kim M K, Shin B A, Choi S Y (2011). High cleavage efficiency of a 2A peptide derived from porcine teschovirus-1 in human cell lines, zebrafish and mice. *PLoS One* 6, 4, e18556.
35. Beltinger C, Fulda S, Kammertoens T, Meyer E, Uckert W, Debatin K M (1999). Herpes simplex virus thymidine kinase/ganciclovir-induced apoptosis involves ligand-independent death receptor aggregation and activation of caspases. *Proc Natl Acad Sci USA* 96, 15, 8699-704.
36. Jiang Y X, Lu Y, Liu T J, Yang J, Chen Y, Fang Y W (2011). Using HSV-TK/GCV suicide gene therapy to inhibit lens epithelial cell proliferation for treatment of posterior capsular opacification. *Mol Vis* 17, 291-9.
37. Hwang H C, Smythe W R, Elshami A A, Kucharczuk J C, Amin K M, Williams J P, Litzky L A, Kaiser L R, Albelda S M (1995). Gene therapy using adenovirus carrying the herpes simplex-thymidine kinase gene to treat in vivo models of human malignant mesothelioma and lung cancer. *Am J Respir Cell Mol Biol* 13, 1, 7-16.
38. Rumney S, Kool E T (1995). Structural Optimization of Non-Nucleotide Loop Replacements for Duplex and Triplex DNAs. *J. Am. Chem. Soc.* 117, 5635-46.
39. Takeshita M, Chang C N, Johnson F, Will S, Grollman A P (1987). Oligodeoxynucleotides containing synthetic abasic sites. Model substrates for DNA polymerases and apurinic/apyrimidinic endonucleases. *J. Biol. Chem.* 262, 10171-9.
40. Lin C, Xie M, Chen J J, Liu Y, Yan H (2006). Rolling-circle amplification of a DNA nanojunction. *Angew Chem Int Ed Engl* 45, 45, 7537-9.
41. Chu B C, Orgel L E (1992). The stability of different forms of double-stranded decoy DNA in serum and nuclear extracts. *Nucleic Acids Res* 20, 21, 5857-8.
42. Sambrook J, Russell D W (2001). *Molecular cloning: a laboratory manual*. Cold Spring Harbor, N.Y., Cold Spring Harbor Laboratory Press.
43. Li M, Wilson D M, 3rd (2014). Human apurinic/apyrimidinic endonuclease 1. *Antioxid Redox Signal* 20, 4, 678-707.
44. Mohr D, Frey S, Fischer T, Guttler T, Gorlich D (2009). Characterisation of the passive permeability barrier of nuclear pore complexes. *EMBO J* 28, 17, 2541-53.
45. Rybenkov V V, Cozzarelli N R, Vologodskii A V (1993). Probability of DNA knotting and the effective diameter of the DNA double helix. *Proc Natl Acad Sci USA* 90, 11, 5307-11.
46. Wiedenheft B, Sternberg S H, Doudna J A (2012). RNA-guided genetic silencing systems in bacteria and archaea. *Nature* 482, 7385, 331-8.
47. Horvath P, Barrangou R (2010). CRISPR/Cas, the immune system of bacteria and archaea. *Science* 327, 5962, 167-70.
48. Barrangou R, Fremaux C, Deveau H, Richards M, Boyaval P, Moineau S, Romero D A, Horvath P (2007). CRISPR provides acquired resistance against viruses in prokaryotes. *Science* 315, 5819, 1709-12.
49. Marraffini L A, Sontheimer E J (2008). CRISPR interference limits horizontal gene transfer in staphylococci by targeting DNA. *Science* 322, 5909, 1843-5.
50. Jinek M, Chylinski K, Fonfara I, Hauer M, Doudna J A, Charpentier E (2012). A programmable dual-RNA-guided DNA endonuclease in adaptive bacterial immunity. *Science* 337, 6096, 816-21.
51. Ran F A, Hsu P D, Wright J, Agarwala V, Scott D A, Zhang F (2013). Genome engineering using the CRISPR-Cas9 system. *Nat Protoc* 8, 11, 2281-308.
52. *Mali* P, Yang L, Esvelt K M, Aach J, Guell M, DiCarlo J E, Norville J E, Church G M (2013). RNA-guided human genome engineering via Cas9. *Science* 339, 6121, 823-6.
53. Niang M, Bei A K, Madnani K G, Pelly S, Dankwa S, Kanjee U, Gunalan K, Amaladoss A, Yeo K P, Bob N S, Malleret B, Duraisingh M T, Preiser P R (2014). STEVOR is a *Plasmodium falciparum* erythrocyte binding protein that mediates merozoite invasion and rosetting. *Cell Host Microbe* 16, 1, 81-93.

The invention claimed is:

1. A dumbbell-shaped expression vector wherein said vector comprises:
   one or more linear or hairpin-shaped transcription cassettes each comprising a nucleotide sequence encoding a nucleic acid molecule to be expressed; and
   at least:
      a nucleotide sequence comprising at least one internal loop domain that comprises an abasic site or nucleotide mismatch.

2. The vector according to of claim 1 wherein the one or more linear or hairpin-shaped transcription cassettes each comprising a nucleotide sequence encoding a nucleic acid molecule to be expressed is linked to a minimal transcription promoter nucleotide sequence.

3. The vector according to claim 2 wherein said minimal transcription promoter nucleotide sequence further comprises a transcription termination nucleotide sequence wherein transcription initiation and termination nucleotide sequences are operatively coupled.

4. A dumbbell-shaped expression vector wherein said vector comprises:
   one or more linear or hairpin-shaped transcription cassettes each comprising a nucleotide sequence encoding a nucleic acid molecule to be expressed,
   wherein said nucleic acid encodes a therapeutic protein or peptide that is an antigen or CRISPR-associated protein and at least a nucleotide sequence comprising at least one internal loop domain that comprises an abasic site or nucleotide mismatch.

5. The vector according to of claim 4, wherein the one or more linear or hairpin-shaped transcription cassettes each comprising a nucleotide sequence encoding a nucleic acid molecule to be expressed is linked to a minimal transcription promoter nucleotide sequence.

6. The vector according to claim 5, wherein said minimal transcription promoter nucleotide sequence further comprises a transcription termination nucleotide sequence wherein transcription initiation and termination nucleotide sequences are operatively coupled.

7. The vector according to claim 4, which further comprises a nucleotide sequence comprising a repair template, which is a sequence with homology to part of the mammalian genome.

8. The vector according to claim 7 wherein said repair template can be inserted directly next to the loop domain or is the loop domain.

9. The vector according to claim 4, wherein the CRISPR-associated protein (Cas) is Cas9, Cas9n, hSpCas9 or hSpCas9n.

10. The vector according to claim 1 or 4 wherein said abasic site comprises one or more apurinic/apyrimidinic abasic sites.

11. The vector according to claim 1 or 4 wherein said nucleotide mismatch comprises a tetrahydrofuran-based mimic of an abasic site.

12. The vector according to claim 1 or 4 wherein said nucleic acid is selected from the group consisting of: a microRNA, a siRNA or shRNA, an antisense RNA oligonucleotide, an antisense miRNA, a trans-splicing RNA, a guide RNA, single-guide RNA, crRNA, or tracrRNA, a trans-splicing RNA, a pre-mRNA or mRNA, hsa-mir-30 stem, hsa-mir-125b, and hsa-mir-21.

13. A pharmaceutical composition comprising a dumbbell-shaped vector according to claim 1 or 4.

14. The vector according to claim 1 or 4 that further comprises a nucleotide sequence comprising a DNA nuclear targeting sequence.

15. The vector according to claim 1 or 4 that further comprises a nucleotide sequence comprising an enhancer sequence.

16. The vector according to claim 15 that comprises at least one intron.

17. The vector according to claim 1 or 4 that comprises a post-transcriptional regulatory element or a constitutive transport element.

18. The vector according to claim 17 wherein said post-transcriptional regulatory element is the woodchuck hepatitis virus post-transcriptional regulatory element (WPRE).

* * * * *

SEQUENCE LISTING

<160> NUMBER OF SEQ ID NOS: 128

<210> SEQ ID NO 1
<211> LENGTH: 263
<212> TYPE: DNA
<213> ORGANISM: artificial sequence
<220> FEATURE:
<223> OTHER INFORMATION: part of a vector

<400> SEQUENCE: 1
aggtcgggca ggaagagggc ctatttccca tgattccttc atatttgcat atacgataca    60
aggctgttag agagataatt agaattaatt tgactgtaaa cacaaagata ttagtacaaa   120
atacgtgacg tagaaagtaa taatttcttg ggtagtttgc agttttaaaa ttatgtttta   180
aaatggacta tcatatgctt accgtaactt gaaagtattt cgatttcttg gctttatata   240
tcttgtggaa aggacgaaac acc                                           263

<210> SEQ ID NO 2
<211> LENGTH: 228
<212> TYPE: DNA
<213> ORGANISM: artificial sequence
<220> FEATURE:
<223> OTHER INFORMATION: part of a vector

<400> SEQUENCE: 2
aattcgaacg ctgacgtcat caacccgctc caaggaatcg cgggcccagt gtcactaggc    60
gggaacaccc agcgcgcgtg cgccctggca ggaagatggc tgtgagggac aggggagtgg   120
cgccctgcaa tatttgcatg tcgctatgtg ttctgggaaa tcaccataaa cgtgaaatgt   180
ctttggattt gggaatctta taagttctgt atgagaccac agatctaa               228

<210> SEQ ID NO 3
<211> LENGTH: 99
<212> TYPE: DNA
<213> ORGANISM: artificial sequence
<220> FEATURE:
<223> OTHER INFORMATION: part of a vector

<400> SEQUENCE: 3
atatttgcat gtcgctatgt gttctgggaa atcaccataa acgtgaaatg tctttggatt    60
tgggaatctt ataagttctg tatgagacca cagatctaa                          99

<210> SEQ ID NO 4
<211> LENGTH: 99
<212> TYPE: DNA
<213> ORGANISM: artificial sequence
<220> FEATURE:
<223> OTHER INFORMATION: part of a vector

<400> SEQUENCE: 4
atatttgcat gtcgctatgt gttctgggaa atcaccataa acgtgaaatg tctttggatt    60
tgggaatctt ataagttctg tatgagacgg atctaaaaa                          99

<210> SEQ ID NO 5
<211> LENGTH: 604
<212> TYPE: DNA
<213> ORGANISM: artificial sequence
<220> FEATURE:
<223> OTHER INFORMATION: part of a vector

<400> SEQUENCE: 5
gaattcaagg taccagatct tagttattaa tagtaatcaa ttacggggtc attagttcat    60

```
agcccatata tggagttccg cgttacataa cttacggtaa atggcccgcc tggctgaccg      120
cccaacgacc cccgcccatt gacgtcaata atgacgtatg ttcccatagt aacgccaata      180
gggactttcc attgacgtca atgggtggag tatttacggt aaactgccca cttggcagta      240
catcaagtgt atcatatgcc aagtacgccc cctattgacg tcaatgacgg taaatggccc      300
gcctggcatt atgcccagta catgacctta tgggactttc ctacttggca gtacatctac      360
gtattagtca tcgctattac catggtgatg cggttttggc agtacatcaa tgggcgtgga      420
tagcggtttg actcacgggg atttccaagt ctccacccca ttgacgtcaa tgggagtttg      480
ttttggcacc aaaatcaacg ggactttcca aaatgtcgta acaactccgc cccattgacg      540
caaatgggcg gtaggcgtgt acggtgggag gtctatataa gcagagctgg tttagtgaac      600
cgtg                                                                  604

<210> SEQ ID NO 6
<211> LENGTH: 38
<212> TYPE: DNA
<213> ORGANISM: artificial sequence
<220> FEATURE:
<223> OTHER INFORMATION: part of a vector

<400> SEQUENCE: 6
tggttgctga ctaattgaga tgcatgcttt gcatactt                              38

<210> SEQ ID NO 7
<211> LENGTH: 21
<212> TYPE: DNA
<213> ORGANISM: artificial sequence
<220> FEATURE:
<223> OTHER INFORMATION: part of a vector

<400> SEQUENCE: 7
agcctgggga ctttccacac c                                               21

<210> SEQ ID NO 8
<211> LENGTH: 72
<212> TYPE: DNA
<213> ORGANISM: artificial sequence
<220> FEATURE:
<223> OTHER INFORMATION: part of a vector

<400> SEQUENCE: 8
tggttgctga ctaattgaga tgcatgcttt gcatacttct gcctgctggg gagcctgggg      60
actttccaca cc                                                         72

<210> SEQ ID NO 9
<211> LENGTH: 237
<212> TYPE: DNA
<213> ORGANISM: artificial sequence
<220> FEATURE:
<223> OTHER INFORMATION: part of a vector

<400> SEQUENCE: 9
cgatggagcg gagaatgggc ggaactgggc ggagttaggg gcgggatggg cggagttagg      60
ggcgggacta tggttgctga ctaattgaga tgcatgcttt gcatacttct gcctgctggg      120
gagcctgggg actttccaca cctggttgct gactaattga gatgcatgct ttgcatactt      180
ctgcctgctg gggagcctgg ggactttcca caccctaact gacacacatt ccacagc        237

<210> SEQ ID NO 10
```

```
<211> LENGTH: 137
<212> TYPE: DNA
<213> ORGANISM: artificial sequence
<220> FEATURE:
<223> OTHER INFORMATION: part of a vector

<400> SEQUENCE: 10
caggtaagta tcaaggttac aagacaggtt taaggagacc aatagaaact gggcttgtcg      60
agacagagac gactcttgcg tttctgatag gcacctattg gtcttactga catccacttt    120
gcctttctct ccacagg                                                    137

<210> SEQ ID NO 11
<211> LENGTH: 594
<212> TYPE: DNA
<213> ORGANISM: artificial sequence
<220> FEATURE:
<223> OTHER INFORMATION: part of a vector

<400> SEQUENCE: 11
ataatcaacc tctggattac aaaatttgtg aaagattgac tggtattctt aactatgttg      60
ctccttttac gctatgtgga tacgctgctt taatgccttt gtatcatgct attgcttccc    120
gtatggcttt cattttctcc tccttgtata atcctggttg gctgtctctt tatgaggagt    180
tgtggcccgt tgtcaggcaa cgtggcgtgg tgtgcactgt gtttgctgac gcaaccccca    240
ctggttgggg cattgccacc acctgtcagc tcctttccgg gactttcgct ttccccctcc    300
ctattgccac ggcggaactc atcgccgcct gccttgcccg ctgctggaca ggggctcggc    360
tgttgggcac tgacaattcc gtggtgttgt cggggaaatc atcgtccttt ccttggctgc    420
tcgcctgtgt tgccacctgg attctgcgcg gacgtccttc tgctacgtcc cttcggccc    480 tcaatccagc ggaccttcct tcccgcggcc tgctgccggc tctgcggcct cttccgcgtc    540
ttcgccttcg ccctcagacg agtcggatct ccctttgggc cgcctccccg catc          594

<210> SEQ ID NO 12
<211> LENGTH: 56
<212> TYPE: DNA
<213> ORGANISM: artificial sequence
<220> FEATURE:
<223> OTHER INFORMATION: primer

<400> SEQUENCE: 12
gatccgagct gtttctgagg agccttcaag agaggctcct cagaaacagc tctttt         56

<210> SEQ ID NO 13
<211> LENGTH: 56
<212> TYPE: DNA
<213> ORGANISM: artificial sequence
<220> FEATURE:
<223> OTHER INFORMATION: primer

<400> SEQUENCE: 13
tcgagaaaaa gagctgtttc tgaggagcct ctcttgaagg ctcctcagaa acagct         56

<210> SEQ ID NO 14
<211> LENGTH: 58
<212> TYPE: DNA
<213> ORGANISM: artificial sequence
<220> FEATURE:
<223> OTHER INFORMATION: primer

<400> SEQUENCE: 14
gatccgctga ccctgaagtt catcttcaag agagatgaac ttcagggtca gcttttc        58
```

<210> SEQ ID NO 15
<211> LENGTH: 58
<212> TYPE: DNA
<213> ORGANISM: artificial sequence
<220> FEATURE:
<223> OTHER INFORMATION: primer

<400> SEQUENCE: 15
tcgagaaaaa gctgaccctg aagttcatct ctcttgaaga tgaacttcag ggtcagcg          58

<210> SEQ ID NO 16
<211> LENGTH: 28
<212> TYPE: DNA
<213> ORGANISM: artificial sequence
<220> FEATURE:
<223> OTHER INFORMATION: primer

<400> SEQUENCE: 16
atgcgagctc cgatggagcg gagaatgg                                           28

<210> SEQ ID NO 17
<211> LENGTH: 34
<212> TYPE: DNA
<213> ORGANISM: artificial sequence
<220> FEATURE:
<223> OTHER INFORMATION: primer

<400> SEQUENCE: 17
atgcgaattc gctgtggaat gtgtgtcagt tagg                                    34

<210> SEQ ID NO 18
<211> LENGTH: 30
<212> TYPE: DNA
<213> ORGANISM: artificial sequence
<220> FEATURE:
<223> OTHER INFORMATION: primer

<400> SEQUENCE: 18
atcgtcagat cttgcgctcc tctcagtccc                                         30

<210> SEQ ID NO 19
<211> LENGTH: 36
<212> TYPE: DNA
<213> ORGANISM: artificial sequence
<220> FEATURE:
<223> OTHER INFORMATION: primer

<400> SEQUENCE: 19
atcgataagc tttaaaaaag cacgactcgc agctcc                                  36

<210> SEQ ID NO 20
<211> LENGTH: 68
<212> TYPE: DNA
<213> ORGANISM: artificial sequence
<220> FEATURE:
<223> OTHER INFORMATION: primer

<400> SEQUENCE: 20
tcacaagtta gggtctcagg gaatcacaag ttagggtctc agggaatcac aagttagggt        60
ctcaggga                                                                 68

<210> SEQ ID NO 21
<211> LENGTH: 76
<212> TYPE: DNA

```
<213> ORGANISM: artificial sequence
<220> FEATURE:
<223> OTHER INFORMATION: primer

<400> SEQUENCE: 21
agcttccctg agaccctaac ttgtgattcc ctgagaccct aacttgtgat tccctgagac    60
cctaacttgt gaagct                                                    76

<210> SEQ ID NO 22
<211> LENGTH: 68
<212> TYPE: DNA
<213> ORGANISM: artificial sequence
<220> FEATURE:
<223> OTHER INFORMATION: primer

<400> SEQUENCE: 22
tcaacatcag tctgataagc taatcaacat cagtctgata agctaatcaa catcagtctg    60
ataagcta                                                             68

<210> SEQ ID NO 23
<211> LENGTH: 76
<212> TYPE: DNA
<213> ORGANISM: artificial sequence
<220> FEATURE:
<223> OTHER INFORMATION: primer

<400> SEQUENCE: 23
agcttagctt atcagactga tgttgattag cttatcagac tgatgttgat tagcttatca    60
gactgatgtt gaagct                                                    76

<210> SEQ ID NO 24
<211> LENGTH: 28
<212> TYPE: DNA
<213> ORGANISM: artificial sequence
<220> FEATURE:
<223> OTHER INFORMATION: primer

<400> SEQUENCE: 24
tagaattcat atttgcatgt cgctatgt                                       28

<210> SEQ ID NO 25
<211> LENGTH: 27
<212> TYPE: DNA
<213> ORGANISM: artificial sequence
<220> FEATURE:
<223> OTHER INFORMATION: primer

<400> SEQUENCE: 25
aactcgagaa aaagagctgt ttctgag                                        27

<210> SEQ ID NO 26
<211> LENGTH: 44
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: abasic site AP1

<400> SEQUENCE: 26
atccagtttt ctggantaga attcatattt gcatgtcgct atgt                     44
```

```
<210> SEQ ID NO 27
<211> LENGTH: 43
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: abasic site AP1

<400> SEQUENCE: 27
aaggtctttt gacctnaact cgagaaaaag agctgtttct gag            43

<210> SEQ ID NO 28
<211> LENGTH: 44
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: abasic site AP1

<400> SEQUENCE: 28
atccagtttt cagcantaga attcatattt gcatgtcgct atgt           44

<210> SEQ ID NO 29
<211> LENGTH: 43
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: abasic site AP1

<400> SEQUENCE: 29
aaggtctttt cagcanaact cgagaaaaag agctgtttct gag            43

<210> SEQ ID NO 30
<211> LENGTH: 46
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: abasic site AP3

<400> SEQUENCE: 30
atctccagtt ttctgganta gaattcatat ttgcatgtcg ctatgt         46

<210> SEQ ID NO 31
<211> LENGTH: 46
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: abasic site AP3

<400> SEQUENCE: 31
atcaggtctt ttgacctnaa actcgagaaa aagagctgtt tctgag         46
```

<210> SEQ ID NO 32
<211> LENGTH: 46
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: abasic site AP3

<400> SEQUENCE: 32
atctccagtt ttcagcanta gaattcatat ttgcatgtcg ctatgt          46

<210> SEQ ID NO 33
<211> LENGTH: 46
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: abasic site AP3

<400> SEQUENCE: 33
atctccagtt ttcagcanaa actcgagaaa aagagctgtt tctgag          46

<210> SEQ ID NO 34
<211> LENGTH: 47
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: abasic site S9

<400> SEQUENCE: 34
atcgtccagt tttctggant agaattcata tttgcatgtc gctatgt         47

<210> SEQ ID NO 35
<211> LENGTH: 46
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: abasic site S9

<400> SEQUENCE: 35
atcgaggtct tttgacctna actcgagaaa aagagctgtt tctgag          46

<210> SEQ ID NO 36
<211> LENGTH: 47
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: abasic site S9

<400> SEQUENCE: 36
atcgtccagt tttcagcant agaattcata tttgcatgtc gctatgt         47

```
<210> SEQ ID NO 37
<211> LENGTH: 46
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: abasic site s9

<400> SEQUENCE: 37
atcgaggtct tttcagcana actcgagaaa aagagctgtt tctgag            46

<210> SEQ ID NO 38
<211> LENGTH: 46
<212> TYPE: DNA
<213> ORGANISM: artificial sequence
<220> FEATURE:
<223> OTHER INFORMATION: hairpin template-transcribing dumbbells.

<400> SEQUENCE: 38
ttaggagttt tctcctaagc atatttgcat gtcgctatgt gttctg            46

<210> SEQ ID NO 39
<211> LENGTH: 42
<212> TYPE: DNA
<213> ORGANISM: artificial sequence
<220> FEATURE:
<223> OTHER INFORMATION: hairpin template-transcribing dumbbells.

<400> SEQUENCE: 39
tgcaggatcc ctttttttctc atacagaact tataagattc cc               42

<210> SEQ ID NO 40
<211> LENGTH: 18
<212> TYPE: DNA
<213> ORGANISM: artificial sequence
<220> FEATURE:
<223> OTHER INFORMATION: neutralizing oligonucleotide

<400> SEQUENCE: 40
ttaggagttt tctcctaa                                           18

<210> SEQ ID NO 41
<211> LENGTH: 63
<212> TYPE: DNA
<213> ORGANISM: artificial sequence
<220> FEATURE:
<223> OTHER INFORMATION: hp-s/as

<400> SEQUENCE: 41
gatctaaaaa gagctgtttc tgaggagcct ctcttgaagg ctcctcagaa acagctcttt    60
tta                                                                  63

<210> SEQ ID NO 42
<211> LENGTH: 97
<212> TYPE: DNA
<213> ORGANISM: artificial sequence
<220> FEATURE:
<223> OTHER INFORMATION: hp-miR-s/as

<400> SEQUENCE: 42
gatccaaaaa tcttctcagt aggcaaagag ctgtttctga ggagcctctc ttgaaggctc    60
```
ctcagaaaca gctccgcgct cactgagaag atttttg                              97

<210> SEQ ID NO 43
<211> LENGTH: 53
<212> TYPE: DNA
<213> ORGANISM: artificial sequence
<220> FEATURE:
<223> OTHER INFORMATION: hp-iPT-s/as

<400> SEQUENCE: 43
gatctgagct gtttctgagg agcctctctt gaaggctcct cagaaacagc tca           53

<210> SEQ ID NO 44
<211> LENGTH: 55
<212> TYPE: DNA
<213> ORGANISM: artificial sequence
<220> FEATURE:
<223> OTHER INFORMATION: hp-iPT-as/s

<400> SEQUENCE: 44
tcgacaggct cctcagaaac agctctctct tgaagagctg tttctgagga gcctg         55

<210> SEQ ID NO 45
<211> LENGTH: 104
<212> TYPE: DNA
<213> ORGANISM: artificial sequence
<220> FEATURE:
<223> OTHER INFORMATION: hp-125b

<400> SEQUENCE: 45
gatctaaaaa agcacgactc gcagctccca agagcctaac ccgtggattt aaacggtaaa   60
catcacaagt tagggtctca gggactgaga ggagcgcatt ttta                   104

<210> SEQ ID NO 46
<211> LENGTH: 46
<212> TYPE: DNA
<213> ORGANISM: artificial sequence
<220> FEATURE:
<223> OTHER INFORMATION: primer

<400> SEQUENCE: 46
ttaggagttt tctcctaagc gaattcatat ttgcatgtcg ctatgt                   46

<210> SEQ ID NO 47
<211> LENGTH: 43
<212> TYPE: DNA
<213> ORGANISM: artificial sequence
<220> FEATURE:
<223> OTHER INFORMATION: primer

<400> SEQUENCE: 47
ttaggtcttt tgacctaagc ctcgagaaaa agctgaccct gaa                      43

<210> SEQ ID NO 48
<211> LENGTH: 42
<212> TYPE: DNA
<213> ORGANISM: artificial sequence
<220> FEATURE:
<223> OTHER INFORMATION: primer

<400> SEQUENCE: 48
ttaggagttt tctcctaagc ctagaactag tggatccccg gg                       42

<210> SEQ ID NO 49
<211> LENGTH: 40

```
<212> TYPE: DNA
<213> ORGANISM: artificial sequence
<220> FEATURE:
<223> OTHER INFORMATION: primer

<400> SEQUENCE: 49
ttaggtcttt tgacctaagc ctcgaggtcg acggtatcga                          40

<210> SEQ ID NO 50
<211> LENGTH: 20
<212> TYPE: DNA
<213> ORGANISM: artificial sequence
<220> FEATURE:
<223> OTHER INFORMATION: primer

<400> SEQUENCE: 50
ttaggagttt tctcctaagc                                               20

<210> SEQ ID NO 51
<211> LENGTH: 20
<212> TYPE: DNA
<213> ORGANISM: artificial sequence
<220> FEATURE:
<223> OTHER INFORMATION: primer

<400> SEQUENCE: 51
ttaggtcttt tgacctaagc                                               20

<210> SEQ ID NO 52
<211> LENGTH: 82
<212> TYPE: DNA
<213> ORGANISM: artificial sequence
<220> FEATURE:
<223> OTHER INFORMATION: primer

<400> SEQUENCE: 52
ttaggtcttt tgacctaagc aaaaaagact gatgttgact gttgaatctc atggcaggga    60
aagagtggtc tcatacagaa ct                                            82

<210> SEQ ID NO 53
<211> LENGTH: 82
<212> TYPE: DNA
<213> ORGANISM: artificial sequence
<220> FEATURE:
<223> OTHER INFORMATION: primer

<400> SEQUENCE: 53
ttaggtcttt tgacctaagc aaaaagatgt tgactgttga atctcatggc aacaccggga    60
aagagtggtc tcatacagaa ct                                            82

<210> SEQ ID NO 54
<211> LENGTH: 65
<212> TYPE: DNA
<213> ORGANISM: artificial sequence
<220> FEATURE:
<223> OTHER INFORMATION: primer

<400> SEQUENCE: 54
ttaggtcttt tgacctaagc aaaaacgggt agcttatcag actgatgttg actgttgaat    60
gggaa                                                               65

<210> SEQ ID NO 55
<211> LENGTH: 86
<212> TYPE: DNA
```

```
<213> ORGANISM: artificial sequence
<220> FEATURE:
<223> OTHER INFORMATION: primer

<400> SEQUENCE: 55 ttaggtctttt tgacctaagc aaaaactgat gttgactgtt gaatctcatg gcaacaccag    60
gggaaagagt ggtctcatac agaact                                         86

<210> SEQ ID NO 56
<211> LENGTH: 20
<212> TYPE: DNA
<213> ORGANISM: artificial sequence
<220> FEATURE:
<223> OTHER INFORMATION: primer

<400> SEQUENCE: 56
aattgtccag ttttctggac                                                20

<210> SEQ ID NO 57
<211> LENGTH: 20
<212> TYPE: DNA
<213> ORGANISM: artificial sequence
<220> FEATURE:
<223> OTHER INFORMATION: primer

<400> SEQUENCE: 57
tcgacaggtc ttttgacctg                                                20

<210> SEQ ID NO 58
<211> LENGTH: 50
<212> TYPE: DNA
<213> ORGANISM: artificial sequence
<220> FEATURE:
<223> OTHER INFORMATION: primer

<400> SEQUENCE: 58
gtcgtatcca gtgcagggtc cgaggtattc gcactggata cgacaagagc                50

<210> SEQ ID NO 59
<211> LENGTH: 14
<212> TYPE: DNA
<213> ORGANISM: artificial sequence
<220> FEATURE:
<223> OTHER INFORMATION: primer

<400> SEQUENCE: 59
tcgcactgga tacg                                                      14

<210> SEQ ID NO 60
<211> LENGTH: 22
<212> TYPE: DNA
<213> ORGANISM: artificial sequence
<220> FEATURE:
<223> OTHER INFORMATION: primer

<400> SEQUENCE: 60
gagctgtttc tgaggagcct tc                                             22

<210> SEQ ID NO 61
<211> LENGTH: 16
<212> TYPE: DNA
<213> ORGANISM: artificial sequence
<220> FEATURE:
<223> OTHER INFORMATION: primer

<400> SEQUENCE: 61
```
gtgcagggtc cgaggt                                                      16

<210> SEQ ID NO 62
<211> LENGTH: 19
<212> TYPE: DNA
<213> ORGANISM: artificial sequence
<220> FEATURE:
<223> OTHER INFORMATION: primer

<400> SEQUENCE: 62
tctgggaaat caccataaa                                                   19

<210> SEQ ID NO 63
<211> LENGTH: 24
<212> TYPE: DNA
<213> ORGANISM: artificial sequence
<220> FEATURE:
<223> OTHER INFORMATION: primer

<400> SEQUENCE: 63
ttcatatttg catgtcgcta tgtg                                             24

<210> SEQ ID NO 64
<211> LENGTH: 22
<212> TYPE: DNA
<213> ORGANISM: artificial sequence
<220> FEATURE:
<223> OTHER INFORMATION: primer

<400> SEQUENCE: 64
tcccaaatcc aaagacattt ca                                               22

<210> SEQ ID NO 65
<211> LENGTH: 18
<212> TYPE: DNA
<213> ORGANISM: artificial sequence
<220> FEATURE:
<223> OTHER INFORMATION: primer

<400> SEQUENCE: 65
ctggcaccca gcacaatg                                                    18

<210> SEQ ID NO 66
<211> LENGTH: 20
<212> TYPE: DNA
<213> ORGANISM: artificial sequence
<220> FEATURE:
<223> OTHER INFORMATION: primer

<400> SEQUENCE: 66
gccgatccac acggagtact                                                  20

<210> SEQ ID NO 67
<211> LENGTH: 21
<212> TYPE: DNA
<213> ORGANISM: artificial sequence
<220> FEATURE:
<223> OTHER INFORMATION: primer

<400> SEQUENCE: 67
aaggcatccc ttcctgtatg c                                                21

<210> SEQ ID NO 68
<211> LENGTH: 19
<212> TYPE: DNA

```
<213> ORGANISM: artificial sequence
<220> FEATURE:
<223> OTHER INFORMATION: primer

<400> SEQUENCE: 68
ttgctgtgtc cccgtgatc                                                19

<210> SEQ ID NO 69
<211> LENGTH: 28
<212> TYPE: DNA
<213> ORGANISM: artificial sequence
<220> FEATURE:
<223> OTHER INFORMATION: primer

<400> SEQUENCE: 69
cctacaattc ttctttgggc tgctcgct                                      28

<210> SEQ ID NO 70
<211> LENGTH: 22
<212> TYPE: DNA
<213> ORGANISM: artificial sequence
<220> FEATURE:
<223> OTHER INFORMATION: primer

<400> SEQUENCE: 70
catcttgctg caaagctgaa aa                                            22

<210> SEQ ID NO 71
<211> LENGTH: 19
<212> TYPE: DNA
<213> ORGANISM: artificial sequence
<220> FEATURE:
<223> OTHER INFORMATION: primer

<400> SEQUENCE: 71
ttgctgtgtc cccgtgatc                                                19

<210> SEQ ID NO 72
<211> LENGTH: 21
<212> TYPE: DNA
<213> ORGANISM: artificial sequence
<220> FEATURE:
<223> OTHER INFORMATION: primer

<400> SEQUENCE: 72
cccctgccat caacacgcgt c                                             21

<210> SEQ ID NO 73
<211> LENGTH: 52
<212> TYPE: DNA
<213> ORGANISM: artificial sequence
<220> FEATURE:
<223> OTHER INFORMATION: part of a vector

<400> SEQUENCE: 73
gagctgtttc tgaggagcct tcaagagagg ctcctcagaa acagctcttt tt           52

<210> SEQ ID NO 74
<211> LENGTH: 52
<212> TYPE: DNA
<213> ORGANISM: artificial sequence
<220> FEATURE:
<223> OTHER INFORMATION: part of a vector

<400> SEQUENCE: 74
ctcgacaaag actcctcgga agttctctcc gaggagtctt tgtcgagaaa aa           52
```

<210> SEQ ID NO 75
<211> LENGTH: 52
<212> TYPE: DNA
<213> ORGANISM: artificial sequence
<220> FEATURE:
<223> OTHER INFORMATION: part of a vector

<400> SEQUENCE: 75
gagctgtttc tgaggagcct tcaagagagg ctcctcagaa acagctcttt tt      52

<210> SEQ ID NO 76
<211> LENGTH: 52
<212> TYPE: DNA
<213> ORGANISM: artificial sequence
<220> FEATURE:
<223> OTHER INFORMATION: part of a vector

<400> SEQUENCE: 76
ctcgacaaag actcctcgga agttctctcc gaggagtctt tgtcgagaaa aa      52

<210> SEQ ID NO 77
<211> LENGTH: 57
<212> TYPE: DNA
<213> ORGANISM: artificial sequence
<220> FEATURE:
<223> OTHER INFORMATION: part of a vector

<400> SEQUENCE: 77
aaaaagagct gtttctgagg agcctctctt gaaggctcct cagaaacagc tctttt      57

<210> SEQ ID NO 78
<211> LENGTH: 57
<212> TYPE: DNA
<213> ORGANISM: artificial sequence
<220> FEATURE:
<223> OTHER INFORMATION: part of a vector

<400> SEQUENCE: 78
aaaaagagct gtttctgagg agcctctctt gaaggctcct cagaaacagc tctttt      57

<210> SEQ ID NO 79
<211> LENGTH: 91
<212> TYPE: DNA
<213> ORGANISM: artificial sequence
<220> FEATURE:
<223> OTHER INFORMATION: part of a vector

<400> SEQUENCE: 79
aaaaatcttc tcagtaggca aagagctgtt tctgaggagc ctctcttgaa ggctcctcag      60
aaacagctcc gcgctcactg agaagatttt t                                    91

<210> SEQ ID NO 80
<211> LENGTH: 72
<212> TYPE: DNA
<213> ORGANISM: artificial sequence
<220> FEATURE:
<223> OTHER INFORMATION: part of a vector

<400> SEQUENCE: 80
aaaaagctcg acgagctgtt tctgaggagc ctctcttgaa ggctcctcag aaacagctcg      60
tcgagctttt tt                                                          72

<210> SEQ ID NO 81

```
<211> LENGTH: 72
<212> TYPE: DNA
<213> ORGANISM: artificial sequence
<220> FEATURE:
<223> OTHER INFORMATION: part of a vector

<400> SEQUENCE: 81
aaaaagctcg acggctcctc agaaacagct ctctcttgag agctgtttct gaggagcctg    60
tcgagctttt tt                                                        72

<210> SEQ ID NO 82
<211> LENGTH: 93
<212> TYPE: DNA
<213> ORGANISM: artificial sequence
<220> FEATURE:
<223> OTHER INFORMATION: part of a vector

<400> SEQUENCE: 82
tgcgctcctc tcagtccctg agaccctaac ttgtgatgtt taccgtttaa atccacgggt    60
taggctcttg ggagctgcga gtcgtgcttt ttt                                 93

<210> SEQ ID NO 83
<211> LENGTH: 93
<212> TYPE: DNA
<213> ORGANISM: artificial sequence
<220> FEATURE:
<223> OTHER INFORMATION: part of a vector

<400> SEQUENCE: 83
acgcgaggag agtcagggac tctgggattg aacactacaa atggcaaatt taggtgccca    60
atccgagaac cctcgacgct cagcacgaaa aaa                                 93

<210> SEQ ID NO 84
<211> LENGTH: 99
<212> TYPE: DNA
<213> ORGANISM: artificial sequence
<220> FEATURE:
<223> OTHER INFORMATION: part of a vector

<400> SEQUENCE: 84
aaaaaagcac gactcgcagc tcccaagagc ctaacccgtg gatttaaacg gtaaacatca    60
caagttaggg tctcagggac tgagaggagc gcaatttt                            99

<210> SEQ ID NO 85
<211> LENGTH: 99
<212> TYPE: DNA
<213> ORGANISM: artificial sequence
<220> FEATURE:
<223> OTHER INFORMATION: part of a vector

<400> SEQUENCE: 85
aaaaaagcac gactcgcagc tcccaagagc ctaacccgtg gatttaaacg gtaaacatca    60
caagttaggg tctcagggac tgagaggagc gcaatttt                            99

<210> SEQ ID NO 86
<211> LENGTH: 99
<212> TYPE: DNA
<213> ORGANISM: artificial sequence
<220> FEATURE:
<223> OTHER INFORMATION: part of a vector

<400> SEQUENCE: 86
aaaaaagcac gactcgcagc tcccaagagc ctaacccgtg gatttaaacg gtaaacatca    60
```
caagttaggg tctcagggac tgagaggagc gcaattttt          99

<210> SEQ ID NO 87
<211> LENGTH: 90
<212> TYPE: RNA
<213> ORGANISM: artificial sequence
<220> FEATURE:
<223> OTHER INFORMATION: part of a vector

<400> SEQUENCE: 87
ugcgcuccuc ucagucccug agacccuaac uugugauguu uaccguuuaa auccacgggu          60
uaggcucuug ggagcugcga gucgugcuuu          90

<210> SEQ ID NO 88
<211> LENGTH: 22
<212> TYPE: DNA
<213> ORGANISM: artificial sequence
<220> FEATURE:
<223> OTHER INFORMATION: part of a vector

<400> SEQUENCE: 88
tcacaagtta gggtctcagg ga          22

<210> SEQ ID NO 89
<211> LENGTH: 93
<212> TYPE: DNA
<213> ORGANISM: artificial sequence
<220> FEATURE:
<223> OTHER INFORMATION: part of a vector

<400> SEQUENCE: 89
tgcgctcctc tcagtccctg agaccctaac ttgtgatgtt taccgtttaa atccacgggt          60
taggctcttg ggagctgcga gtcgtgcttt ttt          93

<210> SEQ ID NO 90
<211> LENGTH: 93
<212> TYPE: DNA
<213> ORGANISM: artificial sequence
<220> FEATURE:
<223> OTHER INFORMATION: part of a vector

<400> SEQUENCE: 90
acgcgaggag agtcagggac tctgggattg aacactacaa atggcaaatt taggtgccca          60
atccgagaac cctcgacgct cagcacgaaa aaa          93

<210> SEQ ID NO 91
<211> LENGTH: 22
<212> TYPE: DNA
<213> ORGANISM: artificial sequence
<220> FEATURE:
<223> OTHER INFORMATION: part of a vector

<400> SEQUENCE: 91
tcaacatcag tctgataagc ta          22

<210> SEQ ID NO 92
<211> LENGTH: 31
<212> TYPE: RNA
<213> ORGANISM: artificial sequence
<220> FEATURE:
<223> OTHER INFORMATION: part of a vector

<400> SEQUENCE: 92

-continued ugccaugaga uucaacaguc aacaucaguc u                                                 31

<210> SEQ ID NO 93
<211> LENGTH: 31
<212> TYPE: RNA
<213> ORGANISM: artificial sequence
<220> FEATURE:
<223> OTHER INFORMATION: part of a vector

<400> SEQUENCE: 93
gguguugcca ugagauucaa cagucaacau c                                                 31

<210> SEQ ID NO 94
<211> LENGTH: 35
<212> TYPE: RNA
<213> ORGANISM: artificial sequence
<220> FEATURE:
<223> OTHER INFORMATION: part of a vector

<400> SEQUENCE: 94
auucaacagu caacaucagu cugauaagcu acccg                                             35

<210> SEQ ID NO 95
<211> LENGTH: 35
<212> TYPE: RNA
<213> ORGANISM: artificial sequence
<220> FEATURE:
<223> OTHER INFORMATION: part of a vector

<400> SEQUENCE: 95
cugguguugc caugagauuc aacagucaac aucag                                             35

<210> SEQ ID NO 96
<211> LENGTH: 16
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: abasic site AP1

<400> SEQUENCE: 96
atccagtttt ctggan                                                                  16

<210> SEQ ID NO 97
<211> LENGTH: 15
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: abasic site AP1

<400> SEQUENCE: 97
atccagtttt cagcn                                                                   15

<210> SEQ ID NO 98
<211> LENGTH: 16
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: abasic site AP1

<400> SEQUENCE: 98
aaggtctttt gacctn                                           16

<210> SEQ ID NO 99
<211> LENGTH: 16
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: abasic site AP1

<400> SEQUENCE: 99
aaggtctttt cagcan                                           16

<210> SEQ ID NO 100
<211> LENGTH: 18
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: abasic site AP3

<400> SEQUENCE: 100
atctccagtt ttctggan                                         18

<210> SEQ ID NO 101
<211> LENGTH: 18
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: abasic site AP3

<400> SEQUENCE: 101
atctccagtt ttcagcan                                         18

<210> SEQ ID NO 102
<211> LENGTH: 18
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: abasic site AP3

<400> SEQUENCE: 102
atcaggtctt ttgacctn                                         18

<210> SEQ ID NO 103
<211> LENGTH: 18
<212> TYPE: DNA

```
<213> ORGANISM: artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: abasic site AP3

<400> SEQUENCE: 103
atctccagtt ttcagcan                                                 18

<210> SEQ ID NO 104
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: abasic site S9

<400> SEQUENCE: 104
atcgtccagt tttctggan                                                19

<210> SEQ ID NO 105
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: abasic site S9

<400> SEQUENCE: 105
atcgtccagt tttcagcan                                                19

<210> SEQ ID NO 106
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: abasic site S9

<400> SEQUENCE: 106
atcgaggtct tttgacctn                                                19

<210> SEQ ID NO 107
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: abasic site S9

<400> SEQUENCE: 107
atcgaggtct tttcagcan                                                19

<210> SEQ ID NO 108
<211> LENGTH: 20
```

```
<212> TYPE: DNA
<213> ORGANISM: artificial sequence
<220> FEATURE:
<223> OTHER INFORMATION: guide sequence

<400> SEQUENCE: 108 taccccttg aacccctctt                                                      20

<210> SEQ ID NO 109
<211> LENGTH: 20
<212> TYPE: DNA
<213> ORGANISM: artificial sequence
<220> FEATURE:
<223> OTHER INFORMATION: guide sequence

<400> SEQUENCE: 109
gatgcggttc cagcttctgc                                                     20

<210> SEQ ID NO 110
<211> LENGTH: 20
<212> TYPE: DNA
<213> ORGANISM: artificial sequence
<220> FEATURE:
<223> OTHER INFORMATION: guide sequence

<400> SEQUENCE: 110
tccgggctcc cagcagaagc                                                     20

<210> SEQ ID NO 111
<211> LENGTH: 20
<212> TYPE: DNA
<213> ORGANISM: artificial sequence
<220> FEATURE:
<223> OTHER INFORMATION: guide sequence

<400> SEQUENCE: 111
ctctgcaggt ccctcccgaa                                                     20

<210> SEQ ID NO 112
<211> LENGTH: 19
<212> TYPE: DNA
<213> ORGANISM: artificial sequence
<220> FEATURE:
<223> OTHER INFORMATION: guide sequence

<400> SEQUENCE: 112
cgctaccaga gctaactca                                                      19

<210> SEQ ID NO 113
<211> LENGTH: 72
<212> TYPE: RNA
<213> ORGANISM: Homo sapiens

<400> SEQUENCE: 113
acagucuguc ggguagcuga ccacaacggu acucuaaguu gucaguugua gucagacuau         60
ucgaugggcu gu                                                             72

<210> SEQ ID NO 114
<211> LENGTH: 11
<212> TYPE: DNA
<213> ORGANISM: artificial sequence
<220> FEATURE:
<223> OTHER INFORMATION: Part of a vector

<400> SEQUENCE: 114
```
cactctttcc c                                                           11

<210> SEQ ID NO 115
<211> LENGTH: 6
<212> TYPE: DNA
<213> ORGANISM: artificial sequence
<220> FEATURE:
<223> OTHER INFORMATION: Part of a vector

<400> SEQUENCE: 115 ggatct                                                                 6

<210> SEQ ID NO 116
<211> LENGTH: 11
<212> TYPE: DNA
<213> ORGANISM: artificial sequence
<220> FEATURE:
<223> OTHER INFORMATION: Part of a vector

<400> SEQUENCE: 116
aaaaaggatc t                                                           11

<210> SEQ ID NO 117
<211> LENGTH: 11
<212> TYPE: DNA
<213> ORGANISM: artificial sequence
<220> FEATURE:
<223> OTHER INFORMATION: Part of a vector

<400> SEQUENCE: 117
ggatctaaaa a                                                           11

<210> SEQ ID NO 118
<211> LENGTH: 22
<212> TYPE: DNA
<213> ORGANISM: artificial sequence
<220> FEATURE:
<223> OTHER INFORMATION: Primer

<400> SEQUENCE: 118
catgctcgag gctagcaagc tt                                               22

<210> SEQ ID NO 119
<211> LENGTH: 22
<212> TYPE: DNA
<213> ORGANISM: artificial sequence
<220> FEATURE:
<223> OTHER INFORMATION: Primer

<400> SEQUENCE: 119
catgaagctt gctagcctcg ag                                               22

<210> SEQ ID NO 120
<211> LENGTH: 22
<212> TYPE: DNA
<213> ORGANISM: artificial sequence
<220> FEATURE:
<223> OTHER INFORMATION: Primer

<400> SEQUENCE: 120
ggccacgcgt tgtacaggat cc                                               22

<210> SEQ ID NO 121
<211> LENGTH: 22
<212> TYPE: DNA
<213> ORGANISM: artificial sequence -continued

```
<220> FEATURE:
<223> OTHER INFORMATION: Primer

<400> SEQUENCE: 121
ggccggatcc tgtacaacgc gt                                              22

<210> SEQ ID NO 122
<211> LENGTH: 28
<212> TYPE: DNA
<213> ORGANISM: artificial sequence
<220> FEATURE:
<223> OTHER INFORMATION: Primer

<400> SEQUENCE: 122
cgatacaagg ctgttagaga gataatgg                                        28

<210> SEQ ID NO 123
<211> LENGTH: 21
<212> TYPE: DNA
<213> ORGANISM: artificial sequence
<220> FEATURE:
<223> OTHER INFORMATION: Primer

<400> SEQUENCE: 123
tgcagctctg atcctcactc c                                               21

<210> SEQ ID NO 124
<211> LENGTH: 18
<212> TYPE: DNA
<213> ORGANISM: artificial sequence
<220> FEATURE:
<223> OTHER INFORMATION: Primer

<400> SEQUENCE: 124
tggacagccg gtcagagc                                                   18

<210> SEQ ID NO 125
<211> LENGTH: 28
<212> TYPE: DNA
<213> ORGANISM: artificial sequence
<220> FEATURE:
<223> OTHER INFORMATION: Primer

<400> SEQUENCE: 125
aaaaggacgc gtgccagcaa tgccaccc                                        28

<210> SEQ ID NO 126
<211> LENGTH: 29
<212> TYPE: DNA
<213> ORGANISM: artificial sequence
<220> FEATURE:
<223> OTHER INFORMATION: Primer

<400> SEQUENCE: 126
aatattggat ccggctcctg agtaccacc                                       29

<210> SEQ ID NO 127
<211> LENGTH: 19
<212> TYPE: DNA
<213> ORGANISM: artificial sequence
<220> FEATURE:
<223> OTHER INFORMATION: Primer

<400> SEQUENCE: 127
tccagcttct gctgggagc                                                  19
```

```
<210> SEQ ID NO 128
<211> LENGTH: 20
<212> TYPE: DNA
<213> ORGANISM: artificial sequence
<220> FEATURE:
<223> OTHER INFORMATION: Primer

<400> SEQUENCE: 128
gaagctggaa ccgcatcatc                                               20
```